(12) United States Patent
Angibaud et al.

(10) Patent No.: US 10,745,409 B2
(45) Date of Patent: Aug. 18, 2020

(54) AZEPANE INHIBITORS OF MENIN-MLL INTERACTION

(71) Applicant: Janssen Pharmaceutica NV, Beerse (BE)

(72) Inventors: Patrick René Angibaud, Saint Pierre d'Autils (FR); Vineet Pande, Vosselaar (BE); Barbara Herkert, Flonheim (DE); Daniel Jason Krosky, Blue Bell, PA (US); Olivier Alexis Georges Querolle, Saint Vigor (FR); Aaron Nathaniel Patrick, Doylestown, PA (US); Isabelle Noëlle Constance Pilatte, Louviers (FR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/469,174

(22) PCT Filed: Dec. 14, 2017

(86) PCT No.: PCT/EP2017/082826
§ 371 (c)(1),
(2) Date: Jun. 13, 2019

(87) PCT Pub. No.: WO2018/109088
PCT Pub. Date: Jun. 21, 2018

(65) Prior Publication Data
US 2019/0322685 A1    Oct. 24, 2019

Related U.S. Application Data

(60) Provisional application No. 62/434,549, filed on Dec. 15, 2016.

(30) Foreign Application Priority Data

Jan. 6, 2017  (EP) ..................................... 17150502

(51) Int. Cl.
| | | |
|---|---|---|
| *A61K 31/381* | (2006.01) | |
| *A61K 31/519* | (2006.01) | |
| *A61K 31/55* | (2006.01) | |
| *A61P 35/00* | (2006.01) | |
| *A61P 35/02* | (2006.01) | |
| *C07D 495/04* | (2006.01) | |

(52) U.S. Cl.
CPC ............ *C07D 495/04* (2013.01); *A61P 35/02* (2018.01)

(58) Field of Classification Search
CPC .... A61K 31/381; A61K 31/519; A61K 31/55; A61P 35/00; A61P 35/02; C07D 495/04
See application file for complete search history.

(56) References Cited

U.S. PATENT DOCUMENTS

| | | |
|---|---|---|
| 2004/0043959 A1 | 3/2004 | Bloom et al. |
| 2013/0310333 A1 | 11/2013 | Chesworth et al. |
| 2013/0310334 A1 | 11/2013 | Chesworth et al. |
| 2014/0221345 A1 | 8/2014 | Duncan et al. |
| 2014/0228343 A1 | 8/2014 | Duncan et al. |
| 2014/0275070 A1 | 9/2014 | Grembecka et al. |
| 2014/0329794 A1 | 11/2014 | Duncan et al. |
| 2016/0244475 A1 | 8/2016 | Tatlock et al. |
| 2017/0198006 A1 | 7/2017 | Duncan et al. |
| 2017/0355711 A1 | 12/2017 | Taber et al. |
| 2018/0105531 A1 | 4/2018 | Grembecka et al. |
| 2018/0243328 A1 | 8/2018 | Wu et al. |

FOREIGN PATENT DOCUMENTS

| | | |
|---|---|---|
| WO | WO 1996/040686 A1 | 12/1996 |
| WO | WO 2003/070739 A1 | 8/2003 |
| WO | WO 2003/074083 A1 | 9/2003 |
| WO | WO 2011/029054 A1 | 3/2011 |
| WO | WO 2012/075500 A2 | 6/2012 |
| WO | WO 2012/082436 A3 | 6/2012 |
| WO | WO 2014/035140 A2 | 3/2014 |
| WO | WO 2014/100695 A1 | 6/2014 |
| WO | WO 2014/164543 A1 | 10/2014 |
| WO | WO 2015/191701 A1 | 12/2015 |
| WO | WO 2016/040330 A1 | 3/2016 |
| WO | WO 2016/081732 A1 | 5/2016 |
| WO | WO 2016/195776 A1 | 12/2016 |
| WO | WO 2016/197027 A1 | 12/2016 |
| WO | WO 2017/112768 A1 | 6/2017 |
| WO | WO 2017/161002 A1 | 9/2017 |
| WO | WO 2017/161028 A1 | 9/2017 |
| WO | WO 2017/192543 A1 | 11/2017 |
| WO | WO 2017/207387 A1 | 12/2017 |
| WO | WO 2017/214367 A1 | 12/2017 |
| WO | WO 2018/024602 A1 | 2/2018 |

(Continued)

OTHER PUBLICATIONS

Borkin et al., "Pharmacologic Inhibition of the Menin-MLL Interaction Blocks Progression of MLL Leukemia In Vivo.", Cancer Cell, Apr. 13, 2015, pp. 589-602, vol. 27.

(Continued)

*Primary Examiner* — Brenda L Coleman
(74) *Attorney, Agent, or Firm* — BakerHostetler

(57) ABSTRACT

The present invention relates to pharmaceutical agents useful for therapy and/or prophylaxis in a mammal, and in particular to azepane compounds, pharmaceutical composition comprising such compounds, and their use as menin/MLL protein/protein interaction inhibitors, useful for treating diseases such as cancer, myelodysplastic syndrome (MDS) and diabetes.

10 Claims, No Drawings

Specification includes a Sequence Listing.

(56) References Cited

FOREIGN PATENT DOCUMENTS

| WO | WO 2018/050684 A1 | 3/2018 |
| WO | WO 2018/050686 A1 | 3/2018 |
| WO | WO 2018/053267 A1 | 3/2018 |
| WO | WO 2018/175746 A1 | 9/2018 |

OTHER PUBLICATIONS

Borkin et al., "Property Focused Structure-Based Optimization of Small Molecule Inhibitors of the Protein—Protein Interaction between Menin and Mixed Lineage Leukemia (MLL).", J. Med. Chem., 2016, pp. 892-913, vol. 59.

Cermakova et al., "Validation and Structural Characterization of the LEDGF/p75—MLL Interface as a New Target for theTreatment of MLL-Dependent Leukemia", Cancer Res., Sep. 15, 2014, pp. 5139-5151, vol. 74(18).

Charron et al., "Recent developments in radiolabelled peptides for PET imaging of cancer.", Tetrahedron Letters, 2016, pp. 4119-4127, vol. 57.

Chen et al., "The tumor suppressor menin regulates hematopoiesis and myeloid transformation by influencing Hox gene expression.", PNAS, Jan. 24, 2006, pp. 1018-1023, vol. 103(4).

Cierpicki, T. and Grembecka, J., "Challenges and opportunities in targeting the menin—MLL interaction.", Future Med. Chem., 2014, pp. 447-462, vol. 6(4).

Grembecka et al., "Menin-MLL Inhibitors Reverse Oncogenic Activity of MLL Fusion Proteins in Leukemia.", Nat. Chem. Bio, published on-line on Jan. 29, 2012, DOI: 10.1038/NCHEMBIO. 773; Mar. 2012, pp. 277-284, vol. 8.

He et al., "High-Affinity Small-Molecule Inhibitors of the Menin-Mixed Lineage Leukemia (MLL) Interaction Closely Mimic a Natural Protein—Protein Interaction.", J. Med. Chem., 2014, 1543-1556, vol. 57.

Li et al., "Distinct pathways regulated by menin and by MLL1 in hematopoietic stem cells and developing B cells.", Blood, Sep. 19, 2013, pp. 2039-2046, vol. 122(12).

Malik et al., "Targeting the MLL complex in castration resistant prostate cancer.", Nat. Med., Apr. 2015, pp. 344-352, vol. 21(4).

Marschalek, R., "Mechanisms of leukemogenesis by MLL fusion proteins.", British J. of Haematology, 2010, pp. 141-154, vol. 152.

Meyer et al., "The MLL recombinome of acute leukemias in 2013.", Leukemia, 2013, pp. 2165-2176, vol. 27.

Mishra et al., "The Histone Methyltransferase Activity of MLL1 is Dispensable for Hematopoiesis and Leukemogenesis.", Cell Rep., May 22, 2014, pp. 1239-1247, vol. 7(4).

Pantel et al., "Molecular imaging to guide systemic cancer therapy: Illustrative examples of PET imaging cancer biomarkers.", Cancer Letters, 2017, pp. 25-31, vol. 387.

Ren et al., "Design and synthesis of benzylpiperidine inhibitors targeting the menin—MLL1 interface.", Bioorganic & Medicinal Chemistry Letters, 2016, pp. 4472-4476, vol. 26.

Shah, S.K., et al., "Synthesis and evaluation of CCR5 antagonists containing modified 4-piperidinyl-2-phenyl-1-(phenylsulfonylamino)-butane", Bioorganic & Medicinal Chemistry Letters, 2005, pp. 977-982, vol. 15.

Thiel et al., "Menin as a Hub Controlling Mixed Lineage Leukemia.", Bioessays, Sep. 2012, pp. 771-780, vol. 34(9).

Tomizawa et al., "Repetitive Cycles of High-Dose Cytarabine Are Effective for Childhood Acute Myeloid Leukemia: Long-Term Outcome of the Children With AML Treated on Two Consecutive Trials of Tokyo Children's Cancer Study Group.", Pediatr. Blood Cancer, 2007, pp. 127-132, vol. 49.

Yokoyama et al., "The Menin Tumor Suppressor Protein is an Essential Oncogenic Cofactor for MLL-Associated Leukemogenesis.", Cell, Oct. 21, 2005, pp. 207-218, vol. 123.

Yokoyama, A. and Cleary, M., "Menin Critically Links MLL Proteins with LEDGF on Cancer-Associated Target Genes.", Cancer Cell, Jul. 2008, pp. 36-46, vol. 14.

International Search Report PCT/EP2017/082826, dated Feb. 14, 2018.

Written Opinion PCT/EP2017/082826, dated Feb. 14, 2018.

SEQUENCE LISTING

<160> NUMBER OF SEQ ID NOS: 1

<210> SEQ ID NO 1
<211> LENGTH: 616
<212> TYPE: PRT
<213> ORGANISM: Artificial Sequence
<220> FEATURE:
<223> OTHER INFORMATION: MENIN protein sequence with His tag

<400> SEQUENCE: 1

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro

```
            20                  25                  30
Asp Leu Val Leu Leu Ser Leu Val Leu Gly Phe Val Glu His Phe Leu
            35                  40                  45
Ala Val Asn Arg Val Ile Pro Thr Asn Val Pro Glu Leu Thr Phe Gln
 50                  55                  60
Pro Ser Pro Ala Pro Asp Pro Gly Gly Leu Thr Tyr Phe Pro Val
 65                  70                  75                  80
Ala Asp Leu Ser Ile Ile Ala Ala Leu Tyr Ala Arg Phe Thr Ala Gln
                    85                  90                  95
Ile Arg Gly Ala Val Asp Leu Ser Leu Tyr Pro Arg Glu Gly Gly Val
                100                 105                 110
Ser Ser Arg Glu Leu Val Lys Lys Val Ser Asp Val Ile Trp Asn Ser
            115                 120                 125
Leu Ser Arg Ser Tyr Phe Lys Asp Arg Ala His Ile Gln Ser Leu Phe
            130                 135                 140
Ser Phe Ile Thr Gly Thr Lys Leu Asp Ser Ser Gly Val Ala Phe Ala
145                 150                 155                 160
Val Val Gly Ala Cys Gln Ala Leu Gly Leu Arg Asp Val His Leu Ala
                165                 170                 175
Leu Ser Glu Asp His Ala Trp Val Val Phe Gly Pro Asn Gly Glu Gln
                180                 185                 190
Thr Ala Glu Val Thr Trp His Gly Lys Gly Asn Glu Asp Arg Arg Gly
                195                 200                 205
Gln Thr Val Asn Ala Gly Val Ala Glu Arg Ser Trp Leu Tyr Leu Lys
            210                 215                 220
Gly Ser Tyr Met Arg Cys Asp Arg Lys Met Glu Val Ala Phe Met Val
225                 230                 235                 240
Cys Ala Ile Asn Pro Ser Ile Asp Leu His Thr Asp Ser Leu Glu Leu
                245                 250                 255
Leu Gln Leu Gln Gln Lys Leu Leu Trp Leu Leu Tyr Asp Leu Gly His
                260                 265                 270
Leu Glu Arg Tyr Pro Met Ala Leu Gly Asn Leu Ala Asp Leu Glu Glu
            275                 280                 285
Leu Glu Pro Thr Pro Gly Arg Pro Asp Pro Leu Thr Leu Tyr His Lys
            290                 295                 300
Gly Ile Ala Ser Ala Lys Thr Tyr Tyr Arg Asp Glu His Ile Tyr Pro
305                 310                 315                 320
Tyr Met Tyr Leu Ala Gly Tyr His Cys Arg Asn Arg Asn Val Arg Glu
                325                 330                 335
Ala Leu Gln Ala Trp Ala Asp Thr Ala Thr Val Ile Gln Asp Tyr Asn
            340                 345                 350
Tyr Cys Arg Glu Asp Glu Glu Ile Tyr Lys Glu Phe Phe Glu Val Ala
            355                 360                 365
Asn Asp Val Ile Pro Asn Leu Leu Lys Glu Ala Ser Leu Leu Glu
            370                 375                 380
Ala Gly Glu Glu Arg Pro Gly Glu Gln Ser Gln Gly Thr Gln Ser Gln
385                 390                 395                 400
Gly Ser Ala Leu Gln Asp Pro Glu Cys Phe Ala His Leu Leu Arg Phe
                405                 410                 415
Tyr Asp Gly Ile Cys Lys Trp Glu Glu Gly Ser Pro Thr Pro Val Leu
            420                 425                 430
His Val Gly Trp Ala Thr Phe Leu Val Gln Ser Leu Gly Arg Phe Glu
            435                 440                 445
```

-continued

```
Gly Gln Val Arg Gln Lys Val Arg Ile Val Ser Arg Glu Ala Glu Ala
    450             455             460
Ala Glu Ala Glu Glu Pro Trp Gly Glu Glu Ala Arg Glu Gly Arg Arg
465             470             475             480
Arg Gly Pro Arg Glu Ser Lys Pro Glu Glu Pro Pro Pro Lys
            485             490             495
Lys Pro Ala Leu Asp Lys Gly Leu Gly Thr Gly Gln Gly Ala Val Ser
            500             505             510
Gly Pro Pro Arg Lys Pro Pro Gly Thr Val Ala Gly Thr Ala Arg Gly
            515             520             525
Pro Glu Gly Gly Ser Thr Ala Gln Val Pro Ala Pro Ala Ala Ser Pro
    530             535             540
Pro Pro Glu Gly Pro Val Leu Thr Phe Gln Ser Glu Lys Met Lys Gly
545             550             555             560
Met Lys Glu Leu Leu Val Ala Thr Lys Ile Asn Ser Ser Ala Ile Lys
                565             570             575
Leu Gln Leu Thr Ala Gln Ser Gln Val Gln Met Lys Lys Gln Lys Val
            580             585             590
Ser Thr Pro Ser Asp Tyr Thr Leu Ser Phe Leu Lys Arg Gln Arg Lys
            595             600             605
Gly Leu His His His His His His
    610             615
```

AZEPANE INHIBITORS OF MENIN-MLL INTERACTION

CROSS-REFERENCE TO RELATED APPLICATIONS

This application is a U.S. national stage of PCT Application No. PCT/EP2017/082826, filed Dec. 14, 2017, which claims the benefit of priority of U.S. Patent Application No. 62/434,549, filed Dec. 15, 2016, and European Patent Application No. 17150502.7, filed Jan. 6, 2017, all of which are incorporated by reference herein, in their entireties and for all purposes.

FIELD OF THE INVENTION

The present invention relates to pharmaceutical agents useful for therapy and/or prophylaxis in a mammal, and in particular to azepane compounds, pharmaceutical composition comprising such compounds, and their use as menin/MLL protein/protein interaction inhibitors, useful for treating diseases such as cancer, myelodysplastic syndrome (MDS) and diabetes.

BACKGROUND OF THE INVENTION

Chromosomal rearrangements affecting the mixed lineage leukemia gene (MLL; MLL1; KMT2A) result in aggressive acute leukemias across all age groups and still represent mostly incurable diseases emphasizing the urgent need for novel therapeutic approaches. Acute leukemias harboring these chromosomal translocations of MLL represent as lymphoid, myeloid or biphenotypic disease and constitute 5 to 10% of acute leukemias in adults and approximately 70% in infants (Marschalek, Br J Haematol 2011. 152(2), 141-54; Tomizawa et al., Pediatr Blood Cancer 2007. 49(2), 127-32).

MLL is a histone methyltransferase that methylates histone H3 on lysine 4 (H3K4) and functions in multiprotein complexes. Use of inducible loss-of-function alleles of Mll1 demonstrated that Mll1 plays an essential role in sustaining hematopoietic stem cells (HSCs) and developing B cells although its histone methyltransferase activity is dispensable for hematopoiesis (Mishra et al., Cell Rep 2011. 7(4), 1239-47).

Fusion of MLL with more than 60 different partners has been reported to date and has been associated with leukemia formation/progression (Meyer et al., Leukemia 2013. 27, 2165-2176). Interestingly, the SET (Su(var)3-9, enhancer of zeste, and trithorax) domain of MLL is not retained in chimeric proteins but is replaced by the fusion partner (Thiel et al., Bioessays 2012. 34, 771-80). Recruitment of chromatin modifying enzymes like DotlL and/or the pTEFb complex by the fusion partner leads to enhanced transcription and transcriptional elongation of MLL target genes including HOXA genes (e.g. HOXA9) and the HOX cofactor MEIS1 as the most prominent ones. Aberrant expression of these genes in turn blocks hematopoietic differentiation and enhances proliferation.

Menin which is encoded by the Multiple Endocrine Neoplasia type 1 (MEN1) gene is expressed ubiquitously and is predominantly localized in the nucleus. It has been shown to interact with numerous proteins and is, therefore, involved in a variety of cellular processes. The best understood function of menin is its role as an oncogenic cofactor of MLL fusion proteins. Menin interacts with two motifs within the N-terminal fragment of MLL that is retained in all fusion proteins, MBM1 (menin-binding motif 1) and MBM2 (Thiel et al., Bioessays 2012. 34, 771-80). Menin/MLL interaction leads to the formation of a new interaction surface for lens epithelium-derived growth factor (LEDGF). Although MLL directly binds to LEDGF, menin is obligatory for the stable interaction between MLL and LEDGF and the gene specific chromatin recruitment of the MLL complex via the PWWP domain of LEDGF (Cermakova et al., Cancer Res 2014. 15, 5139-51; Yokoyama & Cleary, Cancer Cell 2008. 8, 36-46). Furthermore, numerous genetic studies have shown that menin is strictly required for oncogenic transformation by MLL fusion proteins suggesting the menin/MLL interaction as an attractive therapeutic target. For example, conditional deletion of Men1 prevents leukomogenesis in bone marrow progenitor cells ectopically expressing MLL fusions (Chen et al., Proc Natl Acad Sci 2006. 103, 1018-23). Similarly, genetic disruption of menin/MLL fusion interaction by loss-of-function mutations abrogates the oncogenic properties of the MLL fusion proteins, blocks the development of leukemia in vivo and releases the differentiation block of MLL-transformed leukemic blasts. These studies also showed that menin is required for the maintenance of HOX gene expression by MLL fusion proteins (Yokoyama et al., Cell 2005. 123, 207-18). In addition, small molecule inhibitors of menin/MLL interaction have been developed suggesting druggability of this protein/protein interaction and have also demonstrated efficacy in preclinical models of AML (Borkin et al., Cancer Cell 2015. 27, 589-602; Cierpicki and Grembecka, Future Med Chem 2014. 6, 447-462). Together with the observation that menin is not a requisite cofactor of MLL1 during normal hematopoiesis (Li et al., Blood 2013. 122, 2039-2046), these data validate the disruption of menin/MLL interaction as a promising new therapeutic approach for the treatment of MLL rearranged leukemia and other cancers with an active HOX/MEIS1 gene signature. For example, an internal partial tandem duplication (PTD) within the 5'region of the MLL gene represents another major aberration that is found predominantly in de novo and secondary AML as well as myeloid dysplasia syndromes. Although the molecular mechanism and the biological function of MLL-PTD is not well understood, new therapeutic targeting strategies affecting the menin/MLL interaction might also prove effective in the treatment of MLL-PTD-related leukemias. Furthermore, castration-resistant prostate cancer has been shown to be dependent on the menin/MLL interaction (Malik et al., Nat Med 2015. 21, 344-52).

Several references describe inhibitors targeting the menin-MLL interaction: WO2011029054, J Med Chem 2016, 59, 892-913 describe the preparation of thienopyrimidine and benzodiazepine derivatives: WO2014164543 describes thienopyrimidine and thienopyridine derivatives; Nature Chemical Biology March 2012, 8, 277-284 and Ren, J.; et al. Bioorg Med Chem Lett (2016), 26(18), 4472-4476 describe thienopyrimidine derivatives; J Med Chem 2014, 57, 1543-1556 describes hydroxy- and aminomethylpiperidine derivatives; Future Med Chem 2014, 6, 447-462 reviews small molecule and peptidomimetic compounds; WO2016/195776 describes furo[2,3-d]pyrimidine, 9H-purine, [1,3]oxazolo[5,4-d]pyrimidine, [1,3]oxazolo[4,5-d]pyrimidine, [1,3]thiazolo[5,4-d]pyrimidine, thieno[2,3-b]pyridine and thieno[2,3-d]pyrimidine derivatives; and WO2016/197027 describes 5,6,7,8-tetrahydropyrido[3,4-d]pyrimidine, 5,6,7,8-tetrahydropyrido]4,3-d]pyrimidine, pyrido[2,3-d]pyrimidine and quinoline derivatives. WO2017112768 describes inhibitors of the menin-MLL interaction. WO2017161002 describes inhibitors of menin-MLL. WO2017161028 describes inhibitors of menin-MLL.

DESCRIPTION OF THE INVENTION

The present invention concerns novel compounds of Formula (I),

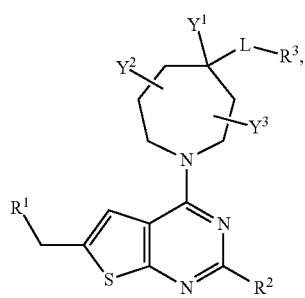

and the tautomers and the stereoisomeric forms thereof, wherein $R^1$ is selected from the group consisting of $CH_3$, $CH_2F$, $CHF_2$ and $CF_3$;

$R^2$ is selected from the group consisting of hydrogen and $CH_3$;

$Y^1$ is selected from the group consisting of hydrogen; $C_{1-6}$alkyl; C-linked 4- to 7-membered non-aromatic heterocyclyl containing at least one nitrogen, oxygen or sulfur atom optionally substituted with a $C_{1-4}$alkyl or cyclopropyl substituent; and $C_{1-4}$alkyl substituted with a substituent selected from the group consisting of fluoro, —CN, phenyl, —OR$^{1Y}$, and —NR$^{2Y}$R$^{2YY}$; wherein $R^{1Y}$ is selected from the group consisting of hydrogen; $C_{1-4}$alkyl optionally substituted with a substituent selected from the group consisting of fluoro, —CN and —C(=O)NR$^{1y}$R$^{2y}$; $C_{2-4}$alkyl substituted with a substituent selected from the group consisting of —OR$^{3y}$ and —NR$^{1y}$R$^{2y}$; and C-linked 4- to 7-membered non-aromatic heterocyclyl containing at least one nitrogen, oxygen or sulfur atom;

$R^{2Y}$ and $R^{2YY}$ are each independently selected from the group consisting of hydrogen; $C_{1-4}$alkyl optionally substituted with a —C(=O)NR$^{1y}$R$^{2y}$ substituent; $C_{2-4}$alkyl substituted with a substituent selected from the group consisting of —OR$^{3y}$ and —NR$^{1y}$R$^{2y}$; and C-linked 4- to 7-membered non-aromatic heterocyclyl containing at least one nitrogen, oxygen or sulfur atom;

$Y^2$ and $Y^3$ are each independently selected from the group consisting of hydrogen; OH; $NH_2$; —C(=O)NR$^{1y}$R$^{2y}$; $C_{1-6}$alkyl; and $C_{1-4}$alkyl substituted with a substituent selected from the group consisting of fluoro, —CN, —OR$^{3Y}$, and —NR$^{4Y}$R$^{4YY}$; with the proviso that when $Y^2$ and $Y^3$ are both substituents at the same carbon atom, and one of $Y^2$ or $Y^3$ is OH or $NH_2$, then the other $Y^3$ or $Y^2$ is H, $C_{1-6}$alkyl, $C_{1-4}$alkyl substituted with a substituent selected from the group consisting of fluoro and —CN, or $C_{2-4}$alkyl substituted with a substituent selected from the group consisting of —OR$^{3Y}$ and —NR$^{4Y}$R$^{4YY}$; wherein $R^{3Y}$ is selected from the group consisting of hydrogen; $C_{1-4}$alkyl optionally substituted with a substituent selected from the group consisting of fluoro, —CN and —C(=O)NR$^{4y}$R$^{5y}$; $C_{2-4}$alkyl substituted with a substituent selected from the group consisting of —OR$^{6y}$ and —NR$^{4y}$R$^{5y}$; and C-linked 4- to 7-membered non-aromatic heterocyclyl containing at least one nitrogen, oxygen or sulfur atom;

$R^{4Y}$ and $R^{4YY}$ are each independently selected from the group consisting of hydrogen; $C_{1-4}$alkyl optionally substituted with a substituent selected from the group consisting of fluoro, —CN and —C(=O)NR$^{1y}$R$^{2y}$; $C_{2-4}$alkyl substituted with a substituent selected from the group consisting of —OR$^{6y}$ and —NR$^{4y}$R$^{5y}$; and C-linked 4- to 7-membered non-aromatic heterocyclyl containing at least one nitrogen, oxygen or sulfur atom; wherein $R^{1y}$, $R^{2y}$, $R^{3y}$, $R^{4y}$, $R^{5y}$ and $R^{6y}$ are each independently selected from the group consisting of hydrogen; $C_{1-4}$alkyl; and C-linked 4- to 7-membered non-aromatic heterocyclyl containing at least one nitrogen, oxygen or sulfur atom; and -L-$R^3$ is selected from (a), (b), (c), (d), (e), or (f):

(a) -L-$R^3$ is —NHR$^{1A}$, wherein $R^{1A}$ is selected from the group consisting of hydrogen; $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$, wherein $R^{1a}$, $R^{2a}$ and $R^{2aa}$ are each independently selected from the group consisting of hydrogen, $C_{1-4}$alkyl and cyclopropyl; with the proviso that when $R^{1A}$ is hydrogen, then $Y^1$ is not hydrogen; or (b) L is selected from the group consisting of —O—, —O—CR$^{1B}$R$^{1BB}$—, —N(R$^B$)—, —N(R$^B$)—CR$^{1B}$R$^{1BB}$—, and —(NR$^B$)—CHR$^{1B}$—CHR$^{2B}$—; and $R^3$ is selected from the group consisting of Ar; Het$^1$; Het$^2$; and a 7- to 10-membered saturated spirocarbobicyclic system; wherein $R^B$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —OR$^{1b}$ and —NR$^{2b}$R$^{2bb}$; wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; —C(=O)NR$^{3B}$R$^{3BB}$; $C_{1-4}$alkyl optionally substituted with a substituent selected from the group consisting of fluoro, phenyl, Het$^1$, and —CN; $C_{2-4}$alkyl substituted with a substituent selected from the group consisting of —OR$^{4B}$ and —NR$^{5B}$R$^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a C-linked 4- to 7-membered non-aromatic heterocyclyl containing at least one nitrogen, oxygen or sulfur atom;

$R^{2B}$ is selected from the group consisting of hydrogen; —OR$^{6B}$; —NR$^{7B}$R$^{7BB}$; —C(=O)NR$^B$R$^{BB}$; $C_{1-4}$alkyl optionally substituted with a substituent selected from the group consisting of fluoro, —CN, —OR$^{4B}$, and —NR$^{5B}$R$^{5BB}$; and C-linked 4- to 7-membered non-aromatic heterocyclyl containing at least one nitrogen, oxygen or sulfur atom; wherein $R^{3B}$, $R^{3BB}$, $R^{4B}$, $R^{5B}$, $R^{5BB}$, $R^{6B}$, $R^{7B}$, $R^{7BB}$, $R^{8B}$ and $R^{8BB}$ are each independently selected from the group consisting of hydrogen; $C_{1-4}$alkyl optionally substituted with a substituent selected from the group consisting of fluoro, —CN and —C(=O)NR$^{9B}$R$^{9BB}$; and $C_{2-4}$alkyl substituted with a substituent selected from the group consisting of —OR$^{10B}$ and —NR$^{11B}$R$^{11BB}$; wherein $R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom; or (c) -L-$R^3$ is selected from the group consisting of —N($R^C$)—CHR$^{1C}$—CO$_2$R$^{2C}$; —N($R^C$)—CHR$^{3C}$—CONR$^{4C}$R$^{4CC}$; —N($R^C$)—COR$^{5C}$; —N($R^C$)—SO$_2$—NR$^{6C}$R$^{6CC}$; wherein $R^C$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —OR$^{1c}$ and —NR$^{2c}$R$^{2cc}$;

$R^{1C}$ and $R^{3C}$ are each selected from the group consisting of hydrogen; —C(=O)NR$^{3c}$R$^{3cc}$; $C_{1-4}$alkyl optionally substituted with a substituent selected from the group consisting of fluoro, phenyl, Het$^1$, and —CN; $C_{2-4}$alkyl substituted with a substituent selected from the group consisting of —OR$^{4c}$ and —NR$^{5c}$R$^{5cc}$; and C-linked 4- to 7-membered non-aromatic heterocyclyl containing at least one nitrogen, oxygen or sulfur atom;

$R^{4C}$ and $R^{6C}$ are each selected from the group consisting of hydrogen, and $C_{1-4}$alkyl optionally substituted with a substituent selected from the group consisting of NR$^{6c}$R$^{6cc}$, Ar, and Het$^1$;

$R^{2C}$ is selected from the group consisting of hydrogen; $C_{1-4}$alkyl optionally substituted with Ar or Het$^1$; Ar; Het$^1$; Het$^2$; and a 7- to 10-membered saturated spirocarbobicyclic system;

$R^{5C}$ is selected from the group consisting of hydrogen; $C_{1-4}$alkyl optionally substituted with —NR$^{2c}$R$^{2cc}$, Ar or Het$^1$; Ar; Het$^1$; Het$^2$; and a 7- to 10-membered saturated spirocarbobicyclic system; wherein $R^{1c}$, $R^{2c}$, $R^{2cc}$, $R^{3c}$, $R^{3cc}$, $R^{4c}$, $R^{5c}$ and $R^{5cc}$ are each independently selected from the group consisting of hydrogen and $C_{1-4}$alkyl; and $R^{6c}$ and $R^{6cc}$ are each independently selected from the group consisting of hydrogen, and $C_{1-4}$alkyl optionally substituted with a substituent selected from the group consisting of —NHC$_{1-4}$alkyl and cyclopropyl; and $R^{4CC}$ and $R^{6CC}$ are each independently selected from the group consisting of hydrogen; $C_{1-4}$alkyl optionally substituted with Ar or Het$^1$; Ar; Het$^1$; Het$^2$; and a 7- to 10-membered saturated spirocarbobicyclic system; or $R^{4C}$ and $R^{4CC}$, or $R^{6C}$ and $R^{6CC}$ together with the nitrogen atom to which they are attached, form a N-linked Het$^2$; or (d) L is selected from —N($R^D$)—CR$^{1D}$R$^{1DD}$— and —N($R^D$)—CR$^{1D}$R$^{1DD}$—CR$^{2D}$R$^{2DD}$—; wherein $R^D$ is selected from the group consisting of hydrogen; $C_{1-4}$alkyl optionally substituted with a substituent selected from the group consisting of fluoro and —CN; and $C_{2-4}$alkyl substituted with a substituent selected from —OR$^{1d}$ and —NR$^{2d}$R$^{2dd}$; wherein $R^{1d}$, $R^{2d}$ and $R^{2dd}$ are each independently selected from the group consisting of hydrogen and $C_{1-4}$alkyl;

$R^{1D}$, $R^{1DD}$, $R^{2D}$ and $R^{2DD}$ are each independently selected from the group consisting of hydrogen and $C_{1-4}$alkyl; and $R^3$ is selected from the group consisting of

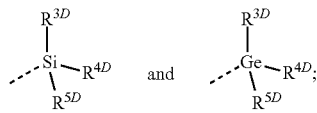

wherein
$R^{3D}$, $R^{4D}$, and $R^{5D}$ are each independently selected from the group consisting of $C_{1-6}$alkyl optionally substituted with a —OH, —OC$_{1-6}$alkyl, or a —NH$_2$ substituent; or (e) -L-$R^3$ is

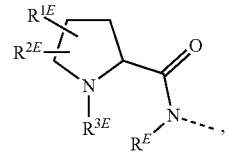

wherein $R^E$ is selected from the group consisting of hydrogen and $C_{1-4}$alkyl;

$R^{1E}$ is selected from the group consisting of hydrogen, fluoro and $C_{1-4}$alkyl; and $R^{2E}$ is selected from the group consisting of fluoro, —OC$_{1-4}$alkyl, and $C_{1-4}$alkyl optionally substituted with 1, 2 or 3 fluoro substituents; or $R^{1E}$ and $R^{2E}$ are bound to the same carbon atom and together form a $C_{3-5}$cycloalkyl or a C-linked 4- to 6-membered heterocyclyl containing an oxygen atom; and $R^{3E}$ is selected from the group consisting of hydrogen; $C_{1-4}$alkyl optionally substituted with a fluoro or a —CN substituent; and $C_{2-4}$alkyl substituted with a substituent selected from the group consisting of —OR$^{4E}$ and —NR$^{5E}$R$^{5EE}$; wherein $R^{4E}$, $R^{5E}$ and $R^{5EE}$ are each independently selected from the group consisting of hydrogen; $C_{1-4}$alkyl optionally substituted with a substituent selected from the group consisting of fluoro, —CN, and —C(=O)NR$^{6E}$R$^{6EE}$; $C_{2-4}$alkyl substituted with a substituent selected from the group consisting of —OR$^{7E}$ and —NR$^{8E}$R$^{8EE}$; and C-linked 4- to 7-membered non-aromatic heterocyclyl containing at least one nitrogen, oxygen or sulfur atom; wherein $R^{6E}$, $R^{6EE}$, $R^{7E}$, $R^{8E}$ and $R^{5EE}$ are each independently selected from the group consisting of hydrogen and $C_{1-4}$alkyl; or (f) -L-$R^3$ is a radical selected from the group consisting of

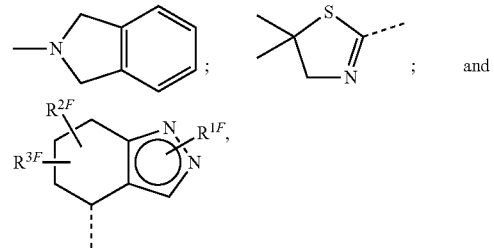

wherein $R^{1F}$ is selected from the group consisting of hydrogen, $C_{1-4}$alkyl and —$C_{2-4}$alkyl-NR$^f$R$^{ff}$; and $R^{2F}$ and $R^{3F}$ are each independently selected from hydrogen and $C_{1-4}$alkyl; wherein $R^f$ and $R^{ff}$ are each independently selected from the group consisting of hydrogen and $C_{1-4}$alkyl;

and wherein

Ar is phenyl optionally substituted with one, two, or three substituents each independently selected from the group consisting of halo, —CN, —OR$^4$, —NR$^5$R$^{5'}$, —C(=O)NR$^5$R$^{5'}$, and $C_{1-4}$alkyl optionally substituted with a substituent selected from the group consisting of fluoro, —CN, —OR$^6$, —NR$^7$R$^{7'}$, and —C(=O)NR$^8$R$^{8'}$;

Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^4$, —NR$^5$R$^{5'}$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$; and Het$^2$ is a non-aromatic heterocyclyl optionally substituted with one, two, or three substituents each independently selected from the group consisting of halo, —CN, —OR$^4$, —NR$^5$R$^{5'}$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$;

wherein
R$^4$, R$^5$, R$^{5'}$, R$^6$, R$^7$, R$^{7'}$, R$^8$ and R$^{8'}$ are each independently selected from the group consisting of hydrogen; C$_{1-4}$alkyl optionally substituted with a substituent selected from the group consisting of fluoro and —C(=O)NR$^9$R$^{9'}$; and C$_{2-4}$alkyl substituted with a substituent selected from the group consisting of —OR$^{10}$ and —NR$^{11}$R$^{11'}$; wherein
R$^9$, R$^{9'}$, R$^{10}$, R$^{11}$ and R$^{11'}$ are each independently selected from the group consisting of hydrogen; C$_{1-4}$alkyl; and C-linked 4- to 7-membered non-aromatic heterocyclyl containing at least one nitrogen, oxygen or sulfur atom;

and the pharmaceutically acceptable salts and the solvates thereof.

The present invention also relates to a pharmaceutical composition comprising a therapeutically effective amount of a compound of Formula (I), a pharmaceutically acceptable salt, or a solvate thereof, and a pharmaceutically acceptable carrier or excipient.

Additionally, the invention relates to a compound of Formula (I), a pharmaceutically acceptable salt, or a solvate thereof, for use as a medicament, and to a compound of Formula (I), a pharmaceutically acceptable salt, or a solvate thereof, for use in the treatment or in the prevention of cancer, myelodysplastic syndrome (MDS) and diabetes.

In a particular embodiment, the invention relates to a compound of Formula (I), a pharmaceutically acceptable salt, or a solvate thereof, for use in the treatment or in the prevention of cancer.

In a specific embodiment said cancer is selected from leukemias, myeloma or a solid tumor cancer (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, leukemias exhibiting HOX/MEIS1 gene expression signatures etc.

The invention also relates to the use of a compound of Formula (I), a pharmaceutically acceptable salt, or a solvate thereof, in combination with an additional pharmaceutical agent for use in the treatment or prevention of cancer, myelodysplastic syndrome (MDS) and diabetes.

Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable salt, or a solvate thereof.

The invention also relates to a product comprising a compound of Formula (I), a pharmaceutically acceptable salt, or a solvate thereof, and an additional pharmaceutical agent, as a combined preparation for simultaneous, separate or sequential use in the treatment or prevention of cancer, myelodysplastic syndrome (MDS) and diabetes.

Additionally, the invention relates to a method of treating or preventing a cell proliferative disease in a warm-blooded animal which comprises administering to the said animal an effective amount of a compound of Formula (I), a pharmaceutically acceptable salt, or a solvate thereof, as defined herein, or a pharmaceutical composition or combination as defined herein.

DETAILED DESCRIPTION OF THE INVENTION

The term 'halo' or 'halogen' as used herein represents fluoro, chloro, bromo and iodo.

The prefix 'C$_{x-y}$' (where x and y are integers) as used herein refers to the number of carbon atoms in a given group. Thus, a C$_{1-6}$alkyl group contains from 1 to 6 carbon atoms, and so on.

The term 'C$_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term 'C$_{2-4}$alkyl' as used herein as a group or part of a group represents a straight or branched chain saturated hydrocarbon radical having from 2 to 4 carbon atoms, such as ethyl, n-propyl, isopropyl, n-butyl, s-butyl, t-butyl and the like.

The term 'C$_{1-6}$alkyl' as used herein as a group or part of a group represents a straight or branched chain saturated hydrocarbon radical having from 1 to 6 carbon atoms such as the groups defined for C$_{1-4}$alkyl and n-pentyl, n-hexyl, 2-methylbutyl and the like.

The term 'C$_{2-6}$alkyl' as used herein as a group or part of a group represents a straight or branched chain saturated hydrocarbon radical having from 2 to 6 carbon atoms such as the groups defined for C$_{2-4}$alkyl and n-pentyl, n-hexyl, 2-methylbutyl and the like.

It will be clear for the skilled person that S(=O)$_2$, (SO$_2$) or SO$_2$ represents a sulfonyl moiety.

It will be clear for the skilled person that CO or C(=O) represents a carbonyl moiety.

As used herein 'spiro bicyclic' systems are cyclic systems wherein two cycles are joined at a single atom. Examples of 7- to 10-membered saturated spirocarbobicyclic systems include, but are not limited to

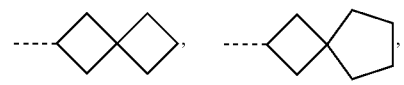

-continued

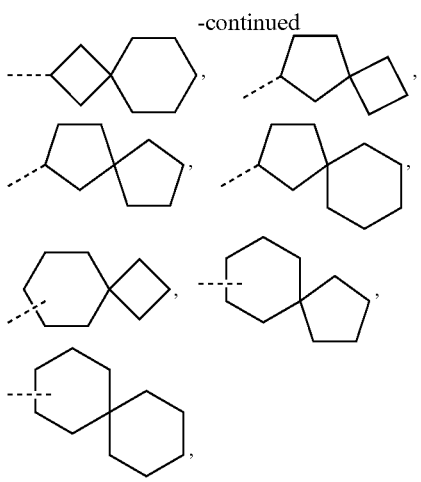

and the like.

In general, whenever the term 'substituted' is used in the present invention, it is meant, unless otherwise indicated or clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using 'substituted' are replaced with a selection from the indicated group, provided that the normal valency is not exceeded, and that the substitution results in a chemically stable compound, i.e. a compound that is sufficiently robust to survive isolation to a useful degree of purity from a reaction mixture.

Combinations of substituents and/or variables are permissible only if such combinations result in chemically stable compounds. 'Stable compound' is meant to indicate a compound that is sufficiently robust to survive isolation to a useful degree of purity from a reaction mixture.

The skilled person will understand that when an atom or radical is substituted with 'a substituent', it is meant that the atom or radical referred to is substituted with one substituent selected from the indicated group.

The skilled person will understand that the term 'optionally substituted' means that the atom or radical indicated in the expression using 'optionally substituted' may or may not be substituted (this means substituted or unsubstituted respectively).

It will be clear for the skilled person that when e.g. L is —N($R^B$)—$CR^{1B}R^{1BB}$— in option (b) of -L-$R^3$, this means that the nitrogen atom substituted with $R^B$ is attached to the azepane ring. This is similar for other definitions of L such as for example —O—$CR^{1B}R^{1BB}$— (oxygen attached to azepane ring), —(N$R^B$)—$CHR^{1B}CHR^{2B}$— (nitrogen atom substituted with $R^B$ attached to the azepane ring), —N($R^D$)—$CR^{1D}R^{1DD}$— (nitrogen atom substituted with $R^D$ attached to the azepane ring), —N($R^D$)—$CR^{1D}R^{1DD}$—$CR^{2D}R^{2DD}$—(nitrogen atom substituted with $R^D$ attached to the azepane ring), or other similar definitions of L in the scope.

When two or more substituents are present on a moiety they may, where possible and unless otherwise indicated or clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom (e.g. a hydrogen on a nitrogen atom may be replaced by a substituent).

Within the context of this invention 'saturated' means 'fully saturated', if not otherwise specified.

A 'non-aromatic group' embraces unsaturated ring systems without aromatic character, partially saturated and fully saturated carbocyclic and heterocyclic ring systems. The term 'partially saturated' refers to rings wherein the ring structure(s) contain(s) at least one multiple bond e.g. a C═C, N═C bond. The term 'fully saturated' refers to rings where there are no multiple bonds between ring atoms. Thus, a 'non-aromatic heterocyclyl' is a non-aromatic monocyclic or bicyclic system, unless otherwise specified, having for example, 3 to 12 ring members, more usually 5 to 10 ring members. Examples of monocyclic groups are groups containing 4 to 7 ring members, more usually, 5 or 6 ring members. Examples of bicyclic groups are those containing 8 to 12, more usually 9 or 10 ring members.

Non-limiting examples of monocyclic heterocyclyl systems containing at least one heteroatom selected from nitrogen, oxygen or sulfur (N, O, S) include, but are not limited to 4- to 7-membered heterocyclyl systems such as azetidinyl, oxetanyl, pyrrolidinyl, tetrahydrofuranyl, piperidinyl, piperazinyl, pyranyl, dihydropyranyl, tetrahydropyranyl, morpholinyl, thiomorpholinyl, and tetrahydro-2H-thiopyranyl 1,1-dioxide, in particular azetidinyl, oxetanyl, pyrrolidinyl, tetrahydrofuranyl, piperidinyl, piperazinyl, pyranyl, dihydropyranyl, tetrahydropyranyl, morpholinyl, and thiomorpholiny. Non-limiting examples of bicyclic heterocyclyl systems containing at least one heteroatom selected from nitrogen, oxygen or sulfur (N, O, S) include, but are not limited to octahydro-1H-indolyl, indolinyl,

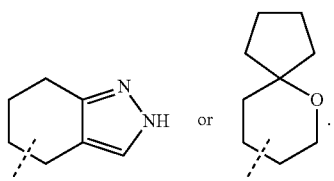

Unless otherwise specified, each can be bound to the remainder of the molecule of Formula (I) through any available ring carbon atom (C-linked) or nitrogen atom (N-linked), and may optionally be substituted, where possible, on carbon and/or nitrogen atoms according to the embodiments.

The term 'C-linked 4- to 7-membered heterocyclyl containing at least one nitrogen, oxygen or sulphur atom' as used herein alone or as part of another group, defines a saturated, cyclic hydrocarbon radical containing at least one nitrogen, oxygen or sulphur atom having from 4 to 7 ring members, as defined above, bound through an available carbon atom. It will be clear that similar the term 'C-linked 4- to 6-membered heterocyclyl containing an oxygen atom' as used herein alone or as part of another group, defines a saturated, cyclic hydrocarbon radical containing one oxygen atom having from 4 to 6 ring members, as defined above, bound through an available carbon atom (such as for example oxetanyl, tetrahydrofuranyl, and tetrahydropyranyl).

Whenever substituents are represented by chemical structure, ' - - - ' represents the bond of attachment to the remainder of the molecule of Formula (I).

Lines (such as ' - - - ') drawn into ring systems indicate that the bond may be attached to any of the suitable ring atoms.

Het$^1$ and Het$^2$ may be attached to the remainder of the molecule of Formula (I) through any available ring carbon or nitrogen atom as appropriate, if not otherwise specified.

It will be clear that a saturated cyclic moiety may, where possible, have substituents on both carbon and nitrogen atoms, unless otherwise is indicated or is clear from the context.

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

Pharmaceutically acceptable salts include acid addition salts and base addition salts. Such salts may be formed by conventional means, for example by reaction of a free acid or a free base form with one or more equivalents of an appropriate base or acid, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable salts as mentioned hereinabove or hereinafter are meant to comprise the therapeutically active non-toxic acid and base salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine salt forms by treatment with appropriate organic and inorganic bases.

Appropriate base salt forms comprise, for example, the ammonium salts, the alkali and earth alkaline metal salts, e.g. the lithium, sodium, potassium, cesium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally, occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^2H$, $^3H$, $^{11}C$ and $^{18}F$. More preferably, the radioactive isotope is $^2H$. In particular, deuterated compounds are intended to be included within the scope of the present invention.

Certain isotopically-labeled compounds of the present invention (e.g., those labeled with $^3H$ and $^{14}C$) may be useful for example in substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$ may afford certain therapeutic advantages resulting from greater metabolic stability (e.g., increased in vivo half-life or reduced dosage requirements) and hence may be preferred in some circumstances. Thus, in a particular embodiment of the present invention, $R^2$ is selected from hydrogen or deuterium, in particular deuterium. Positron emitting isotopes such as $^{15}O$, $^{13}N$, $^{11}C$ and $^{18}F$ are useful for positron emission tomography (PET) studies. PET imaging in cancer finds utility in helping locate and identify tumours, stage the disease and determine suitable treatment. Human cancer cells overexpress many receptors or proteins that are potential disease-specific molecular targets. Radiolabelled tracers that bind with high affinity and specificity to such receptors or proteins on tumour cells have great potential for diagnostic imaging and targeted radionuclide therapy (Charron, Carlie L. et al. Tetrahedron Lett. 2016, 57(37), 4119-4127). Additionally, target-specific PET radiotracers may be used as biomarkers to examine and evaluate pathology, by for example, measuring target expression and treatment response (Austin R. et al. Cancer Letters (2016), doi: 10.1016/j.canlet.2016.05.008).

The present invention relates in particular to compounds of Formula (I) as defined herein, and the tautomers and the stereoisomeric forms thereof, wherein $R^1$ is selected from the group consisting of $CH_3$, $CH_2F$, $CHF_2$ and $CF_3$;

$R^2$ is selected from the group consisting of hydrogen and $CH_3$;

$Y^1$ is selected from the group consisting of hydrogen; $C_{1-6}$alkyl; C-linked 4- to 7-membered non-aromatic heterocyclyl containing at least one nitrogen, oxygen or sulfur atom optionally substituted with a $C_{1-4}$alkyl or cyclopropyl substituent; and $C_{1-4}$alkyl substituted with a substituent selected from the group consisting of fluoro, —CN, phenyl, —OR$^{1Y}$, and —NR$^{2Y}$R$^{2YY}$; wherein $R^{1Y}$, $R^{2Y}$ and $R^{2YY}$ are each independently selected from the group consisting of hydrogen and $C_{1-4}$alkyl;

$Y^2$ and $Y^3$ are each independently selected from the group consisting of hydrogen and $C_{1-6}$alkyl; and -L-$R^3$ is selected from (a), (b), (c), (e), or (f):

(a) -L-$R^3$ is —NHR$^{1A}$, wherein $R^{1A}$ is selected from the group consisting of hydrogen; $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$, wherein $R^{1a}$, $R^{2a}$ and $R^{2aa}$ are each independently selected from the group consisting of hydrogen, $C_{1-4}$alkyl and cyclopropyl; or (b) L is selected from the group consisting of —N(R$^B$)—, —N(R$^B$)—CR$^{1B}$R$^{1BB}$—, and —(NR$^B$)—CHR$^{1B}$—CHR$^{2B}$—; and $R^3$ is selected from the group consisting of Ar; Het$^1$; and Het$^2$; wherein $R^B$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —OR$^{1b}$ and —NR$^{2b}$R$^{2bb}$; wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; $C_{1-4}$alkyl optionally substituted with a substituent selected from the group consisting of fluoro, phenyl, Het$^1$, and —CN; and $C_{2-4}$alkyl substituted with a substituent selected from the group consisting of —OR$^{4B}$ and —NR$^{5B}$R$^{5BB}$; and $R^{1BB}$ is selected from the group consisting of hydrogen and methyl; or $R^{1B}$ and R$^{1BB}$ together with the carbon to which they are attached form a C-linked 4- to 7-membered non-aromatic heterocyclyl containing at least one nitrogen or oxygen atom;

R$^{2B}$ is selected from the group consisting of hydrogen; and C$_{1-4}$alkyl optionally substituted with a substituent selected from the group consisting of fluoro, —CN, —OR$^{4B}$, and —NR$^{5B}$R$^{5BB}$; wherein R$^{4B}$, R$^{5B}$ and R$^{5BB}$ are each independently selected from the group consisting of hydrogen and C$_{1-4}$alkyl; or (c) -L-R$^3$ is selected from the group consisting of —N(R$^C$)—CHR$^{1C}$—CO$_2$R$^{2C}$; —N(R$^C$)—CHR$^{3C}$—CONR$^{4C}$R$^{4CC}$; —N(R$^C$)—COR$^{5C}$; —N(R$^C$)—SO$_2$—NR$^{6C}$R$^{6CC}$; wherein R$^C$ is selected from the group consisting of hydrogen; C$_{1-4}$alkyl optionally substituted with a substituent selected from the group consisting of fluoro, phenyl and —CN; and C$_{2-4}$alkyl substituted with a substituent selected from the group consisting of —OR$^{1c}$ and —NR$^{2c}$R$^{2cc}$;

R$^{1C}$ and R$^{3C}$ are each selected from the group consisting of hydrogen; C$_{1-4}$alkyl optionally substituted with a substituent selected from the group consisting of fluoro, phenyl, Het$^1$, and —CN; and C$_{2-4}$alkyl substituted with a substituent selected from the group consisting of —OR$^{4c}$ and —NR$^{5c}$R$^{5cc}$;

R$^{4C}$ and R$^{6C}$ are each selected from the group consisting of hydrogen, and C$_{1-4}$alkyl optionally substituted with a substituent selected from the group consisting of NR$^{6C}$R$^{6cc}$Ar, and Het$^1$;

R$^{2C}$ is selected from the group consisting of hydrogen; C$_{1-4}$alkyl optionally substituted with Ar or Het$^1$; Ar; Het$^1$; and Het$^2$;

R$^{5C}$ is selected from the group consisting of hydrogen; C$_{1-4}$alkyl optionally substituted with —NR$^{2c}$R$^{2cc}$, Ar or Het$^1$; Ar; Het$^1$; and Het$^2$; wherein R$^{1c}$, R$^{2c}$, R$^{2cc}$, R$^{4C}$, R$^{5c}$ and R$^{5cc}$ are each independently selected from the group consisting of hydrogen and C$_{1-4}$alkyl; and R$^{6c}$ and R$^{6cc}$ are each independently selected from the group consisting of hydrogen, and C$_{1-4}$alkyl optionally substituted with a substituent selected from the group consisting of —NHC$_{1-4}$alkyl and cyclopropyl; and R$^{4CC}$ and R$^{6CC}$ are each independently selected from the group consisting of hydrogen; C$_{1-4}$alkyl optionally substituted with Ar or Het$^1$; Ar; Het$^1$; and Het$^2$; or R$^{4C}$ and R$^{4CC}$, or R$^{6C}$ and R$^{6CC}$ together with the nitrogen atom to which they are attached, form a N-linked Het$^2$; or (e) -L-R$^3$ is

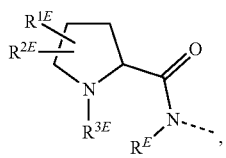

wherein

R$^E$ is selected from the group consisting of hydrogen and C$_{1-4}$alkyl;

R$^{1E}$ is selected from the group consisting of hydrogen, fluoro and C$_{1-4}$alkyl; and R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a C$_{3-5}$cycloalkyl or a C-linked 4- to 6-membered heterocyclyl containing an oxygen atom; and R$^{3E}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{4E}$ and —NR$^{5E}$R$^{5EE}$; wherein R$^{4E}$, R$^{5E}$ and R$^{5EE}$ are each independently selected from the group consisting of hydrogen; C$_{1-4}$alkyl optionally substituted with a substituent selected from the group consisting of fluoro, —CN, and —C(=O)NR$^{6E}$R$^{6EE}$; C$_{2-4}$alkyl substituted with a substituent selected from the group consisting of —OR$^{7E}$ and —NR$^{E}$R$^{EE}$; and C-linked 4- to 7-membered non-aromatic heterocyclyl containing at least one nitrogen, oxygen or sulfur atom; wherein R$^{6E}$, R$^{6EE}$, R$^{7E}$, R$^{8E}$ and R$^{5EE}$ are each independently selected from the group consisting of hydrogen and C$_{1-4}$alkyl; or (f) -L-R$^3$ is a radical selected from the group consisting of

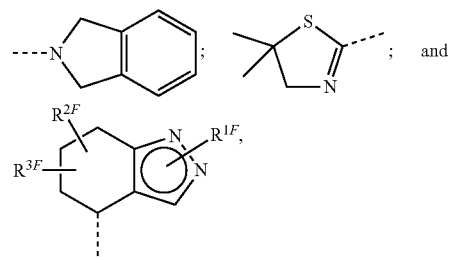

wherein R$^{1F}$ is selected from the group consisting of hydrogen, C$_{1-4}$alkyl and —C$_{2-4}$alkyl-NR$^f$R$^{ff}$; and R$^{2F}$ and R$^{3F}$ are each independently selected from hydrogen and C$_{1-4}$alkyl, in particular hydrogen; wherein R$^f$ and R$^{ff}$ are each independently selected from the group consisting of hydrogen and C$_{1-4}$alkyl;

and wherein

Ar is phenyl optionally substituted with one, two, or three substituents each independently selected from the group consisting of halo, —CN, —OR$^4$, —NR$^5$R$^{5'}$, —C(=O)NR$^5$R$^{5'}$, and C$_{1-4}$alkyl;

Het$^1$ is a monocyclic heteroaryl selected from the group consisting of pyridyl, 4-, 5- or 6-pyrimidinyl, pyrazinyl, pyridazinyl, pyrrolyl, pyrazolyl, imidazolyl, and 4- or 5-thiazolyl; each of which may be optionally substituted with one, two, or three substituents each independently selected from the group consisting of halo and C$_{1-4}$alkyl optionally substituted with a substituent selected from the group consisting of fluoro, —CN, —OR$^6$, —NR$^7$R$^{7'}$, and —C(=O)NR$^8$R$^{8'}$; and Het$^2$ is a non-aromatic heterocyclyl selected from azetidinyl, pyrrolidinyl and piperidinyl, each of which may be optionally substituted with one, two, or three substituents each independently selected from the group consisting of halo, —CN, —OR$^4$, —NR$^5$R$^{5'}$, and C$_{1-4}$alkyl;

wherein

R$^4$, R$^5$, R$^{5'}$, R$^6$, R$^7$, R$^{7'}$, R$^8$ and R$^{8'}$ are each independently selected from the group consisting of hydrogen and C$_{1-4}$alkyl;

and the pharmaceutically acceptable salts and the solvates thereof.

The present invention relates in particular to compounds of Formula (I) as defined herein, and the tautomers and the stereoisomeric forms thereof, wherein $R^1$ is selected from the group consisting of $CH_3$, $CH_2F$, $CHF_2$ and $CF_3$;

$R^2$ is selected from the group consisting of hydrogen and $CH_3$;

$Y^1$ is selected from the group consisting of hydrogen; $C_{1-6}$alkyl; C-linked 4- to 7-membered non-aromatic heterocyclyl containing at least one nitrogen, oxygen or sulfur atom optionally substituted with a $C_{1-4}$alkyl or cyclopropyl substituent; and $C_{1-4}$alkyl substituted with a substituent selected from the group consisting of fluoro, —CN, phenyl, —$OR^{1Y}$, and —$NR^{2Y}R^{2y}$; wherein $R^{1Y}$ is selected from the group consisting of hydrogen; $C_{1-4}$alkyl optionally substituted with a substituent selected from the group consisting of fluoro, —CN and —C(=O)$NR^{1y}R^{2y}$; $C_{2-4}$alkyl substituted with a substituent selected from the group consisting of —$OR^{3y}$ and —$NR^{1y}R^{2y}$; and C-linked 4- to 7-membered non-aromatic heterocyclyl containing at least one nitrogen, oxygen or sulfur atom;

$R^{2Y}$ and $R^{2YY}$ are each independently selected from the group consisting of hydrogen; $C_{1-4}$alkyl optionally substituted with a —C(=O)$NR^{1y}R^{2y}$ substituent; $C_{2-4}$alkyl substituted with a substituent selected from the group consisting of —$OR^{3y}$ and —$NR^{1y}R^{2y}$; and C-linked 4- to 7-membered non-aromatic heterocyclyl containing at least one nitrogen, oxygen or sulfur atom;

$Y^2$ and $Y^3$ are each independently selected from the group consisting of hydrogen; OH; $NH_2$; —C(=O)$NR^{1y}R^{2y}$; $C_{1-6}$alkyl; and $C_{1-4}$alkyl substituted with a substituent selected from the group consisting of fluoro, —CN, —$OR^{3Y}$, and —$NR^{4Y}R^{4Y}$; with the proviso that when $Y^2$ and $Y^3$ are both substituents at the same carbon atom, and one of $Y^2$ or $Y^3$ is OH or $NH_2$, then the other $Y^3$ or $Y^2$ is H, $C_{1-6}$alkyl, $C_{1-4}$alkyl substituted with a substituent selected from the group consisting of fluoro and —CN, or $C_{2-4}$alkyl substituted with a substituent selected from the group consisting of —$OR^{3Y}$ and —$NR^{4Y}R^{4YY}$; wherein $R^{3Y}$ is selected from the group consisting of hydrogen; $C_{1-4}$alkyl optionally substituted with a substituent selected from the group consisting of fluoro, —CN and —C(=O)$NR^{4y}R^{5y}$; $C_{2-4}$alkyl substituted with a substituent selected from the group consisting of —$OR^{6y}$ and —$NR^{4y}R^{5Y}$; and C-linked 4- to 7-membered non-aromatic heterocyclyl containing at least one nitrogen, oxygen or sulfur atom;

$R^{4Y}$ and $R^{4YY}$ are each independently selected from the group consisting of hydrogen; $C_{1-4}$alkyl optionally substituted with a substituent selected from the group consisting of fluoro, —CN and —C(=O)$NR^{1y}R^{2y}$; $C_{2-4}$alkyl substituted with a substituent selected from the group consisting of —$OR^{6y}$ and —$NR^{4y}R^{5y}$; and C-linked 4- to 7-membered non-aromatic heterocyclyl containing at least one nitrogen, oxygen or sulfur atom; wherein $R^{1y}$, $R^{2y}$, $R^{3y}$, $R^{4y}$, $R^{5y}$ and $R^{6y}$ are each independently selected from the group consisting of hydrogen; $C_{1-4}$alkyl; and C-linked 4- to 7-membered non-aromatic heterocyclyl containing at least one nitrogen, oxygen or sulfur atom; and -L-$R^3$ is selected from (a), (b), (c), (d), or (e):

(a) -L-$R^3$ is —$NHR^{1A}$, wherein $R^{1A}$ is selected from the group consisting of hydrogen; $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$ and $R^{2aa}$ are each independently selected from the group consisting of hydrogen, $C_{1-4}$alkyl and cyclopropyl; with the proviso that when $R^{1A}$ is hydrogen, then $Y^1$ is not hydrogen; or (b) L is selected from the group consisting of —N($R^B$)—, —N($R^B$)—$CR^{1B}R^{1BB}$—, and —(N$R^B$)—$CHR^{1B}$—$CHR^{2B}$—; and $R^3$ is selected from the group consisting of Ar; $Het^1$; $Het^2$; and a 7- to 10-membered saturated spiro-carbobicyclic system; wherein $R^B$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —$OR^{1b}$ and —$NR^{2b}R^{2bb}$; wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; —C(=O)$NR^{3B}R^{3BB}$; $C_{1-4}$alkyl optionally substituted with a substituent selected from the group consisting of fluoro, phenyl, $Het^1$, and —CN; $C_{2-4}$alkyl substituted with a substituent selected from the group consisting of —$OR^{4B}$ and —$NR^{5B}R^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a C-linked 4- to 7-membered non-aromatic heterocyclyl containing at least one nitrogen, oxygen or sulfur atom;

$R^{2B}$ is selected from the group consisting of hydrogen; —$OR^{6B}$; —$NR^{7B}R^{7BB}$; —C(=O)$NR^{8B}R^{8BB}$; $C_{1-4}$alkyl optionally substituted with a substituent selected from the group consisting of fluoro, —CN, —$OR^{4B}$, and —$NR^{5B}R^{5BB}$; and C-linked 4- to 7-membered non-aromatic heterocyclyl containing at least one nitrogen, oxygen or sulfur atom; wherein $R^{3B}$, $R^{3BB}$, $R^{4B}$, $R^{5B}$, $R^{5BB}$, $R^{6B}$, $R^{7B}$, $R^{7BB}$, $R^{8B}$ and $R^{8BB}$ are each independently selected from the group consisting of hydrogen; $C_{1-4}$alkyl optionally substituted with a substituent selected from the group consisting of fluoro, —CN and —C(=O)$NR^{9B}R^{9BB}$; and $C_{2-4}$alkyl substituted with a substituent selected from the group consisting of —$OR^{10B}$ and —$NR^{11B}R^{11BB}$; wherein $R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom; or (c) -L-$R^3$ is selected from the group consisting of —N($R^C$)—$CHR^{1C}$—$CO_2R^{2C}$; —N($R^C$)—$CHR^{3C}$—$CONR^{4C}R^{4CC}$; —N($R^C$)—$COR^{5C}$; —N($R^C$)—$SO_2$—$NR^{6C}R^{6CC}$; wherein $R^C$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —$OR^{1c}$ and —$NR^{2c}R^{2cc}$;

$R^{1C}$ and $R^{3C}$ are each selected from the group consisting of hydrogen; —C(=O)$NR^{3c}R^{3cc}$; $C_{1-4}$alkyl optionally substituted with a substituent selected from the group consisting of fluoro, phenyl, $Het^1$, and —CN; $C_{2-4}$alkyl substituted with a substituent selected from the group consisting of —$OR^{4c}$ and —$NR^{5c}R^{5cc}$; and C-linked 4- to 7-membered non-aromatic heterocyclyl containing at least one nitrogen, oxygen or sulfur atom;

$R^{4C}$ and $R^{6C}$ are each selected from the group consisting of hydrogen, and $C_{1-4}$alkyl optionally substituted with a substituent selected from the group consisting of $NR^{6c}R^{6cc}$, Ar, and $Het^1$;

$R^{2C}$ is selected from the group consisting of hydrogen; $C_{1-4}$alkyl optionally substituted with Ar or $Het^1$; Ar; $Het^1$; $Het^2$; and a 7- to 10-membered saturated spirocarbobicyclic system;

$R^{5C}$ is selected from the group consisting of hydrogen; $C_{1-4}$alkyl optionally substituted with —$NR^{2c}R^{2cc}$, Ar or $Het^1$; Ar; $Het^1$; $Het^2$; and a 7- to 10-membered saturated spirocarbobicyclic system; wherein $R^{1c}$, $R^{2c}$, $R^{2cc}$, $R^{3c}$, $R^{3cc}$, $R^{4c}$, $R^{5c}$ and $R^{5cc}$ are each independently selected from the group consisting of hydrogen and $C_{1-4}$alkyl; and $R^{6c}$ and $R^{6cc}$ are each independently selected from the group consisting of hydrogen, and $C_{1-4}$alkyl optionally substituted with a substituent selected from the group consisting of —$NHC_{1-4}$alkyl and cyclopropyl; and $R^{4CC}$ and $R^{6CC}$ are each independently selected from the group consisting of hydrogen; $C_{1-4}$alkyl optionally substituted with Ar or $Het^1$; Ar; $Het^1$; $Het^2$; and a 7- to 10-membered saturated spirocarbobicyclic system; or $R^{4C}$ and $R^{4CC}$, or $R^{6C}$ and $R^{6CC}$ together with the nitrogen atom to which they are attached, form a N-linked $Het^2$; or (d) L is selected from —$N(R^D)$—$CR^{1D}R^{DD}$— and —$N(R^D)$—$CR^DR^{DD}$—$CR^{2D}R^{2DD}$—; wherein $R^D$ is selected from the group consisting of hydrogen; $C_{1-4}$alkyl optionally substituted with a substituent selected from the group consisting of fluoro and —CN; and $C_{2-4}$alkyl substituted with a substituent selected from —$OR^{1d}$ and —$NR^{2d}R^{2dd}$; wherein $R^{1d}$, $R^{2d}$ and $R^{2dd}$ are each independently selected from the group consisting of hydrogen and $C_{1-4}$alkyl;

$R^{1D}$, $R^{1DD}$, $R^{2D}$ and $R^{2DD}$ are each independently selected from the group consisting of hydrogen and $C_{1-4}$alkyl; and $R^3$ is selected from the group consisting of

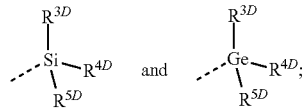

wherein $R^{3D}$, $R^{4D}$, and $R^{5D}$ are each independently selected from the group consisting of $C_{1-6}$alkyl optionally substituted with a —OH, —$OC_{1-6}$alkyl, or a —$NH_2$ substituent; or (e) -L-$R^3$ is

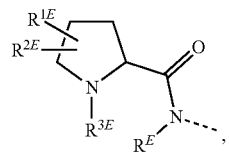

wherein $R^E$ is selected from the group consisting of hydrogen and $C_{1-4}$alkyl;

$R^{1E}$ is selected from the group consisting of hydrogen, fluoro and $C_{1-4}$alkyl; and $R^{2E}$ is selected from the group consisting of fluoro, —$OC_{1-4}$alkyl, and $C_{1-4}$alkyl optionally substituted with 1, 2 or 3 fluoro substituents; or $R^{1E}$ and $R^{2E}$ are bound to the same carbon atom and together form a $C_{3-5}$cycloalkyl or a C-linked 4- to 6-membered heterocyclyl containing an oxygen atom; and $R^{3E}$ is selected from the group consisting of hydrogen; $C_{1-4}$alkyl optionally substituted with a fluoro or a —CN substituent; and $C_{2-4}$alkyl substituted with a substituent selected from the group consisting of —$OR^{4E}$ and —$NR^{5E}R^{5EE}$; wherein $R^{4E}$, $R^{5E}$ and $R^{5EE}$ are each independently selected from the group consisting of hydrogen; $C_{1-4}$alkyl optionally substituted with a substituent selected from the group consisting of fluoro, —CN, and —$C(=O)NR^{6E}R^{6EE}$; $C_{2-4}$alkyl substituted with a substituent selected from the group consisting of —$OR^{7E}$ and —$NR^ER^{EE}$; and C-linked 4- to 7-membered non-aromatic heterocyclyl containing at least one nitrogen, oxygen or sulfur atom; wherein $R^{6E}$, $R^{6EE}$, $R^{7E}$, $R^{8E}$ and $R^{5EE}$ are each independently selected from the group consisting of hydrogen and $C_{1-4}$alkyl;

and wherein

Ar is phenyl optionally substituted with one, two, or three substituents each independently selected from the group consisting of halo, —CN, —$OR^4$, —$NR^5R^{5'}$, —$C(=O)NR^5R^{5'}$, and $C_{1-4}$alkyl optionally substituted with a substituent selected from the group consisting of fluoro, —CN, —$OR^6$, —$NR^7R^{7'}$, and —$C(=O)NR^8R^{8'}$;

$Het^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —$OR^4$, —$NR^5R^{5'}$, and $C_{1-4}$alkyl optionally substituted with a substituent selected from the group consisting of fluoro, —CN, —$OR^6$, —$NR^7R^{7'}$, and —$C(=O)NR^8R^{8'}$; and $Het^2$ is a non-aromatic heterocyclyl optionally substituted with one, two, or three substituents each independently selected from the group consisting of halo, —CN, —$OR^4$, —$NR^5R^{5'}$, and $C_{1-4}$alkyl optionally substituted with a substituent selected from the group consisting of fluoro, —CN, —$OR^6$, —$NR^7R^{7'}$, and —$C(=O)NR^8R^{8'}$;

wherein $R^4$, $R^5$, $R^{5'}$, $R^6$, $R^7$, $R^{7'}$, $R^8$ and $R^{8'}$ are each independently selected from the group consisting of hydrogen; $C_{1-4}$alkyl optionally substituted with a substituent selected from the group consisting of fluoro and —$C(=O)NR^9R^{9'}$; and $C_{2-4}$alkyl substituted with a substituent selected from the group consisting of —$OR^{10}$ and —$NR^{11}R^{11'}$; wherein $R^9$, $R^{9'}$, $R^{10}$, $R^{11}$ and $R^{11'}$ are each independently selected from the group consisting of hydrogen; $C_{1-4}$alkyl; and C-linked 4- to 7-membered non-aromatic heterocyclyl containing at least one nitrogen, oxygen or sulfur atom;

and the pharmaceutically acceptable salts and the solvates thereof.

The present invention relates in particular to compounds of Formula (I) as defined herein, and the tautomers and the stereoisomeric forms thereof, wherein $R^1$ is $CF_3$;

$R^2$ is hydrogen;

$Y^1$ is hydrogen;

$Y^2$ and $Y^3$ are each independently selected from the group consisting of hydrogen and $C_{1-6}$alkyl;

-L-$R^3$ is selected from (a), (b), (c), (e), or (f):

(a) -L-$R^3$ is —NHR$^{1A}$, wherein $R^{1A}$ is selected from the group consisting of $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$, wherein $R^{1a}$, $R^{2a}$ and $R^{2aa}$ are each independently selected from the group consisting of hydrogen and $C_{1-4}$alkyl; or (b) L is selected from the group consisting of —O—, —O—CR$^{1B}$R$^{1BB}$—, —N(R$^B$)—, and —N(R$^B$)—CR$^{1B}$R$^{1BB}$—; and $R^3$ is selected from the group consisting of Ar; Het$^1$; and Het$^2$; wherein R$^B$ is selected from the group consisting of hydrogen; $C_{1-4}$alkyl optionally substituted with a phenyl; and $C_{2-4}$alkyl substituted with a substituent selected from the group consisting of —OR$^{1b}$ and —NR$^{2b}$R$^{2bb}$; wherein
R$^{1b}$, R$^{2b}$, and R$^{2bb}$ are each independently selected from the group consisting of hydrogen, and $C_{1-4}$alkyl;

R$^{1B}$ is selected from the group consisting of hydrogen and $C_{1-4}$alkyl; and R$^{1BB}$ is hydrogen; or (c) -L-$R^3$ is selected from the group consisting of —N(R$^C$)—CHR$^{3C}$—CONR$^{4C}$R$^{4CC}$; and —N(R$^C$)—COR$^{5C}$; wherein R$^C$ is hydrogen;
R$^{3C}$ is $C_{1-4}$alkyl;
R$^{4C}$ is hydrogen;
R$^{5C}$ is Het$^2$; and
R$^{4CC}$ is $C_{1-4}$alkyl; or (e) -L-$R^3$ is

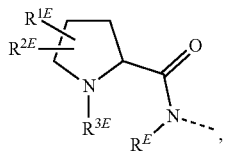

wherein
R$^E$ is hydrogen;
R$^{1E}$ and R$^{2E}$ are bound to the same carbon atom and together form a $C_{3-5}$cycloalkyl; and
R$^{3E}$ is hydrogen; or (f) -L-$R^3$ is a radical selected from the group consisting of

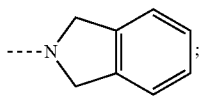

and wherein
Ar is phenyl optionally substituted with one, two, or three substituents each independently selected from the group consisting of halo, —OR$^4$, —C(=O)NR$^5$R$^{5'}$, and $C_{1-4}$alkyl optionally substituted with a substituent selected from the group consisting of —OR$^6$, and —NR$^7$R$^{7'}$;

Het$^1$ is a monocyclic heteroaryl selected from the group consisting of pyridyl, 4-, 5- or 6-pyrimidinyl, pyridazinyl, and pyrazolyl; each of which may be optionally substituted with one, two, or three substituents each independently selected from $C_{1-4}$alkyl optionally substituted with a —OR$^6$ substituent; and Het$^2$ is a non-aromatic heterocyclyl optionally substituted with one, two, or three $C_{1-4}$alkyl substituents;

wherein
R$^4$, R$^5$, R$^{5'}$, R$^6$, R$^7$, and R$^{7'}$ are each independently selected from the group consisting of hydrogen and $C_{1-4}$alkyl;

and the pharmaceutically acceptable salts and the solvates thereof.

The present invention relates in particular to compounds of Formula (I) as defined herein, and the tautomers and the stereoisomeric forms thereof, wherein $R^1$ is CF$_3$;
$R^2$ is hydrogen;
$Y^1$ is hydrogen;
$Y^2$ and $Y^3$ are each independently selected from the group consisting of hydrogen and $C_{1-6}$alkyl;

-L-$R^3$ is selected from (a), (b), (c), (e), or (f):

(a) -L-$R^3$ is —NHR$^{1A}$, wherein $R^{1A}$ is selected from the group consisting of $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$, wherein $R^{1a}$, $R^{2a}$ and $R^{2aa}$ are each independently selected from the group consisting of hydrogen and $C_{1-4}$alkyl; or (b) L is selected from the group consisting of —N(R$^B$)—, and —N(R$^B$)—CR$^{1B}$R$^{BB}$—; and $R^3$ is selected from the group consisting of Ar; Het$^1$; and Het$^2$; wherein R$^B$ is selected from the group consisting of hydrogen; $C_{1-4}$alkyl optionally substituted with a phenyl; and $C_{2-4}$alkyl substituted with a substituent selected from the group consisting of —OR$^{1b}$ and —NR$^{2b}$R$^{2bb}$; wherein
R$^{1b}$, R$^{2b}$, and R$^{2bb}$ are each independently selected from the group consisting of hydrogen, and $C_{1-4}$alkyl;

R$^{1B}$ is selected from the group consisting of hydrogen and $C_{1-4}$alkyl; and R$^{1BB}$ is hydrogen; or (c) -L-$R^3$ is selected from the group consisting of —N(R$^C$)—CHR$^{3C}$—CONR$^{4C}$R$^{4CC}$; and —N(R$^C$)—COR$^5$C; wherein R$^C$ is hydrogen;
R$^{3C}$ is $C_{1-4}$alkyl;
R$^{4C}$ is hydrogen;
R$^{5C}$ is Het$^2$; and
R$^{4CC}$ is $C_{1-4}$alkyl; or (e) -L-$R^3$ is

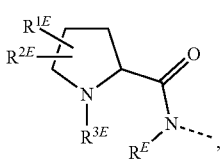

wherein
R$^E$ is hydrogen;
R$^{1E}$ and R$^{2E}$ are bound to the same carbon atom and together form a $C_{3-5}$cycloalkyl; and
R$^{3E}$ is hydrogen;

and wherein
Ar is phenyl optionally substituted with one, two, or three substituents each independently selected from the group consisting of halo, —$OR^4$, —C(=O)$NR^5R^{5'}$, and $C_{1-4}$alkyl optionally substituted with a substituent selected from the group consisting of —$OR^6$, and —$NR^7R^{7'}$;
$Het^1$ is a monocyclic heteroaryl selected from the group consisting of pyridyl, 4-, 5- or 6-pyrimidinyl, pyridazinyl, and pyrazolyl; each of which may be optionally substituted with one, two, or three substituents each independently selected from $C_{1-4}$alkyl optionally substituted with a —$OR^6$ substituent; and
$Het^2$ is a non-aromatic heterocyclyl optionally substituted with one, two, or three $C_{1-4}$alkyl substituents; wherein
$R^4$, $R^5$, $R^{5'}$, $R^6$, $R^7$, and $R^{7'}$ are each independently selected from the group consisting of hydrogen and $C_{1-4}$alkyl;
and the pharmaceutically acceptable salts and the solvates thereof.

The present invention relates in particular to compounds of Formula (I) as defined herein, and the tautomers and the stereoisomeric forms thereof, wherein
$R^1$ is $CF_3$;
$R^2$ is hydrogen;
$Y^1$ is hydrogen;
$Y^2$ and $Y^3$ are hydrogen;
-L-$R^3$ is selected from (a) or (b):
(a) -L-$R^3$ is —$NHR^{1A}$, wherein $R^{1A}$ is $C_{1-6}$alkyl; or
(b) L is —N($R^B$)—$CR^{1B}R^{1BB}$—;
and $R^3$ is selected from the group consisting of Ar; $Het^1$; and $Het^2$; wherein
$R^B$ is hydrogen;
$R^{1B}$ is selected from the group consisting of hydrogen and $C_{1-4}$alkyl; and
$R^{1BB}$ is hydrogen;
and wherein
Ar is phenyl optionally substituted with one $C_{1-4}$alkyl;
$Het^1$ is pyrazolyl; and
$Het^2$ is a non-aromatic heterocyclyl; in particular 3-azetidinyl;
and the pharmaceutically acceptable salts and the solvates thereof.

The present invention relates in particular to compounds of Formula (I) as defined herein, and the tautomers and the stereoisomeric forms thereof, wherein
$R^1$ is selected from the group consisting of $CH_3$, $CH_2F$, $CHF_2$ and $CF_3$;
$R^2$ is selected from the group consisting of hydrogen and $CH_3$;
$Y^1$ is selected from the group consisting of hydrogen; $C_{1-6}$alkyl; C-linked 4- to 7-membered non-aromatic heterocyclyl containing at least one nitrogen atom optionally substituted with a $C_{1-4}$alkyl or cyclopropyl substituent; and $C_{1-4}$alkyl substituted with a substituent selected from the group consisting of phenyl, —$OR^{1Y}$, and —$NR^{2Y}R^{2YY}$; wherein
$R^{1Y}$, $R^{2Y}$ and $R^{2YY}$ are each independently selected from the group consisting of hydrogen and $C_{1-4}$alkyl;
$Y^2$ and $Y^3$ are hydrogen; and
-L-$R^3$ is selected from (a), (b), (c), (e), or (f):
(a) -L-$R^3$ is —$NHR^{1A}$, wherein $R^{1A}$ is selected from the group consisting of hydrogen; $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$ and $R^{2aa}$ are each independently selected from the group consisting of hydrogen, $C_{1-4}$alkyl and cyclopropyl; or
(b) L is selected from the group consisting of —N($R^B$)—, —N($R^B$)—$CR^{1B}R^{1BB}$—, and —(N$R^B$)—$CHR^{1B}$—$CHR^{2B}$—; and $R^3$ is selected from the group consisting of Ar; $Het^1$; and $Het^2$; wherein
$R^B$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —$OR^{1b}$ and —$NR^{2b}R^{2bb}$; wherein
$R^{1b}$, $R^{2b}$, and $R^{2bb}$ are each independently selected from the group consisting of hydrogen, $C_{1-4}$alkyl and cyclopropyl;
$R^{1B}$ is selected from the group consisting of hydrogen; $C_{1-4}$alkyl optionally substituted with a phenyl or a $Het^1$ substituent; and $C_{2-4}$alkyl substituted with a substituent selected from the group consisting of —OH and —$NH_2$; and $R^{1BB}$ is hydrogen; or $R^{1B}$ and $R^{1BB}$ together with the carbon to which they are attached form an oxetanyl ring; and
$R^{2B}$ is hydrogen; or
(c) -L-$R^3$ is selected from the group consisting of —N($R^C$)—$CHR^{3C}$—$CONR^{4C}R^{4CC}$; —N($R^C$)—$COR^{5C}$; —N($R^C$)—$SO_2$—$NR^{6C}R^{6CC}$; wherein
$R^C$ is selected from the group consisting of hydrogen; and $C_{1-4}$alkyl optionally substituted with a phenyl substituent;
$R^{3C}$ is hydrogen or $C_{1-4}$alkyl;
$R^{4C}$ and $R^{6C}$ are each selected from the group consisting of hydrogen and $C_{1-4}$alkyl;
$R^{5C}$ is $C_{1-4}$alkyl optionally substituted with —$NR^{2c}R^{2cc}$; wherein $R^{2c}$ and $R^{2cc}$ are each independently selected from the group consisting of hydrogen and $C_{1-4}$alkyl; and
$R^{4CC}$ and $R^{6CC}$ are each independently selected from the group consisting of hydrogen and $C_{1-4}$alkyl; or $R^{4C}$ and $R^{4CC}$, or $R^{6C}$ and $R^{6CC}$ together with the nitrogen atom to which they are attached, form a N-linked $Het^2$; or
(e) -L-$R^3$ is

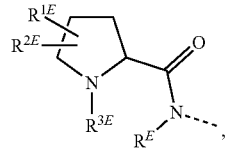

wherein
$R^E$ is selected from the group consisting of hydrogen and $C_{1-4}$alkyl;
$R^{1E}$ is selected from the group consisting of hydrogen, fluoro and $C_{1-4}$alkyl; and
$R^{2E}$ is selected from the group consisting of fluoro, —$OC_{1-4}$alkyl, and $C_{1-4}$alkyl optionally substituted with 1, 2 or 3 fluoro substituents; or $R^{1E}$ and $R^{2E}$ are bound to the same carbon atom and together form a $C_{3-5}$cycloalkyl; and
$R^{3E}$ is selected from the group consisting of hydrogen and $C_{1-4}$alkyl; or
(f) -L-$R^3$ is a radical selected from the group consisting of

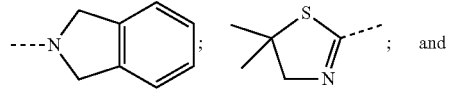

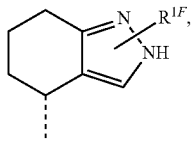

wherein $R^{1F}$ is hydrogen or $C_{1-4}$alkyl;
and wherein
Ar is phenyl optionally substituted with one, two, or three substituents each independently selected from the group consisting of halo, —C(=O)NR$^5$R$^{5'}$, and $C_{1-4}$alkyl; wherein $R^5$ and $R^{5'}$ are each independently selected from the group consisting of hydrogen and $C_{1-4}$alkyl;
Het$^1$ is a monocyclic heteroaryl selected from the group consisting of pyridyl, 4-, 5- or 6-pyrimidinyl, pyrazinyl, pyridazinyl, pyrrolyl, pyrazolyl, and imidazolyl; each of which may be optionally substituted with one, two, or three substituents each independently selected from the group consisting of halo and $C_{1-4}$alkyl; and Het$^2$ is a non-aromatic heterocyclyl selected from azetidinyl, pyrrolidinyl and piperidinyl, each of which may be optionally substituted with one, two, or three substituents each independently selected from the group consisting of halo and $C_{1-4}$alkyl;
and the pharmaceutically acceptable salts and the solvates thereof.

The present invention relates in particular to compounds of Formula (I) as defined herein, and the tautomers and the stereoisomeric forms thereof, wherein
$R^1$ is $CF_3$;
$R^2$ is hydrogen;
$Y^1$ is selected from the group consisting of hydrogen; $C_{1-6}$alkyl; C-linked 4- to 7-membered non-aromatic heterocyclyl containing at least one nitrogen atom optionally substituted with a $C_{1-4}$alkyl substituent; and $C_{1-4}$alkyl substituted with a substituent selected from the group consisting of phenyl, —OH and —OC$_{1-4}$alkyl;
$Y^2$ and $Y^3$ are hydrogen; and
-L-R$^3$ is selected from (a), (b), (c), (e), or (f):
(a) -L-R$^3$ is —NHR$^{1A}$, wherein R$^{1A}$ is selected from the group consisting of hydrogen; $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$, wherein R$^{1a}$, R$^{2a}$ and R$^{2aa}$ are each independently selected from the group consisting of hydrogen, $C_{1-4}$alkyl and cyclopropyl; or
(b) L is selected from the group consisting of —N(R$^B$)— and —N(R$^B$)—CR$^{1B}$R$^{1BB}$—; and R$^3$ is selected from the group consisting of Ar; Het$^1$; and Het$^2$; wherein
  R$^B$ is selected from the group consisting of hydrogen; $C_{1-4}$alkyl optionally substituted with a phenyl or a —CN substituent; and $C_{2-4}$alkyl substituted with a substituent selected from the group consisting of —OR$^{1b}$ and —NR$^{2b}$R$^{2bb}$; wherein
    R$^{1b}$, R$^{2b}$, and R$^{2bb}$ are each independently selected from the group consisting of hydrogen and $C_{1-4}$alkyl;
  R$^{1B}$ is selected from the group consisting of hydrogen; $C_{1-4}$alkyl optionally substituted with a phenyl or a Het$^1$ substituent; and $C_{2-4}$alkyl substituted with a —OH substituent; and R$^{1BB}$ is hydrogen; or R$^{1B}$ and R$^{1BB}$ together with the carbon to which they are attached form an oxetanyl ring; or
(c) -L-R$^3$ is selected from the group consisting of —N(R$^C$)—CHR$^{3C}$—CONR$^{4C}$R$^{4CC}$; —N(R$^C$)—COR$^{5C}$; and —N(R$^C$)—SO$_2$—NR$^{6C}$R$^{6CC}$; wherein R$^C$ is selected from the group consisting of hydrogen; and $C_{1-4}$alkyl optionally substituted with a phenyl substituent;
R$^{3C}$, R$^{4C}$ and R$^{6C}$ are each selected from the group consisting of hydrogen and $C_{1-4}$alkyl;
R$^{5C}$ is $C_{1-4}$alkyl optionally substituted with —NR$^{2c}$R$^{2cc}$; wherein R$^{2c}$ and R$^{2cc}$ are each independently selected from the group consisting of hydrogen and $C_{1-4}$alkyl; and
R$^{4CC}$ and R$^{6CC}$ are each independently selected from the group consisting of hydrogen and $C_{1-4}$alkyl; or
(e) -L-R$^3$ is

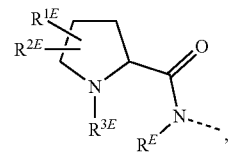

wherein
  R$^E$ is selected from the group consisting of hydrogen and methyl;
  R$^{1E}$ and R$^{2E}$ are each an independently selected $C_{1-4}$alkyl substituent; or R$^{1E}$ and
  R$^{2E}$ are bound to the same carbon atom and together form a $C_{3-5}$cycloalkyl; and
  R$^{3E}$ is hydrogen; or
(f) -L-R$^3$ is

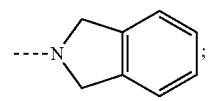

and wherein
Ar is phenyl optionally substituted with one or two substituents each independently selected from the group consisting of halo, —C(=O)NR$^5$R$^{5'}$, and $C_{1-4}$alkyl; wherein R$^5$ and R$^{5'}$ are each independently selected from the group consisting of hydrogen and $C_{1-4}$alkyl;
Het$^1$ is a monocyclic heteroaryl selected from the group consisting of pyridyl, 4-, 5- or 6-pyrimidinyl, pyrazinyl, pyridazinyl, pyrrolyl, pyrazolyl, and imidazolyl; each of which may be optionally substituted with one or two substituents each independently selected from the group consisting of halo and $C_{1-4}$alkyl; and
Het$^2$ is a non-aromatic heterocyclyl selected from azetidinyl, pyrrolidinyl and piperidinyl, each of which may be optionally substituted with a $C_{1-4}$alkyl substituent;
and the pharmaceutically acceptable salts and the solvates thereof.

The present invention relates in particular to compounds of Formula (I) as defined herein, and the tautomers and the stereoisomeric forms thereof, wherein
$R^1$ is $CF_3$;
$R^2$ is hydrogen;
$Y^1$, $Y^2$ and $Y^3$ are hydrogen; and
-L-R$^3$ is selected from (a), (b), (c), (e), or (f):
(a) -L-R$^3$ is —NHR$^{1A}$, wherein R$^{1A}$ is selected from the group consisting of $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$; wherein R$^{1a}$, R$^{2a}$ and R$^{2aa}$ are each independently selected from the group consisting of hydrogen, $C_{1-4}$alkyl and cyclopropyl; or (b) L is —N(R$^B$)—CR$^{1B}$R$^{1BB}$— and R$^3$ is selected from the group consisting of Ar and Het$^1$; wherein
  R$^B$ is selected from the group consisting of hydrogen; C$_{1-4}$alkyl optionally substituted with a phenyl or a —CN substituent; and C$_{2-4}$alkyl substituted with a substituent selected from the group consisting of —OR$^{1b}$ and —NR$^{2b}$R$^{2bb}$; wherein
    R$^{1b}$, R$^{2b}$, and R$^{2bb}$ are each independently selected from the group consisting of hydrogen and C$_{1-4}$alkyl;
  R$^{1B}$ is selected from the group consisting of hydrogen; C$_{1-4}$alkyl optionally substituted with a Het$^1$ substituent; and C$_{2-4}$alkyl substituted with a —OH substituent; and R$^{1BB}$ is hydrogen; or R$^{1B}$ and R$^{1BB}$ together with the carbon to which they are attached form an oxetanyl ring; or
(c) -L-R$^3$ is selected from the group consisting of —N(R$^C$)—CHR$^{3C}$—CONR$^{4C}$R$^{4CC}$; —N(R$^C$)—COR$^{5C}$; and —N(R$^C$)—SO$_2$—NR$^{6C}$R$^{6CC}$; wherein
  R$^C$ is selected from the group consisting of hydrogen; and C$_{1-4}$alkyl optionally substituted with a phenyl substituent;
  R$^{3C}$, R$^{4C}$ and R$^{6C}$ are each selected from the group consisting of hydrogen and C$_{1-4}$alkyl;
  R$^{5C}$ is C$_{1-4}$alkyl optionally substituted with —NR$^{2c}$R$^{2cc}$; wherein R$^{2c}$ and R$^{2cc}$ are each independently selected from the group consisting of hydrogen and C$_{1-4}$alkyl; and
  R$^{4CC}$ and R$^{6CC}$ are each independently selected from the group consisting of hydrogen and C$_{1-4}$alkyl; or
(e) -L-R$^3$ is

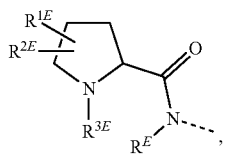

wherein
  R$^E$ is selected from the group consisting of hydrogen and methyl;
  R$^{1E}$ and R$^{2E}$ are each an independently selected C$_{1-4}$alkyl substituent; or R$^{1E}$ and R$^{2E}$ are bound to the same carbon atom and together form a C$_{3-5}$cycloalkyl; and
  R$^{3E}$ is hydrogen; or
(f) -L-R$^3$ is

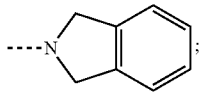

and wherein
Ar is phenyl optionally substituted with one or two substituents each independently selected from the group consisting of halo, —C(=O)NR$^5$R$^{5'}$, and C$_{1-4}$alkyl; wherein R$^5$ and R$^{5'}$ are each independently selected from the group consisting of hydrogen and C$_{1-4}$alkyl; and
Het$^1$ is a monocyclic heteroaryl selected from the group consisting of pyridyl, 4-, 5- or 6-pyrimidinyl, pyrazinyl, pyridazinyl, pyrrolyl, pyrazolyl, and imidazolyl; each of which may be optionally substituted with one or two substituents each independently selected from the group consisting of halo and C$_{1-4}$alkyl;
and the pharmaceutically acceptable salts and the solvates thereof.

Another embodiment of the present invention relates to those compounds of Formula (I) and the pharmaceutically acceptable salts, and the solvates thereof, or any subgroup thereof as mentioned in any of the other embodiments wherein
R$^1$ is CF$_3$;
R$^2$ is hydrogen;
Y$^1$ is hydrogen;
Y$^2$ and Y$^3$ are each independently selected from the group consisting of hydrogen and C$_{1-6}$alkyl.

In an embodiment, the present invention relates to those compounds of Formula (I) and the pharmaceutically acceptable salts, and the solvates thereof, or any subgroup thereof as mentioned in any of the other embodiments, wherein
-L-R$^3$ is selected from (a), (b), (c), (d), or (e).

In an embodiment, the present invention relates to those compounds of Formula (I) and the pharmaceutically acceptable salts, and the solvates thereof, or any subgroup thereof as mentioned in any of the other embodiments, wherein
-L-R$^3$ is (a).

In an embodiment, the present invention relates to those compounds of Formula (I) and the pharmaceutically acceptable salts, and the solvates thereof, or any subgroup thereof as mentioned in any of the other embodiments, wherein
-L-R$^3$ is (b).

In an embodiment, the present invention relates to those compounds of Formula (I) and the pharmaceutically acceptable salts, and the solvates thereof, or any subgroup thereof as mentioned in any of the other embodiments, wherein
-L-R$^3$ is (C).

In an embodiment, the present invention relates to those compounds of Formula (I) and the pharmaceutically acceptable salts, and the solvates thereof, or any subgroup thereof as mentioned in any of the other embodiments, wherein-L-R$^3$ is (d).

In an embodiment, the present invention relates to those compounds of Formula (I) and the pharmaceutically acceptable salts, and the solvates thereof, or any subgroup thereof as mentioned in any of the other embodiments, wherein
-L-R$^3$ is (e).

In an embodiment, the present invention relates to those compounds of Formula (I) and the pharmaceutically acceptable salts, and the solvates thereof, or any subgroup thereof as mentioned in any of the other embodiments, wherein
-L-R$^3$ is (f).

In an embodiment, the present invention relates to those compounds of Formula (I) and the pharmaceutically acceptable salts, and the solvates thereof, or any subgroup thereof as mentioned in any of the other embodiments, wherein
-L-R$^3$ is selected from (a), (b), (c), (d), or (e); wherein (a), (c), (d) and (e) are defined according to any one of the other embodiments; and wherein (b) is defined as
(b) L is selected from the group consisting of —N(R$^B$)—, —N(R$^B$)—CR$^{1B}$R$^{1BB}$—, and —(NR$^B$)—CHR$^{1B}$—CHR$^{2B}$—; and R$^3$ is selected from the group consisting of Ar; Het$^1$; Het$^2$; and a 7- to 10-membered saturated spiro-carbobicyclic system; wherein
  R$^B$ is selected from the group consisting of hydrogen; C$_{1-4}$alkyl optionally substituted with a substituent selected from the group consisting of fluoro, phenyl and —CN; and C$_{2-4}$alkyl substituted with a substituent selected from the group consisting of —OR$^{1b}$ and —NR$^{2b}$R$^{2bb}$; wherein
    R$^{1b}$, R$^{2b}$, and R$^{2bb}$ are each independently selected from the group consisting of hydrogen, C$_{1-4}$alkyl and cyclopropyl;

$R^{1B}$ is selected from the group consisting of hydrogen; —C(=O)NR$^{3B}$R$^{3BB}$; C$_{1-4}$alkyl optionally substituted with a substituent selected from the group consisting of fluoro, phenyl, Het$^1$, and —CN; C$_{2-4}$alkyl substituted with a substituent selected from the group consisting of —OR$^{4B}$ and —NR$^{5B}$R$^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a C-linked 4- to 7-membered non-aromatic heterocyclyl containing at least one nitrogen, oxygen or sulfur atom;

$R^{2B}$ is selected from the group consisting of hydrogen; —OR$^{6B}$; —NR$^{7B}$R$^{7BB}$; —C(=O)NR$^{8B}$R$^{8BB}$; C$_{1-4}$alkyl optionally substituted with a substituent selected from the group consisting of fluoro, —CN, —OR$^{4B}$, and —NR$^{5B}$R$^{5BB}$; and C-linked 4- to 7-membered non-aromatic heterocyclyl containing at least one nitrogen, oxygen or sulfur atom; wherein $R^{3B}$, $R^{3BB}$, $R^{4B}$, $R^{5B}$, $R^{5BB}$, $R^{6B}$, $R^{7B}$, $R^{7BB}$, $R^{8B}$ and $R^{8BB}$ are each independently selected from the group consisting of hydrogen; C$_{1-4}$alkyl optionally substituted with a substituent selected from the group consisting of fluoro, —CN and —C(=O)NR$^{9B}$R$^{9BB}$; and C$_{2-4}$alkyl substituted with a substituent selected from the group consisting of —OR$^{10B}$ and —NR$^{11B}$R$^{11BB}$; wherein $R^{9B}$, $R^{9BB}$, $R^{10B}$, $R^{11B}$ and $R^{11BB}$ are each independently selected from the group consisting of hydrogen; C$_{1-4}$alkyl; and C-linked 4- to 7-membered non-aromatic heterocyclyl containing at least one nitrogen, oxygen or sulfur atom.

In an embodiment, the present invention relates to those compounds of Formula (I) and the pharmaceutically acceptable salts, and the solvates thereof, or any subgroup thereof as mentioned in any of the other embodiments, wherein -L-R$^3$ is selected from (a), (b), (c), (d), or (e); and provided that L in option (b) is not —O— or —O—CR$^{1B}$R$^{1BB}$—.

In an embodiment, the present invention relates to those compounds of Formula (I) and the pharmaceutically acceptable salts, and the solvates thereof, or any subgroup thereof as mentioned in any of the other embodiments, wherein -L-R$^3$ is selected from (a), (b), (c), (d), (e) or (f); wherein (a), (c), (d) and (e) are defined according to any one of the other embodiments;
wherein (b) is defined as
(b) L is selected from the group consisting of —N(R$^B$)—, —N(R$^B$)—CR$^{1B}$R$^{1BB}$—, and —(NR$^B$)—CHR$^{1B}$—CHR$^{2B}$—; and R$^3$ is selected from the group consisting of Ar; Het$^1$; Het$^2$; and a 7- to 10-membered saturated spiro-carbobicyclic system; wherein $R^B$ is selected from the group consisting of hydrogen; C$_{1-4}$alkyl optionally substituted with a substituent selected from the group consisting of fluoro, phenyl and —CN; and C$_{2-4}$alkyl substituted with a substituent selected from the group consisting of —OR$^{1b}$ and —NR$^{2b}$R$^{2bb}$; wherein $R^{1b}$, $R^{2b}$, and $R^{2bb}$ are each independently selected from the group consisting of hydrogen, C$_{1-4}$alkyl and cyclopropyl;

$R^{1B}$ is selected from the group consisting of hydrogen; —C(=O)NR$^{3B}$R$^{3BB}$; C$_{1-4}$alkyl optionally substituted with a substituent selected from the group consisting of fluoro, phenyl, Het$^1$, and —CN; C$_{2-4}$alkyl substituted with a substituent selected from the group consisting of —OR$^{4B}$ and —NR$^{5B}$R$^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a C-linked 4- to 7-membered non-aromatic heterocyclyl containing at least one nitrogen, oxygen or sulfur atom;

$R^{2B}$ is selected from the group consisting of hydrogen; —OR$^{6B}$; —NR$^{7B}$R$^{7BB}$; —C(=O)NR$^{8B}$R$^{8BB}$; C$_{1-4}$alkyl optionally substituted with a substituent selected from the group consisting of fluoro, —CN, —OR$^{4B}$, and —NR$^{5B}$R$^{5BB}$; and C-linked 4- to 7-membered non-aromatic heterocyclyl containing at least one nitrogen, oxygen or sulfur atom; wherein $R^{3B}$, $R^{3BB}$, $R^{4B}$, $R^{5B}$, $R^{5BB}$, $R^{6B}$, $R^{7B}$, $R^{7BB}$, $R^{8B}$ and $R^{8BB}$ are each independently selected from the group consisting of hydrogen; C$_{1-4}$alkyl optionally substituted with a substituent selected from the group consisting of fluoro, —CN and —C(=O)NR$^{9B}$R$^{9BB}$; and C$_{2-4}$alkyl substituted with a substituent selected from the group consisting of —OR$^{10B}$ and —NR$^{11B}$R$^{11BB}$; wherein $R^{9B}$, $R^{9BB}$, $R^{10B}$, $R^{11B}$ and $R^{11BB}$ are each independently selected from the group consisting of hydrogen; C$_{1-4}$alkyl; and C-linked 4- to 7-membered non-aromatic heterocyclyl containing at least one nitrogen, oxygen or sulfur atom; and
wherein (f) is defined as
(f) -L-R$^3$ is a radical selected from the group consisting of

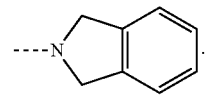

In an embodiment, the present invention relates to those compounds of Formula (I) and the pharmaceutically acceptable salts, and the solvates thereof, or any subgroup thereof as mentioned in any of the other embodiments, wherein -L-R$^3$ is selected from (a), (b), (c), (d), (e) or (f); wherein (a), (b), (c), (d) and (e) are defined according to any one of the other embodiments;
wherein (f) is defined as
(f) -L-R$^3$ is a radical selected from the group consisting of

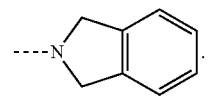

Another embodiment of the present invention relates to those compounds of Formula (I) and the pharmaceutically acceptable salts, and the solvates thereof, or any subgroup thereof as mentioned in any of the other embodiments wherein one or more of the following restrictions apply:
(i) R$^1$ is CF$_3$;
(ii) R$^2$ is hydrogen;
(iii) Y$^1$ is hydrogen;
(iv) Y$^2$ and Y$^3$ are hydrogen;
(v) -L-R$^3$ is selected from (a) or (b):
 (a) -L-R$^3$ is —NHR$^{1A}$, wherein R$^{1A}$ is C$_{1-6}$alkyl; or
 (b) L is —N(R$^B$)—CR$^{1B}$R$^{BB}$—;
and R$^3$ is selected from the group consisting of Ar; Het$^1$; and Het$^2$;
(vi) R$^B$ is hydrogen;

(vii) $R^{1B}$ is selected from the group consisting of hydrogen and $C_{1-4}$alkyl; and
(viii) $R^{1BB}$ is hydrogen;
(ix) Ar is phenyl optionally substituted with one $C_{1-4}$alkyl;
(x) $Het^1$ is pyrazolyl;
(xi) $Het^2$ is a non-aromatic heterocyclyl; in particular 3-azetidinyl.

Another embodiment of the present invention relates to those compounds of Formula (I) and the pharmaceutically acceptable salts, and the solvates thereof, or any subgroup thereof as mentioned in any of the other embodiments wherein one or more of the following restrictions apply:
(i) $R^1$ is $CF_3$;
(ii) $R^2$ is hydrogen;
(iii) $Y^1$, $Y^2$ and $Y^3$ are hydrogen;
(iv) -L-$R^3$ is selected from (a), (b), (c) or (e):
  (a) -L-$R^3$ is —$NHR^{1A}$, wherein $R^{1A}$ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$ and $R^{2aa}$ are each independently selected from the group consisting of hydrogen, $C_{1-4}$alkyl and cyclopropyl; or
  (b) L is —$N(R^B)$—$CR^{1B}R^{1BB}$— and $R^3$ is selected from the group consisting of Ar and $Het^1$; wherein
    $R^B$ is selected from the group consisting of hydrogen; $C_{1-4}$alkyl optionally substituted with a phenyl or a —CN substituent; and $C_{2-4}$alkyl substituted with a substituent selected from the group consisting of —$OR^{1b}$ and —$NR^{2b}R^{2bb}$; wherein $R^{1b}$, $R^{2b}$, and $R^{2bb}$ are each independently selected from the group consisting of hydrogen and $C_{1-4}$alkyl;
    $R^{1B}$ is selected from the group consisting of hydrogen; $C_{1-4}$alkyl optionally substituted with a $Het^1$ substituent; and $C_{2-4}$alkyl substituted with a —OH substituent; and $R^{1BB}$ is hydrogen; or $R^{1B}$ and $R^{1BB}$ together with the carbon to which they are attached form an oxetanyl ring; or
  (c) -L-$R^3$ is selected from the group consisting of —$N(R^C)$—$CHR^{3C}$—$CONR^{4C}R^{4CC}$; —$N(R^C)$—$COR^{5C}$; and —$N(R^C)$—$SO_2$—$NR^{6C}R^{6CC}$; wherein
    $R^C$ is selected from the group consisting of hydrogen; and $C_{1-4}$alkyl optionally substituted with a phenyl substituent;
    $R^{3C}$, $R^{4C}$ and $R^{6C}$ are each selected from the group consisting of hydrogen and $C_{1-4}$alkyl;
    $R^{5C}$ is $C_{1-4}$alkyl optionally substituted with —$NR^{2c}R^{2cc}$; wherein $R^{2c}$ and $R^{2cc}$ are each independently selected from the group consisting of hydrogen and $C_{1-4}$alkyl; and
    $R^{4CC}$ and $R^{6CC}$ are each independently selected from the group consisting of hydrogen and $C_{1-4}$alkyl; or
  (e) -L-$R^3$ is wherein
  $R^E$ is selected from the group consisting of hydrogen and methyl;
  $R^{1E}$ and $R^{2E}$ are each an independently selected $C_{1-4}$alkyl substituent; or $R^{1E}$ and $R^{2E}$ are bound to the same carbon atom and together form a $C_{3-5}$cycloalkyl; and
  $R^{3E}$ is hydrogen;
(v) -L-$R^3$ is selected from (a), (b), (c) or (e):
  (a) -L-$R^3$ is —$NHR^{1A}$, wherein $R^{1A}$ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$ and $R^{2aa}$ are each independently selected from the group consisting of hydrogen, $C_{1-4}$alkyl and cyclopropyl; or
  (b) L is —NH—$CR^{1B}R^{1BB}$— and $R^3$ is selected from the group consisting of Ar and $Het^1$; wherein
    $R^{1B}$ is selected from the group consisting of hydrogen; $C_{1-4}$alkyl optionally substituted with a $Het^1$ substituent; and $C_{2-4}$alkyl substituted with a —OH substituent; and $R^{1BB}$ is hydrogen; or $R^{1B}$ and $R^{1BB}$ together with the carbon to which they are attached form an oxetanyl ring; or
  (c) -L-$R^3$ is selected from the group consisting of —$N(R^C)$—$CHR^{3C}$—$CONR^{4C}R^{4CC}$; —$N(R^C)$—$COR^{5C}$; and —$N(R^C)$—$SO_2$—$NR^{6C}R^{6CC}$; wherein
    $R^C$ is selected from the group consisting of hydrogen; and $C_{1-4}$alkyl optionally substituted with a phenyl substituent;
    $R^{3C}$, $R^{4C}$ and $R^{6C}$ are each selected from the group consisting of hydrogen and $C_{1-4}$alkyl;
    $R^{5C}$ is $C_{1-4}$alkyl optionally substituted with —$NR^{2c}R^{2cc}$; wherein $R^{2c}$ and $R^{2cc}$ are each independently selected from the group consisting of hydrogen and $C_{1-4}$alkyl; and
    $R^{4CC}$ and $R^{6CC}$ are each independently selected from the group consisting of hydrogen and $C_{1-4}$alkyl; or
  (e) -L-$R^3$ is wherein
  $R^E$ is selected from the group consisting of hydrogen and methyl;
  $R^{1E}$ and $R^{2E}$ are each an independently selected $C_{1-4}$alkyl substituent; or $R^{1E}$ and $R^{2E}$ are bound to the same carbon atom and together form a $C_{3-5}$cycloalkyl; and
  $R^{3E}$ is hydrogen;
(vi) -L-$R^3$ is selected from (a), (b), (c) or (e):
  (a) -L-$R^3$ is —$NHR^{1A}$, wherein $R^{1A}$ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$ and $R^{2aa}$ are each independently selected from the group consisting of hydrogen, $C_{1-4}$alkyl and cyclopropyl; or
  (b) L is —NH—$CR^{1B}R^{1BB}$— and $R^3$ is selected from the group consisting of Ar and $Het^1$; wherein $R^{1B}$ is selected from the group consisting of hydrogen; $C_{1-4}$alkyl optionally substituted with a Het$^1$ substituent; and $C_{2-4}$alkyl substituted with a —OH substituent; and $R^{1BB}$ is hydrogen; or (c) -L-$R^3$ is selected from the group consisting of —N($R^C$)—CHR$^{3C}$—CONR$^{4C}$R$^{4CC}$; —N($R^C$)—COR$^{5C}$; and —N($R^C$)—SO$_2$—NR$^{6C}$R$^{6CC}$; wherein $R^C$ is selected from the group consisting of hydrogen; and $C_{1-4}$alkyl optionally substituted with a phenyl substituent;

$R^{3C}$, $R^{4C}$ and $R^{6C}$ are each selected from the group consisting of hydrogen and $C_{1-4}$alkyl;

$R^{5C}$ is $C_{1-4}$alkyl optionally substituted with —NR$^{2C}$R$^{2CC}$; wherein $R^{2c}$ and $R^{2cc}$ are each independently selected from the group consisting of hydrogen and $C_{1-4}$alkyl; and $R^{4CC}$ and $R^{6CC}$ are each independently selected from the group consisting of hydrogen and $C_{1-4}$alkyl; or (e) -L-$R^3$ is

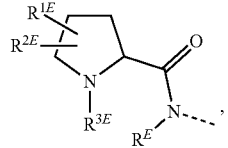

wherein
$R^E$ is selected from the group consisting of hydrogen and methyl;
$R^{1E}$ and $R^{2E}$ are each an independently selected $C_{1-4}$alkyl substituent; or $R^{1E}$ and
$R^{2E}$ are bound to the same carbon atom and together form a $C_{3-5}$cycloalkyl; and
$R^{3E}$ is hydrogen;

(vii) -L-$R^3$ is selected from (a), (b), or (e):
(a) -L-$R^3$ is —NHR$^{1A}$, wherein $R^{1A}$ is selected from the group consisting of $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$, wherein $R^{1a}$, $R^{2a}$ and $R^{2aa}$ are each independently selected from the group consisting of hydrogen, $C_{1-4}$alkyl and cyclopropyl; or
(b) L is —NH—CR$^{1B}$R$^{1BB}$— and $R^3$ is selected from the group consisting of Ar and Het$^1$; wherein
$R^{1B}$ is selected from the group consisting of hydrogen; $C_{1-4}$alkyl optionally substituted with a Het$^1$ substituent; and $C_{2-4}$alkyl substituted with a —OH substituent; and $R^{1BB}$ is hydrogen; or
(e) -L-$R^3$ is

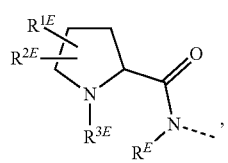

wherein
$R^E$ is selected from the group consisting of hydrogen and methyl;
$R^{1E}$ and $R^{2E}$ are each an independently selected $C_{1-4}$alkyl substituent; or $R^{1E}$ and
$R^{2E}$ are bound to the same carbon atom and together form a $C_{3-5}$cycloalkyl; and
$R^{3E}$ is hydrogen;

(vii) -L-$R^3$ is selected from (a), (b), or (e):
(a) -L-$R^3$ is —NHR$^{1A}$, wherein $R^{1A}$ is selected from the group consisting of $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$, wherein $R^{1a}$, $R^{2a}$ and $R^{2aa}$ are each independently selected from the group consisting of hydrogen, $C_{1-4}$alkyl and cyclopropyl; or
(b) L is —NH—CH$_2$— and $R^3$ is selected from the group consisting of Ar and Het$^1$; or
(e) -L-$R^3$ is

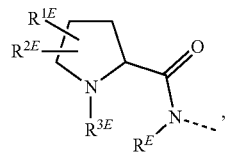

wherein
$R^E$ is selected from the group consisting of hydrogen and methyl;
$R^{1E}$ and $R^{2E}$ are each an independently selected $C_{1-4}$alkyl substituent; or $R^{1E}$ and
$R^{2E}$ are bound to the same carbon atom and together form a $C_{3-5}$cycloalkyl; and
$R^{3E}$ is hydrogen;

(viii) Ar is phenyl optionally substituted with one or two substituents each independently selected from the group consisting of halo, —C(=O)NR$^5$R$^{5'}$, and $C_{1-4}$alkyl; wherein $R^5$ and $R^{5'}$ are each independently selected from the group consisting of hydrogen and $C_{1-4}$alkyl;

(ix) Ar is phenyl optionally substituted with one or two substituents each independently selected from the group consisting of halo and $C_{1-4}$alkyl;

(x) Het$^1$ is a monocyclic heteroaryl selected from the group consisting of pyridyl, 4-, 5- or 6-pyrimidinyl, pyrazinyl, pyridazinyl, pyrrolyl, pyrazolyl, and imidazolyl; each of which may be optionally substituted with one or two substituents each independently selected from the group consisting of halo and $C_{1-4}$alkyl;

(xi) Het$^1$ is pyrazolyl optionally substituted with a $C_{1-4}$alkyl substituent;

(xii) Het$^2$ is a non-aromatic heterocyclyl selected from azetidinyl, pyrrolidinyl and piperidinyl, each of which may be optionally substituted with a $C_{1-4}$alkyl substituent.

All possible combinations of the above indicated embodiments are considered to be embraced within the scope of the invention.

Particular compounds of Formula (I) are:
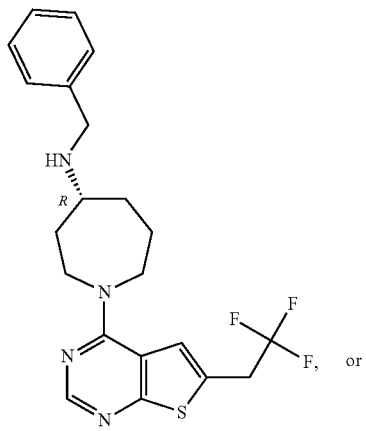
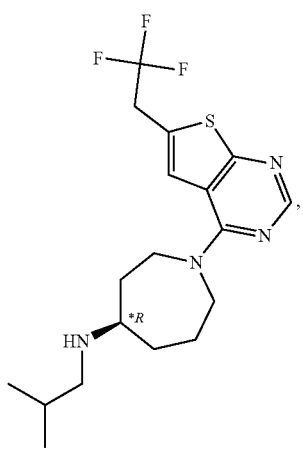
including the stereoisomeric forms, the pharmaceutically acceptable salts thereof, in particular the hydrochloride salts thereof, and the solvates thereof.
Particular compounds of Formula (I) are:
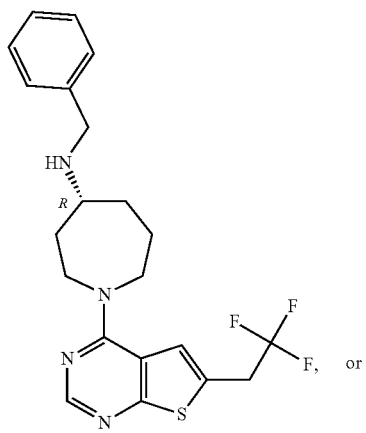
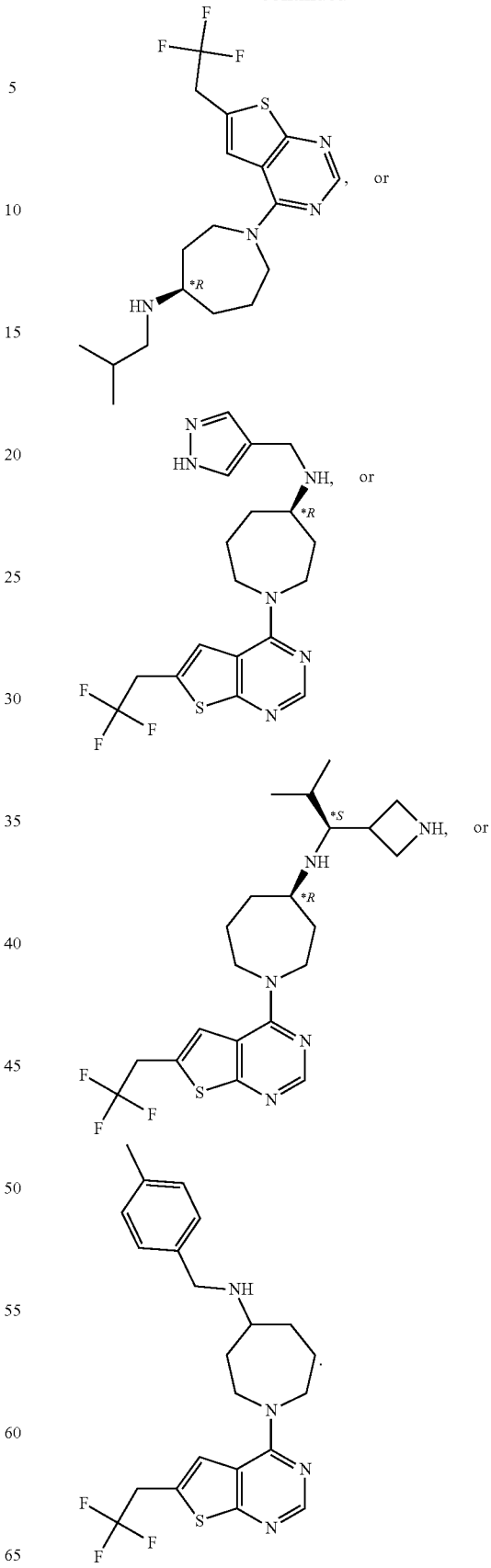
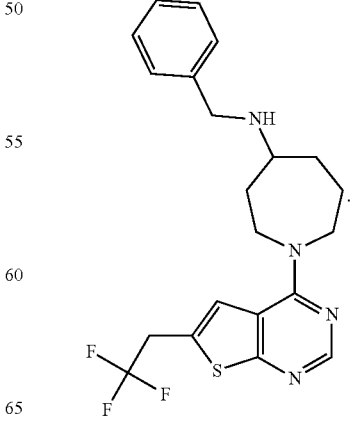

including the stereoisomeric forms, the pharmaceutically acceptable salts thereof in particular the hydrochloride salts thereof and the solvates thereof.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. For example in Scheme 5, the NH moiety on the azepanyl ring can be protected with a tert-butoxycarbonyl protecting group. In general, conventional protecting groups can be used in accordance with standard practice. The protecting groups may be removed at a convenient subsequent stage using methods known from the art. This is illustrated in the specific examples.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction workup (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the Schemes below may be further functionalized according to methods well-known by the person skilled in the art. The intermediates and compounds described herein can be isolated in free form or as a salt.

SCHEME 1

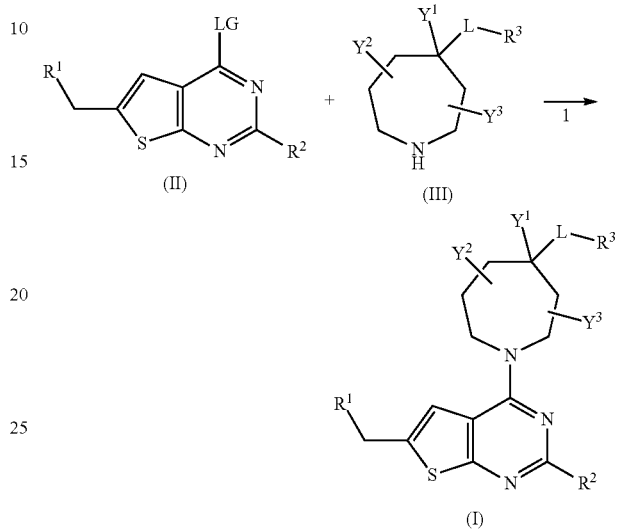

1: at a suitable temperature such as for example at room temperature, in the presence of a suitable base, such as for example diisopropylethylamine, in a suitable solvent, such as for example acetonitrile.

In general, compound of Formula (I) wherein all variables are defined according to the scope of the present invention, can be prepared according to the following reaction Scheme 1. In Scheme 1, LG is a leaving group, such as for example halo. All other variables in Scheme 1 are defined according to the scope of the present invention.

In Scheme 1, the following reaction conditions apply:

Alternatively, compounds of Formula (I), wherein all variables are defined according to the scope of the present invention, can be prepared according to the following reaction Scheme 2. In Scheme 2, $Y^1$ is hydrogen in compounds of Formula (IV'), (IV'') and (Ib) and $Y^{1a}$ has the same meaning as $Y^1$ defined in the scope of the invention except for hydrogen in compounds of Formula (VI), (VI') and (Ia), and all other variables are defined according to the scope of the invention.

In Scheme 2, the following reaction conditions apply:

SCHEME 2

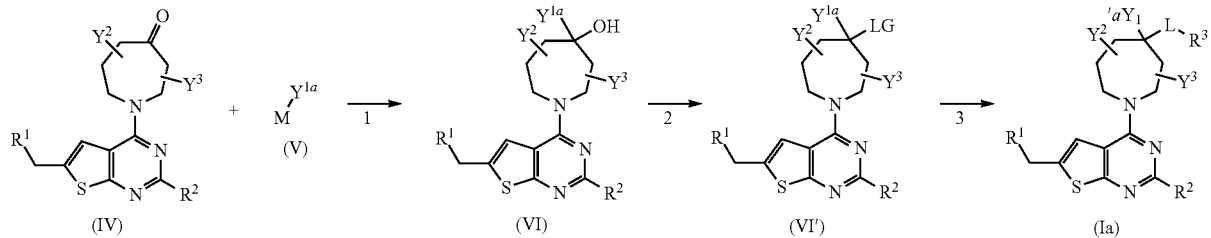

4

-continued

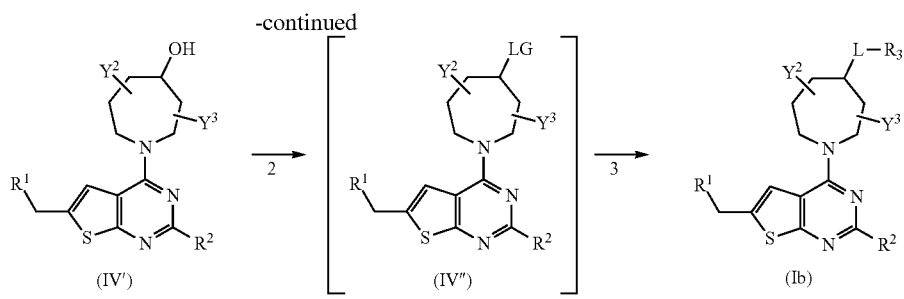

1: by addition of a Grignard reagent onto the ketone at a suitable temperature such as for example at -78° C., in a suitable solvent such as for example tetrahydrofuran (THF);
2: by transforming the hydroxyl moiety into a leaving group such as for example, a mesylate, or usingMitsunobu reaction, by methods known to the skilled person;
3: under appropriate reaction conditions, such as for example nucleophilic substituion conditions, by appropriate functional group interconversion with reagents that are either commercially available or can be prepared by methods known to the skilled person, yielding a compound of Formula (I) wherein $Y^{1a}$ has the same meaning as $Y^1$ except for hydrogen;
4: under appropriate reduction conditions such as for example using $NaBH_4$ in an suitable solvent such as alcohol at a suitable temperature.

Alternatively, compounds of Formula (I), wherein all variables are defined according to the scope of the present invention, can be prepared according to the following reaction Scheme 3. In Scheme 3, $Y^1$ is hydrogen in compound of Formula (Id), and $Y^{1a}$ has the same meaning as $Y^1$ defined in the scope of the invention except for hydrogen in compound of Formula (Ic), -L-$R^3$ is —N($R^B$)—$R^3$, —N($R^B$)—$CR^{1B}R^{1BB}$—$R^3$ or —N($R^B$)—$CHR^{1B}$—$CHR^{2B}$—$R^3$ as defined in (b), or -L-$R^3$ is as defined in (c) or (d), herein referred to as —NQ-$L^a$-$R^3$, and all other variables are defined according to the scope of the invention. It will be clear that Q represents $R^B$, $R^C$ or $R^D$ respectively, and $L^a$ is the remainder of the L definition not including —NQ—.

In Scheme 3, the following reaction conditions apply:

SCHEME 3

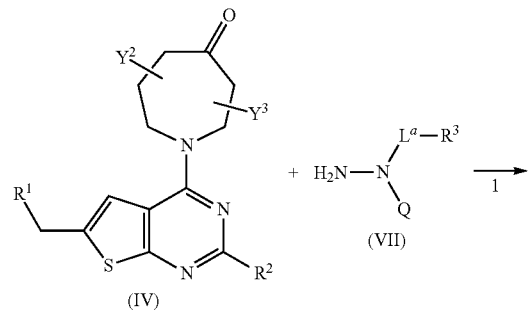

-continued

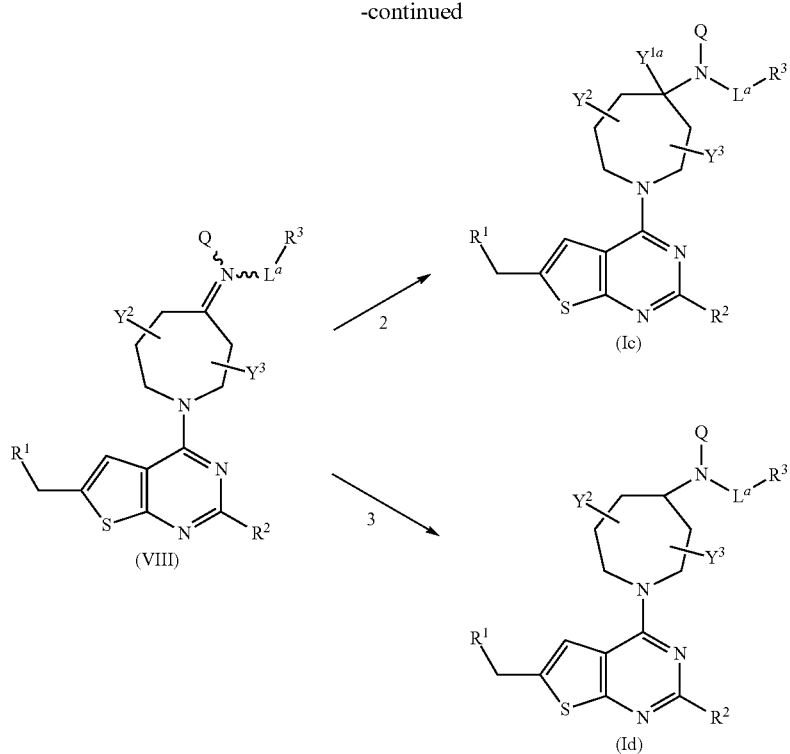

1: at a suitable temperature for example 80° C., in a suitable solvent such as ethanol;
2: under appropriate reaction conditions by appropriate functional group
   interconversion with suitable organolithium ($Y^{1a}$—Li) or Grignard ($Y^{1a}$—Mg-halo)
   reagents that are either commercially available or can be prepared by methods known
   to the skilled person, yielding a compound of Formula (I) wherein $Y^{1a}$ has the same meaning
   as $Y^1$ except for hydrogen;
3: at a suitable temperature, for example room temperature, in the presence of a suitable
   reducing agent, such as for example NaBH(OAc)$_3$, in a suitable solvent such as ethanol;
   yielding a compound of Formula (I) wherein $Y^1$ is hydrogen.

SCHEME 3B

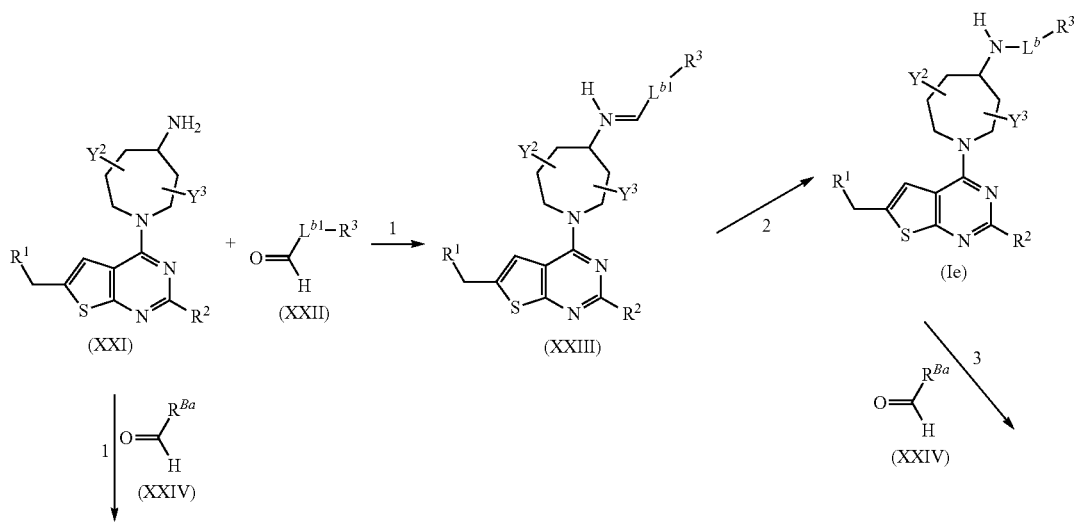

-continued

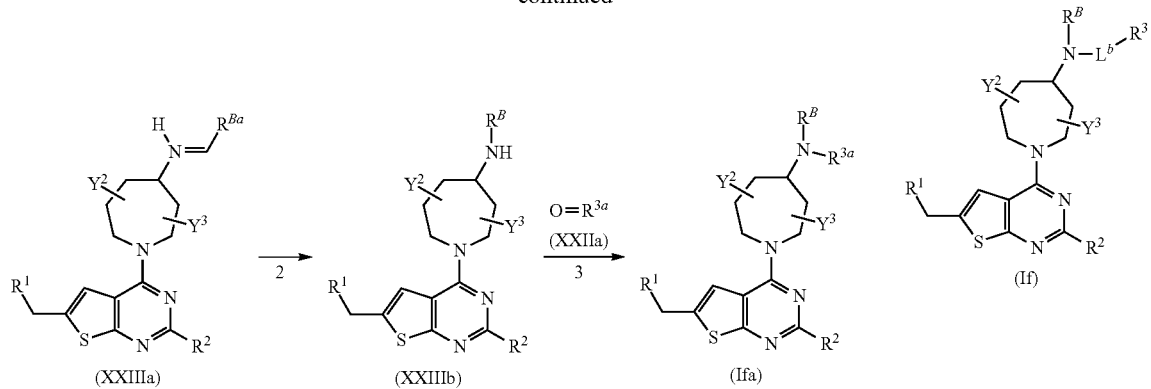

1: at a suitable temperature for example room temperature, in a suitable solvent such as ethanol, THF, dichloroethane (DCE), with or without acetic acid (AcOH).
2 and 3: at a suitable temperature, for example room temperature, in the presence of a suitable reducing agent, such as for example NaBH(OAc)$_3$ in a suitable solvent such as ethanol; THF, DCE with or without acetic acid (AcOH) yielding a compound of Formula (I) wherein Y$^1$ is hydrogen.

Alternatively, compounds of Formula (I), wherein
$L^b$ is $C_{1-2}$alkyl optionally substituted with $R^{2B}$;
$L^b1$ is $C_{0-1}$alkyl optionally substituted with $R^{2B}$;
$R^{3a}$ is selected from Het$^2$ or a 7- to 10-membered saturated spirocyclic system;
$R^{Ba}$ is selected from the group consisting of hydrogen; $C_{0-3}$alkyl optionally substituted with a substituent selected from the group consisting of fluoro, phenyl and —CN; and $C_{1-3}$alkyl substituted with a substituent selected from the group consisting of —OR$^{1b}$ and —NR$^{2b}$R$^{2bb}$;
can be prepared according to scheme 3B.

All other variables are defined according to the scope of the present invention. The skilled person will understand that in case $R^B$ is hydrogen, some reactions of Scheme 3B can be skipped.

Someone skilled in the art will realize that, in the preparation of compounds, the order of steps 1 and 2 can be inverted with step 3 and that, for example for the preparation of compounds (If), reagent ((XXIV) can be used prior to reagent (XXII).

SCHEME 4

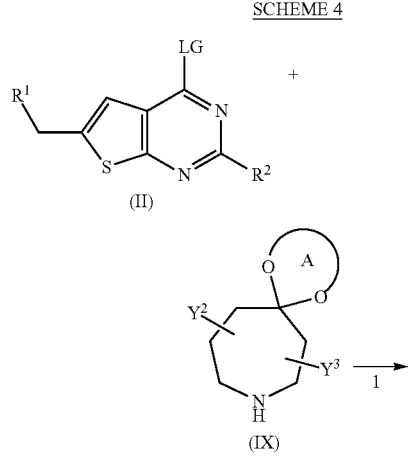

-continued

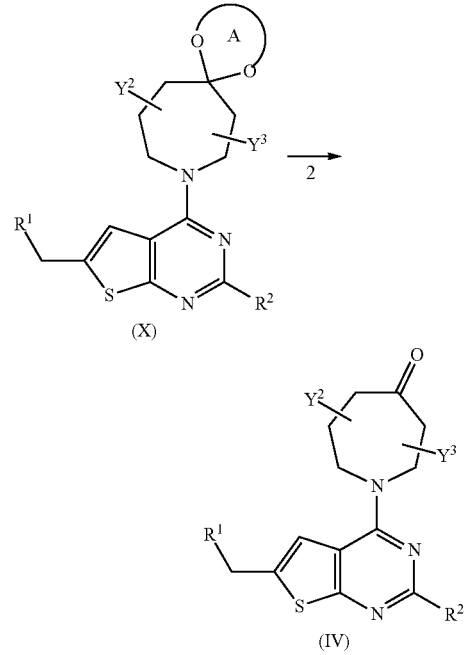

1: at a suitable temperature such as for example at 80° C., in the presence of a suitable base, such as for example diisopropylethylamine, in a suitable solvent, such as for example isopropanol.
2: under suitable reaction conditions to cleave the protecting group, such as for example in the presence of an acid such as hydrochloric acid at reflux.
Alternatively, intermediates of Formula (IX) that are protected or unprotected, may be commercially available.

Intermediates of Formula (IV), can be prepared according to the following reaction
Scheme 4, wherein

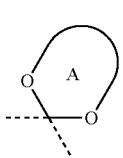

represents a suitable protecting group, such as for example an acetal protecting group and all other variables are defined according to the scope of the present invention.

In Scheme 4, the following reaction conditions apply:

SCHEME 4B

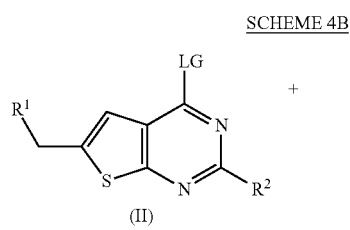

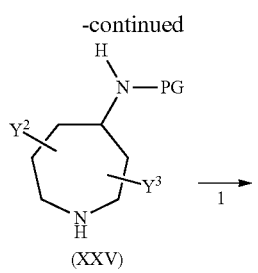

1: at a suitable temperature such as for example at 80° C., in the presence of a suitable base, such as for example diisopropylethylamine, in a suitable solvent, such as for example isopropanol. Suitable PG (protecting group) for compound (XXV) such as for example tert-butyloxycarbonyl.

2: under suitable reaction conditions to cleave the protecting group, such as for example in the presence of an acid such as hydrochloric acid or trifluoroacetic acid at room temperature.

1: at a suitable temperature such as for example at 80° C., in the presence of a suitable base, such as for example diisopropylethylamine, in a suitable solvent, such as for example isopropanol.

Alternatively, further intermediates of Formula (IV) can be prepared according to the following reaction Scheme 4B.

In Scheme 4B, the following reaction conditions apply:

SCHEME 4C

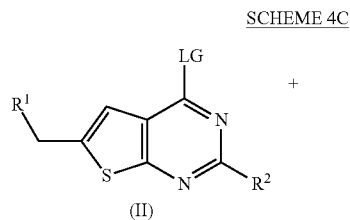

Intermediates of Formula (XXI) can be prepared according to the following reaction Scheme 4b

SCHEME 5

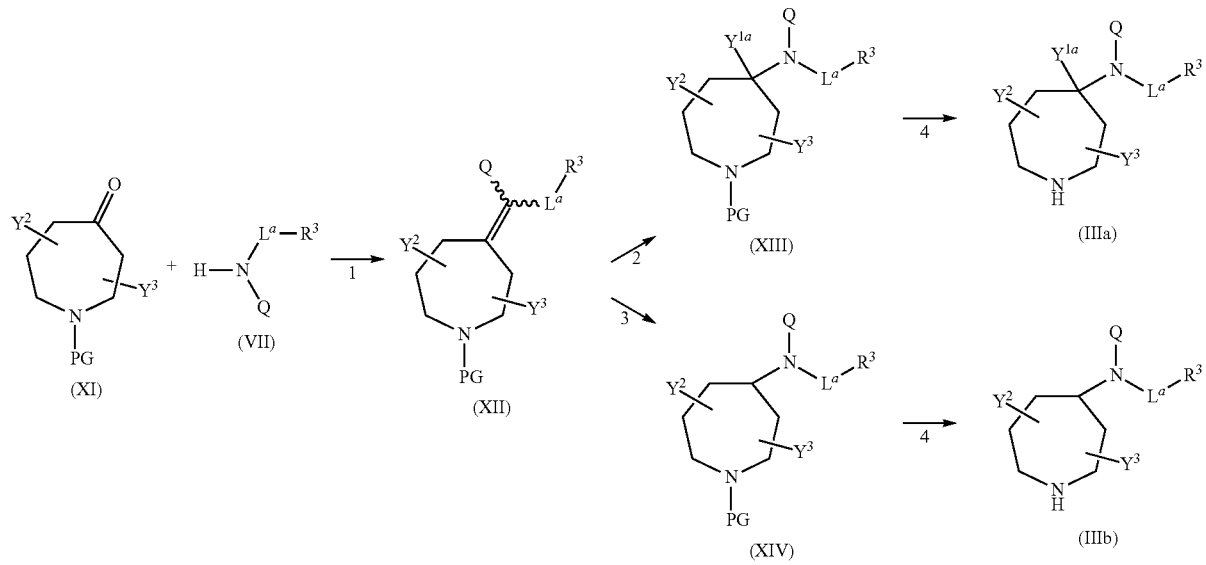

1: at a suitable temperature for example 80° C., in a suitable solvent such as ethanol;
2: under appropriate reaction conditions by appropriate functional group interconversion with suitable organolithium ($Y^{1a}$-Li) or Grignard ($Y^{1a}$-Mg-halo) reagents that are either commercially available or can be prepared by methods known to the skilled person, yielding a compound of Formula (XIII) wherein $Y^{1a}$ has the same meaning as $Y^1$ except for hydrogen;
3: at a suitable temperature, for example room temperature, in the presence of a suitable reducing agent, such as for example NaBH(OAc)3, in a suitable solvent such as ethanol; yielding a compound of Formula (XIV) wherin $Y^1$ is a hydrogen;
4: at a suitable temperature such as for example from 0° C. to room temperature, in the presence of suitable cleavage conditions, such as for example an acid such as hydrochloricacid in a suitable solvent such as acetonitrile when PG is tert-butyloxycarbonyl.
Alternatively, intermediates of Formula (III) may be commercially available.

Intermediates of Formula (III) can be prepared according to the following reaction Scheme 5, wherein $Y^1$ is hydrogen in compound of Formula (IIIb), and $Y^{1a}$ has the same meaning as $Y^1$ defined in the scope of the invention except for hydrogen in compound of Formula (IIIa), -L-$R^3$ is —N($R^B$)—$R^3$, —N($R^B$)—C$R^{1B}R^{1BB}$—$R^3$ or —N($R^B$)—CH$R^{1B}$—CH$R^{2B}$—$R^3$ as defined in (b), or -L-$R^3$ is as defined in (c) or (d), herein referred to as —NQ-$L^a$-$R^3$ or —NH-$L^a$-$R^3$, and all other variables are defined according to the scope of the invention.

In Scheme 5, the following reaction conditions apply:

SCHEME 5B

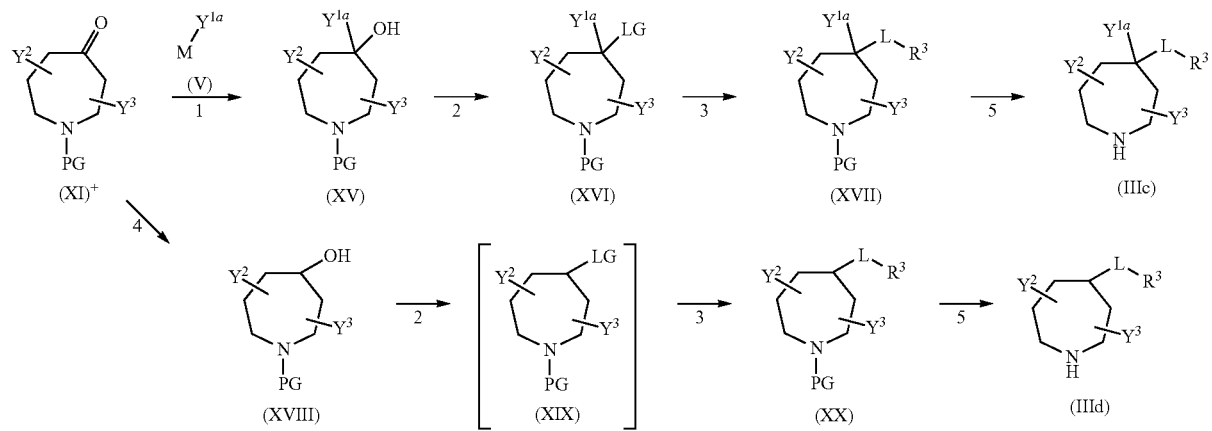

-continued

1: by addition of a Grignard reagent onto the ketone at a suitable temperature such as for example at -78° C., in a suitable solvent such as for example THF;
2: by transforming the hydroxyl moiety into a leaving group such as for example, a mesylate, or using Mitsunobu reaction, by methods known to the skilled person;
3: under appropriate reaction conditions, such as for example nucleophilic substitution conditions, by appropriate functional group interconversion with reagents that are either commercially available or can be prepared by methods known to the skilled person, yielding a compound of Formula (XVII) wherein $Y^{1a}$ has the same meaning as $Y^1$ except for hydrogen, or a compound of Formula (XX);
4: under appropriate reduction conditions such as for example using NaBH$_4$ in an suitable solvent such as alcohol at a suitable termperature.
5: at a suitable temperature such as for example from 0° C. to room temperature, in the presence of suitable cleavage conditions, such as for example an acid such as hydrochloric acid in a suitable solvent such as acetonitrile when PG is tert-butyloxycarbonyl.
Alternatively, intermediates of Formula (IIIc) and (IIId) may be commerically available.

Alternatively, further intermediates of Formula (III), herein referred to as (IIIc) and (IIId) can be prepared according to the following reaction Scheme 5b. In Scheme 5b, $Y^1$ is hydrogen in compounds of Formula (IIId), (XIX) and (XX) and $Y^{1a}$ has the same meaning as $Y^1$ defined in the scope of the invention except for hydrogen in compounds of Formula (IIIc), (XV), (XVI) and (XVII), and all other variables are defined according to the scope of the invention.

In Scheme 5b, the following reaction conditions apply:

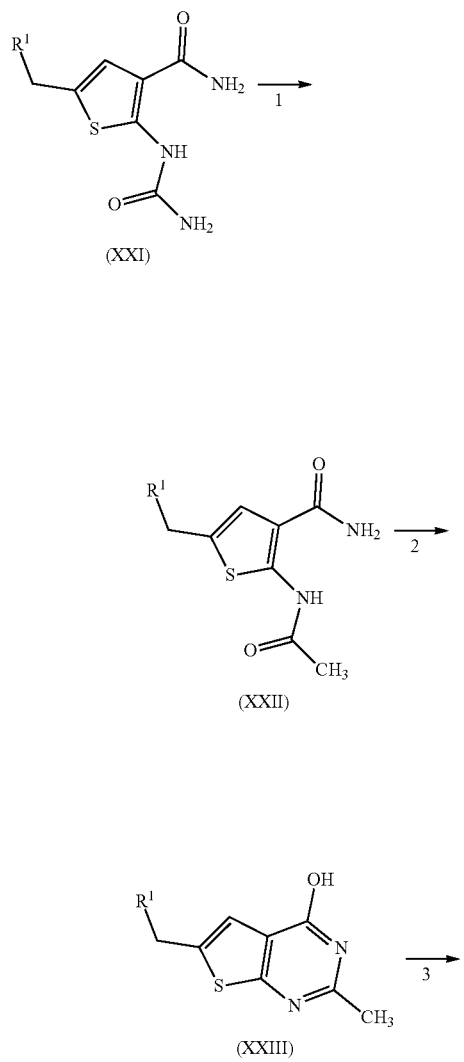

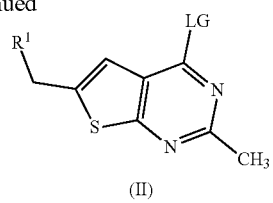

1: at suitable temperature such as for example at reflux temperature, in the presence of acetic anhydride and a suitable base such as for example trimethylamine, in a suitable solvent, such as for example toluene;
2: at a suitable temperature such as for example at reflux temperature, in the presence of a suitable base such as ptoassium hydroxide, in a suitable solvent such as for example ethanol;
3: under suitable reaction conditions to form a leaving group, such as for example, chloro, for example by reaction with phosphoryl trichloride at a suitable temperature such as at 110° C.
Alternatively, intermediates of Formula (II) may be commercially available.

Intermediates of Formula (II), wherein $R^2$ is methyl, can be prepared according to the following reaction Scheme 6, wherein LG represents a suitable leaving group, such as for example, halo or methanesulfonyl. All other variables in Scheme 6 are defined according to the scope of the present invention.

In Scheme 6, the following reaction conditions apply:

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-PG) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Pharmacology

It has been found that the compounds of the present invention block the interaction of menin with MLL proteins and oncogenic MLL fusion proteins. Therefore the compounds according to the present invention and the pharmaceutical compositions comprising such compounds may be useful for the treatment or prevention, in particular treatment, of diseases such as cancer, myelodysplastic syndrome (MDS) and diabetes.

In particular, the compounds according to the present invention and the pharmaceutical compositions thereof may be useful in the treatment or prevention of cancer. According to one embodiment, cancers that may benefit from a treatment with menin/MLL inhibitors of the invention comprise leukemias, myeloma or a solid tumor cancer (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, leukemias exphibiting HOX/MEIS1 gene expression signatures etc.

Hence, the invention relates to compounds of Formula (I), the tautomers and the stereoisomeric forms thereof, and the pharmaceutically acceptable salts, and the solvates thereof, for use as a medicament.

The invention also relates to the use of a compound of Formula (I), a tautomer or a stereoisomeric form thereof, or a pharmaceutically acceptable salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable salt, or a solvate thereof, or a pharmaceutical composition according to the invention, for use in the treatment, prevention, amelioration, control or reduction of the risk of disorders associated with the interaction of menin with MLL proteins and oncogenic MLL fusion proteins in a mammal, including a human, the treatment or prevention of which is affected or facilitated by blocking the interaction of menin with MLL proteins and oncogenic MLL fusion proteins.

Also, the present invention relates to the use of a compound of Formula (I), a tautomer or a stereoisomeric form thereof, or a pharmaceutically acceptable salt, or a solvate thereof, or a pharmaceutical composition according to the invention, for the manufacture of a medicament for treating, preventing, ameliorating, controlling or reducing the risk of disorders associated with the interaction of menin with MLL proteins and oncogenic MLL fusion proteins in a mammal, including a human, the treatment or prevention of which is affected or facilitated by blocking the interaction of menin with MLL proteins and oncogenic MLL fusion proteins.

The invention also relates to a compound of Formula (I), a tautomer or a stereoisomeric form thereof, or a pharmaceutically acceptable salt, or a solvate thereof, for use in the treatment or prevention of any one of the diseases mentioned hereinbefore.

The invention also relates to a compound of Formula (I), a tautomer or a stereoisomeric form thereof, or a pharmaceutically acceptable salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), the tautomers and the stereoisomeric forms thereof, and the pharmaceutically acceptable salts, and the solvates thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof, or a pharmaceutically acceptable salt, or a solvate thereof, to warm-blooded animals, including humans.

Therefore, the invention also relates to a method for the treatment or prevention of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 100 mg/kg, in particular 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be 1 mg/kg body weight, 2 mg/kg body weight, 4 mg/kg body weight, or 8 mg/kg body weight. The amount of a compound according to the present invention, also referred to herein as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular condition, in particular tumour, being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The following examples further illustrate the present invention.

EXAMPLES

Several methods for preparing the compounds of this invention are illustrated in the following examples. Unless otherwise noted, all starting materials were obtained from commercial suppliers and used without further purification.

Hereinafter, the terms: 'ACN' or 'CAN' means acetonitrile, 'DCM' means dichloromethane, 'DCE' means dichloroethane, 'DIEA' means N,N-diisopropylethylamine, 'DIAD' means diisopropyl diazodicarboxylate, 'h' means hours(s), 'min' means minute(s), 'DMF' means dimethylformnamide, 'DSC' means differential scanning calorimetry, 'EtOAc' or 'AcOEt' means ethyl acetate, 'Et$_2$O' means diethyl ether, 'EtOH' means ethanol, 'THF' means tetrahydrofuran, 'HPLC' means High-performance Liquid Chromatography, 'HBTU' means I-bis(dimethylamino)methylene-benzotriazoliurnhexafluorophosphate(1-)3-oxide, 'iPrOH' means isopropyl alcohol, TFA means trifluoroacetic acid, NaBH$_4$ means sodium borohydride, TBAF means tetrabutylammonium fluoride, K$_2$CO$_3$ means potassium carbonate, MgSO$_4$ means magnesium sulfate, Na$_2$SO$_4$ means sodium sulfate, Et$_3$N means triethylamine, PPh$_3$ means triphenyl phosphine, NaHCO$_3$ means sodium hydrogenocarbonate, 'LC/MS' means Liquid Chromatography/Mass Spectrometry, 'MeOH' means methanol, 'NMR' means Nuclear Magnetic Resonance, 'rt' means room temperature, "SFC" means supercritical fluid chromatography, 'M.P.' or 'm.p.' means melting point, 'OR' means optical rotation.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

When a stereocenter is indicated with 'RS' this means that a racemic mixture was obtained at the indicated centre, unless otherwise indicated.

The stereochemical configuration for centres in some compounds may be designated "R" or "S" when the mixture (s) was separated; for some compounds, the stereochemical configuration at indicated centres has been designated as "*R" (first eluted from the column in case the column conditions are described in the synthesis protocol and when only one stereocentre present) or "*S" (second eluted from the column in case the column conditions are described in the synthesis protocol and when only one stereocentre present) when the absolute stereochemistry is undetermined (even if the bonds are drawn stereospecifically) although the compound itself has been isolated as a single stereoisomer and is enantiomerically pure.

For example, it will be clear that compound 11A

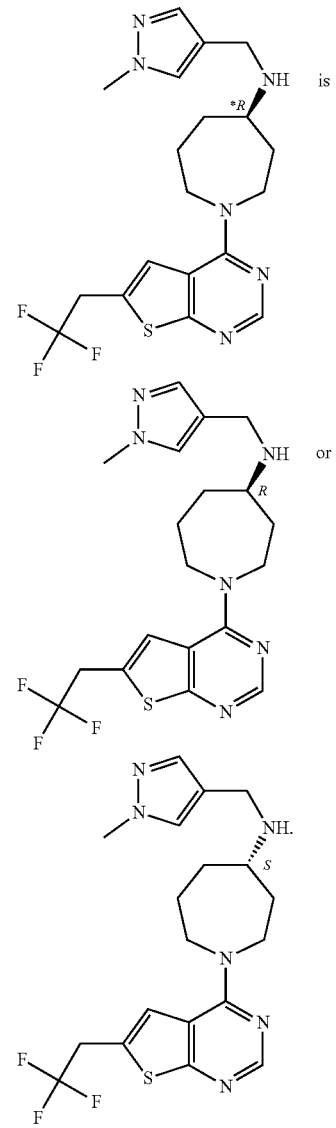

Compounds having two stereocentres of which only the stereochemical configuration of one stereocentre is indicated by * (e.g. *R or *S) (see for example compound 14A or 14B), follow a similar rule as above. This means that the absolute stereoconfiguration of the stereocentre indicated by * is undetermined (even if the bonds are drawn stereospecifically) although the compound is enantiomerically pure at the indicated centre.

For compounds such as for example 31, 32, 35, 36, 54A, 54B, 54C, 54D, 66A, 66B, 66C, 66D, 68A and 68B, wherein the stereochemical configuration of two stereocentres is indicated by * (e.g. *R or *S), the absolute stereochemistry of the stereocentres is undetermined (even if the bonds are drawn stereospecifically), although the compound itself has been isolated as a single stereoisomer and is enantiomerically pure. In this case, the configuration of the first stereocentre is independent of the configuration of the second stereocentre in the same compound.

For example, for Compound 31

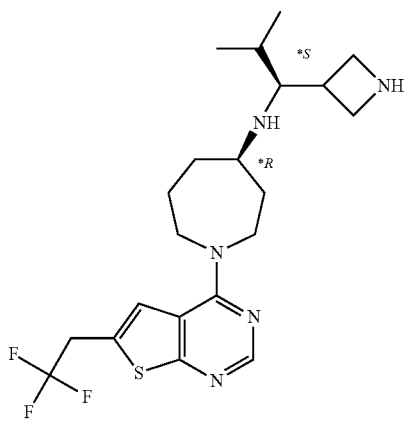 [SMILES: CC(C)[C@H](N[C@@H]1CCCN(c2ncnc3sc(CC(F)(F)F)cc23)CC1)C1CNC1]

this means that the compound is

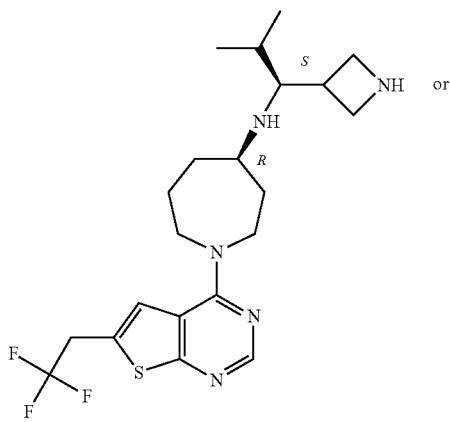

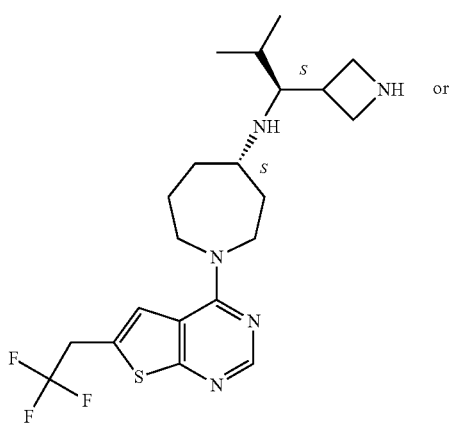

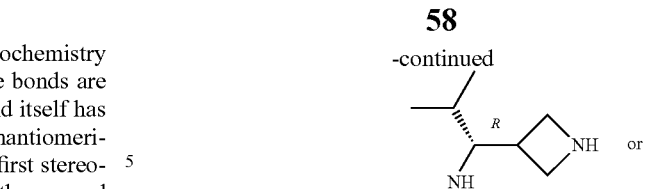

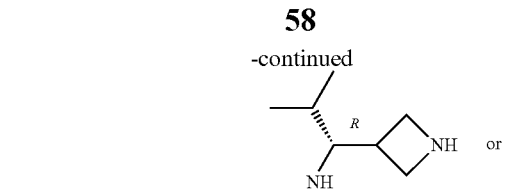

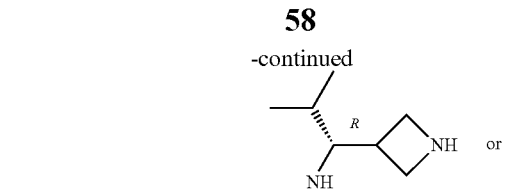

The paragraphs above about stereochemical configurations, also apply to intermediates.

The term "enantiomerically pure" as used herein means that the product contains at least 80% by weight of one enantiomer and 20% by weight or less of the other enantiomer. Preferably the product contains at least 90% by weight of one enantiomer and 10% by weight or less of the other enantiomer. In the most preferred embodiment the term "enantiomerically pure" means that the composition contains at least 99% by weight of one enantiomer and 1% or less of the other enantiomer.

When an intermediate or compound in the experimental part below is indicated as 'HCl salt' or 'TFA salt' without indication of the number of equivalents of HCl or TFA, this means that the number of equivalents of HCl or TFA was not determined.

A skilled person will realize that, even where not mentioned explicitly in the experimental protocols below, typically after a column chromatography purification, the desired fractions were collected and the solvent was evaporated.

A. Preparation of the Intermediates

Preparation of Intermediate 1

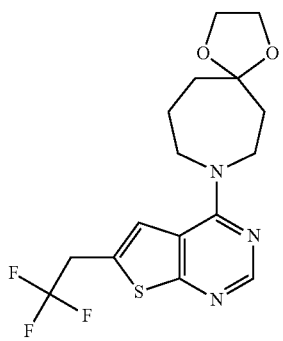 [SMILES: FC(F)(F)Cc1cc2c(N3CCCC4(CC3)OCCO4)ncnc2s1]

A mixture of 1,4-dioxan-8-azaspiro[4.6]undecane (1 g, 6.36 mmol) (CAS[16803-07-9]); 4-chloro-6-(2,2,2-trifluoroethyl)thieno[2,3-d]pyrimidine (CAS[1628317-85-0]) (1.46 g, 5.78 mmol) prepared as described in Journal of Medicinal Chemistry (2016), 59(3), 892-913; and DIEA (3 mL, 17.35 mmol) in iPrOH (60 mL) was heated at 80° C. for 3 h. The mixture was cooled to rt, poured into ice water extracted with EtOAc twice. The combined organic layers were washed with brine, dried over MgSO$_4$, filtered and evaporated till dryness. The residue was purified by chromatography over silica gel (Stationary phase: irregular SiOH 15-40 µm 40 g, Mobile phase: 97% DCM, 3% MeOH (+10% NH$_4$OH)). The fractions containing product were collected and evaporated to dryness yielding 2.28 g (yield 106%) of 8-(6-(2,2,2 trifluoroethyl) thieno[2,3-d]pyrimidin-4-yl)-1,4-dioxa-8-azaspiro[4.6]undecane (I-1) that was used without further purification in the next step.

The compound in the Table below was prepared using an analogous method as described for the preparation of compound above, starting from the respective starting materials

| INTERMEDIATE NUMBER | STRUCTURE | YIELD |
|---|---|---|
| Intermediate 2 | 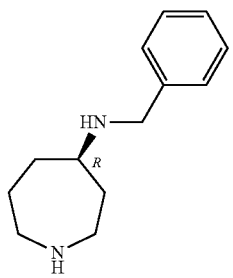 | 98% |

Preparation of Intermediate 3

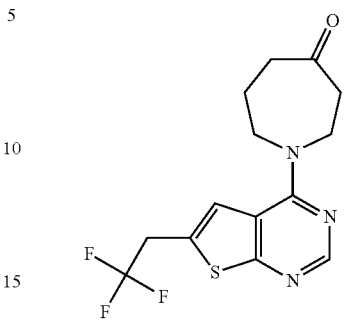

Intermediate 1 (90 mg, 0.24 mmol) in HCl (1 mL, 6N) was stirred at reflux for 5 h. The reaction mixture was cooled to rt, poured into ice water, basified with a solution of NaOH (3N) and the product was extracted with DCM. The organic layer was separated, dried over MgSO$_4$, filtered and evaporated till dryness to give 58 mg (yield 73%) of 1-(6-(2,2,2-trifluoroethyl)thieno[2,3-d]pyrimidin-4-yl)azepan-4-one.

Preparation of Intermediate 4

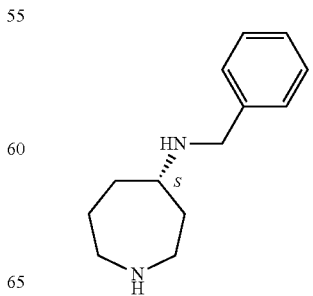

A mixture of (R)-tert-butyl 4-(benzylamino)azepane-1-carboxylate (160 mg, 0.53 mmol) (CAS[1391730-07-6]), and a solution of HCl in dioxane (1.5 mL/4N, 6 mmol) in MeOH (3 mL) was stirred at rt for 6 h. The mixture was evaporated to dryness giving 129 mg of intermediate 4 that was used without further purification in the next step.

Similarly prepared from (S)-tert-butyl 4-(benzylamino)azepane-1-carboxylate (CAS[1391730-08-7]) was intermediate 5:

Preparation of Intermediate 6

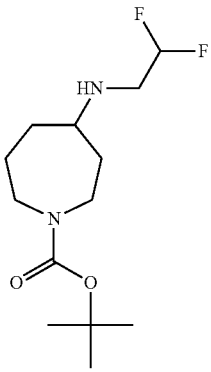 [SMILES: CC(C)(C)OC(=O)N1CCCC(NCC(F)F)CC1]

Under N₂ flow, 2,2-difluoroethylamine (0.39 mL, 5.51 mmol) was added to a solution of tert-butyl 4-oxoazepane-1-carboxylate (350 mg, 1.38 mmol), (CAS[188975-88-4]), and acetic acid (0.17 mL, 3.03 mmol) in THF (5 mL). The mixture was stirred at rt for 30 min, then NaBH(OAc)₃ (643 mg, 3.03 mmol) was added and the mixture was stirred at rt overnight. The mixture was poured into ice water and decanted, the aqueous layer was extracted with DCM (×2). The organic layers were combined, washed with brine then dried over MgSO₄, and evaporated to give 380 mg of intermediate 6 tert-butyl 4-((2,2-difluoroethyl)amino)azepane-1-carboxylate. The crude product was used directly for the next step without any purification.

Preparation of Intermediate 7

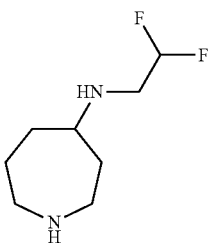 [SMILES: FC(F)CNC1CCCNCC1]

as an HC salt

At 5° C., a solution of HCl in dioxane (3.4 mL/4N, 13.65 mmol) was added dropwise to a solution of intermediate 5 (380 mg, 1.37 mmol) in DCM (10 mL), and the mixture was stirred at rt for 5 h. The reaction was evaporated to dryness, the residue was taken-up with Et₂O and the white precipitate was filtered off and dried under vacuum to give 350 mg of intermediate 7 as an HCl salt.

Preparation of Intermediate 8

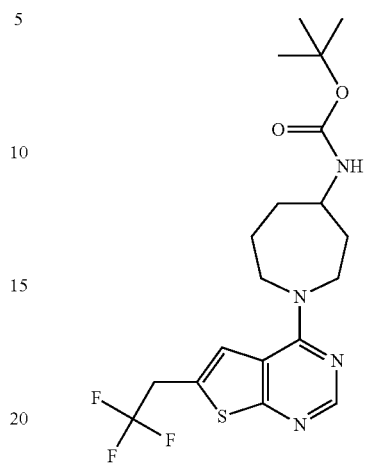

A mixture of 4-chloro-6-(2,2,2-trifluoroethyl)thieno[2,3-d]pyrimidine (CAS [1628317-85-0]) (3 g, 11.87 mmol), t-butyl N-(azepane-4-yl) carbamate (CAS[454451-28-6]) (3.05 g, 14.25 mmol), and DIEA (8.2 mL, 47.5 mmol) in iPrOH (75 mL) was heated at 90° C. for 2 h. The mixture was cooled to rt, then poured out into water and the product was extracted with EtOAc. The organic layer was separated, washed with brine, dried over MgSO₄, filtered, and evaporated to dryness. The residue was purified by chromatography over silica gel (Stationary phase: irregular SiOH 15-40 µm 40 g GRACE, Mobile phase: Gradient from 100% DCM to 0.1% NH₄OH, 98% DCM, 2% MeOH). The fractions containing product were collected and evaporated to dryness yielding 4.8 g (yield 94%) of intermediate 8.

Preparation of Intermediate 8A and Intermediate 8A and Intermediate

I-8A

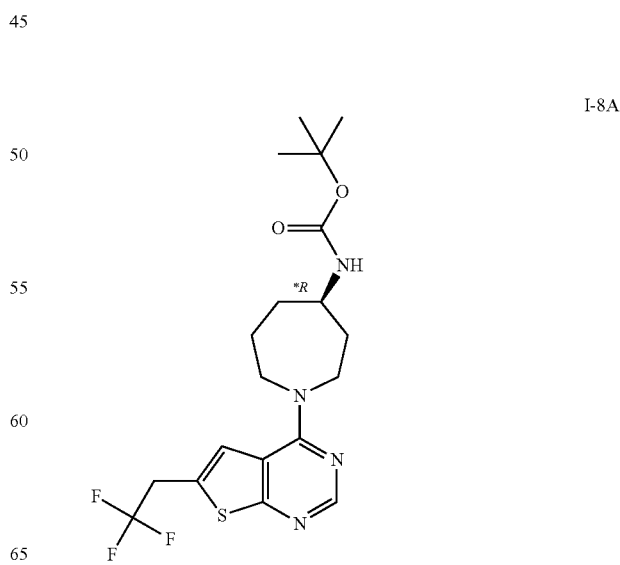

I-8B

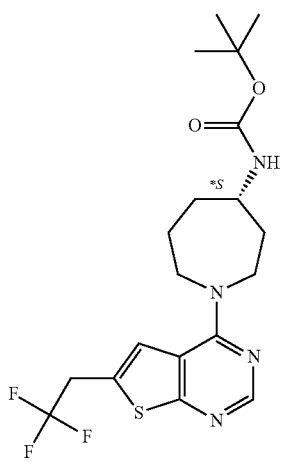 [SMILES: CC(C)(C)OC(=O)NC1CCCN(c2ncnc3sc(CC(F)(F)F)cc23)CC1]

| INTERMEDIATE NUMBER | STRUCTURE |
| --- | --- |
| Intermediate 10 (from intermediate 8A) | 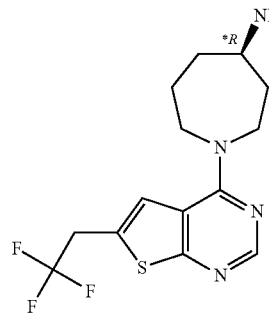<br>as an HCl salt |
| Intermediate 11 (from intermediate 8B) | 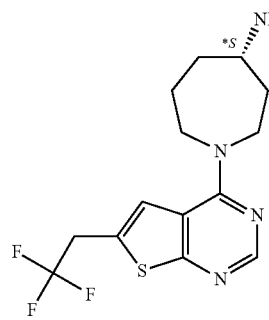<br>as an HCl salt |

The enantiomers of racemic mixture of intermediate 8 were separated using chiral SFC (Stationary phase: Chiralpak AD-H 5 μm 250*30 mm, Mobile phase: 82% $CO_2$, 18% EtOH). The fractions containing product were collected and evaporated to dryness yielding 1.35 g (yield 26%) of first eluted enantiomer 8A (intermediate 8A; I-8A) ([α]=+4.78° (589 nm, c 0.293 w/v %, DMF, 20° C.)) and 1.47 g (yield 290%) of second eluted enantiomer 8B (intermediate 8B; I-8B) ([α]=−4.95° (589 nm, c 0.364 w/v %, DMF. 20° C.)).

Preparation of Intermediate 9

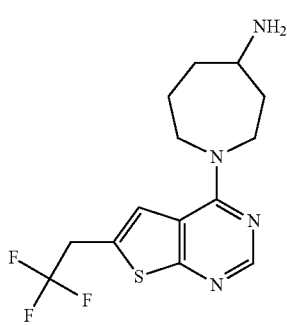 [SMILES: NC1CCCN(c2ncnc3sc(CC(F)(F)F)cc23)CC1]

as an HCl salt

At 5° C., HCl (11.6 mL, 46.46 mmol, a 4M solution in dioxane) was added dropwise to a solution of intermediate 8 (2 g, 4.65 mmol) in DCM (50 mL), and the mixture was stirred at rt for 15 h. The reaction mixture was evaporated to dryness. The residue was taken-up with $Et_2O$ and evaporated to dryness twice to give 1.8 g of intermediate 9 as an HCl salt, which was used without any further purification for the next step.

The compounds in the Table below were prepared using an analogous method as described for the preparation of intermediate 9 above, starting from the respective starting materials Preparation of Intermediate 12A

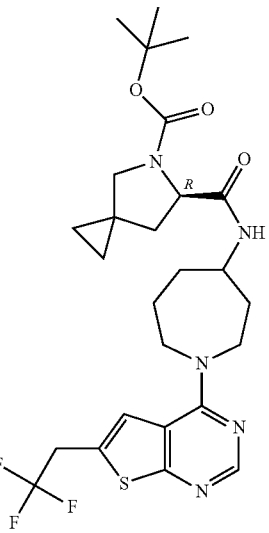

Under $N_2$ flow, at 10° C., HBTU (188 mg, 0.5 mmol) was added to a solution of (R)-5-Boc azaspiro[2.4]heptane-6 carboxylic acid (CAS[1129634-44-1]) (120 rag, 0.66 mmol) and DIEA (0.43 mL, 2.49 mmol) in DMF (5 mL). The solution was stirred at 10° C. for 30 min. Then intermediate 9 (200 mg, 0.55 mmol) was added, and the solution was stirred at rt for 15 h. The reaction mixture was then poured into cooled water, and K₂CO₃ 10%. The product was extracted with EtOAc, the organic layer was washed with brine, dried over MgSO₄, filtered and evaporated to dryness. The residue was purified by chromatography over silica gel (Stationary phase: irregular SiOH 15-40 µm 24 g, Mobile phase: Gradient from 0.1% NH₄OH, 98% DCM, 2% MeOH to 0.1% NH₄OH, 95% DCM, 5% MeOH). The fractions containing product were collected and evaporated to dryness yielding 100 mg (yield 36%) of intermediate 12A.

The compound in the Table below was prepared using an analogous method as described for the preparation of intermediate 12A above, starting from the respective starting materials

| INTERMEDIATE NUMBER | STRUCTURE | YIELD |
| --- | --- | --- |
| Intermediate 12B from (S)-5-Boc azaspiro[2.4]heptane-6 carboxylic acid | 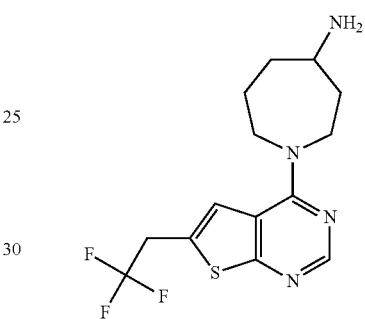 | 54% |

Preparation of Intermediate 13

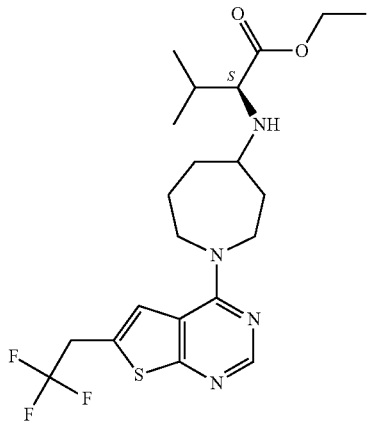

Under N₂ flow, a solution of intermediate 3 (223 mg, 0.68 mmol), L-valine ethyl ester hydrochloride (CAS: [17609-47-1]), (308 mg, 1.70 mmol) and acetic acid (78 µL, 1.35 mmol) in THF (6 m L) was stirred at rt for 3 h. NaBH(OAc)₃ (308 mg; 1.7 mmol) was added and the mixture was stirred at rt overnight. The mixture was poured into ice water, separated and the aqueous layer was extracted with EtOAc twice. The organic layers were combined, washed with brine, dried over MgSO₄ and evaporated to dryness. The residue was purified by chromatography over silica gel (Stationary phase: irregular SiOH 15-40 µm 24 g MERCK, Mobile phase: 97% DCM, 3% MeOH (+10% NH₄OH)). The fractions containing product were collected and evaporated to dryness yielding 176 mg of intermediate 13 (yield 26%). The product was further purified by chromatography over silica gel (Stationary phase: irregular SiOH 15-40 µm 24 g, Mobile phase: 60%0 HEPTANE, 35% AcOEt, 5% MeOH (+10% NH₄OH)). The fractions containing product were collected and evaporated to dryness yielding 82 mg of intermediate 13.

Preparation of Intermediate 14 as a TFA salt

TFA (1.6 mL, 20.9 mmol) was added at rt to a solution of intermediate 8 (0.9 g, 2.1 mmol) in DCM (9 mL), and the mixture was stirred at rt overnight. The reaction mixture was evaporated to dryness giving 1.5 g of intermediate 14 as a TFA salt, which was used without any further purification for the next step.

The compounds in the Table below were prepared using an analogous method as described for the preparation of intermediate 14 above, starting from the respective starting materials.

| INTERMEDIATE NUMBER | STRUCTURE |
| --- | --- |
| Intermediate 15 (from intermediate 8A) | as a TFA salt |

| INTERMEDIATE NUMBER | STRUCTURE |
|---|---|
| Intermediate 16 (from intermediate 8B) | 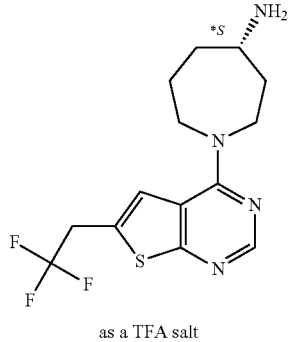 [SMILES: N[C@H]1CCCN(c2ncnc3sc(CC(F)(F)F)cc23)CC1]<br>as a TFA salt |

Preparation of Intermediate 17

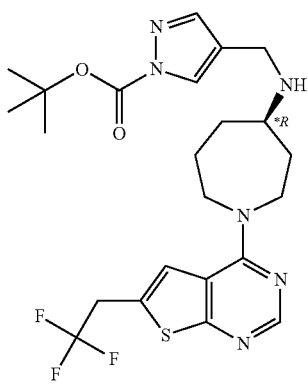

Tert-Butyl 4-formyl-1H-pyrazole-1-carboxylate (CAS [821767-61-7]), (122 mg, 0.62 mmol) was added at 10° C., under $N_2$ to a solution of intermediate 15 (183 mg, 0.55 mmol) in MeOH (7 mL). The mixture was stirred at rt for 5 h. Then $NaBH_4$ (31 mg, 0.83 mmol) was added portionwise and the mixture was stirred at rt for 15 h. The mixture was poured into ice water, extracted with DCM. The organic layer was dried over $MgSO_4$, filtered and evaporated to dryness giving 0.35 g of crude compound. The residue was purified by chromatography over silica gel (Stationary phase: irregular SiOH 15-40 μm 40 g, Mobile phase: Gradient from 0.1% $NH_4OH$, 97% DCM, 3% MeOH to 0.1% $NH_4OH$, 95% DCM, 5% MeOH). The fractions containing product were collected and evaporated to dryness yielding 150 mg (yield 39%) of intermediate 17.

Preparation of Intermediate 18

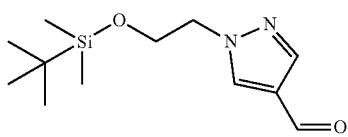 [SMILES: CC(C)(C)[Si](C)(C)OCCn1cc(C=O)cn1]

A solution of 2-bromoethoxy-tert-butyldimethylsilane (CAS 1186864-60-011), (2.44 mL; 11.37 mmol), 1H-pyrazole-4-carbaldehyde (CAS [35344-95-7]), (0.91 g; 9.5 mmol) and $K_2CO_3$ (1.57 g; 11.37 mmol) in ACN (18 mL) was refluxed for 2 h. The mixture was cooled, poured into ice water and a saturated $NaHCO_3$ solution, the aqueous layer was extracted with EtOAc. The organic layer was separated, dried over $MgSO_4$, filtered and evaporated to dryness giving a crude compound which was purified by chromatography over silica gel (Stationary phase: irregular SiOH 15-40 μm 120 g, Mobile phase: Gradient from 100% DCM, 0% MeOH to 95% DCM, 5% MeOH). The fractions containing product were collected and evaporated to dryness yielding 1.56 g (yield 65%) of intermediate 18.

Preparation of Intermediate 19

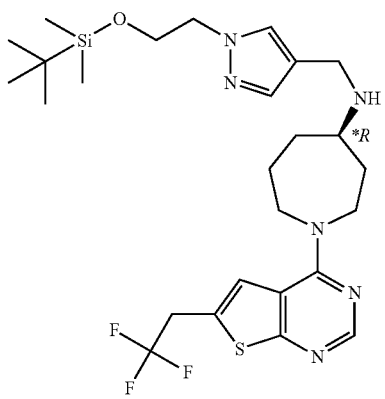 [SMILES: CC(C)(C)[Si](C)(C)OCCn1cc(CN[C@@H]2CCCN(c3ncnc4sc(CC(F)(F)F)cc34)CC2)cn1]

The compound was prepared using an analogous method as described for the preparation of intermediate 17, starting from the respective starting materials intermediate 15 and intermediate 18.

Preparation of Intermediate 20A and 20B

Intermediate 20A

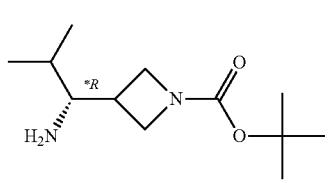

Intermediate 20B

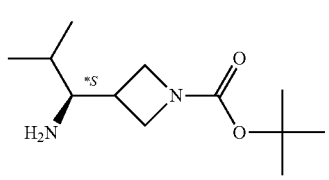

The enantiomers of racemic mixture of ter-Butyl-3-(1-amino-2-methylpropyl)azetidine-1-carboxylate (CAS [1782590-67-3]), (900 mg, 3.94 mmol) were separated using chiral SFC (Stationary phase: Lux Cellulose-2 5 μm 250*30 mm, Mobile phase: 85% $CO_2$, 15% MeOH (0.3% iPrNH$_2$)). The fractions containing product were collected and evaporated to dryness yielding 390 mg (yield 43%) of first eluted enantiomer 20A and 331 mg (yield 37%) of second eluted enantiomer 20B

Preparation of Intermediate 21

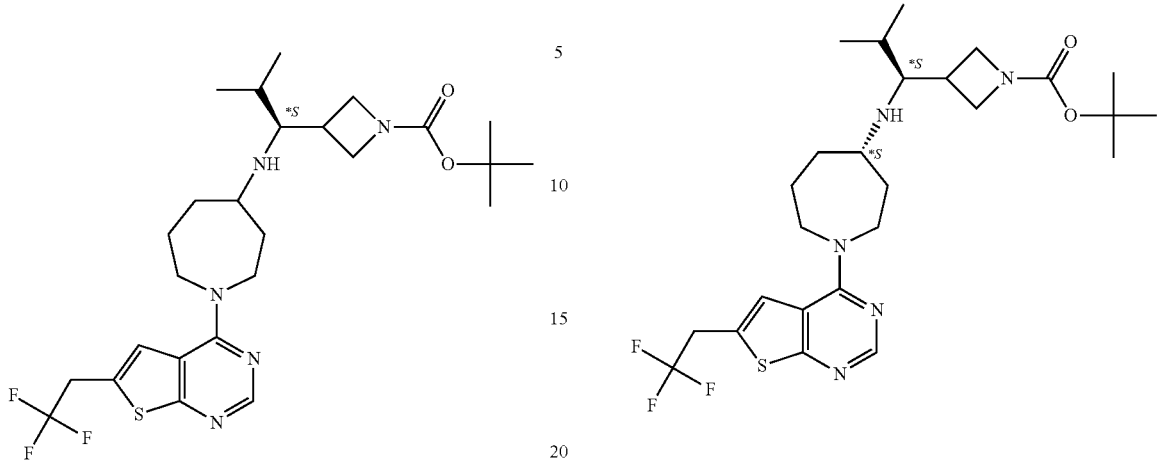

Under N$_2$ flow, a solution of intermediate 3 (473 mg, 1.44 mmol), intermediate 20B (331 mg, 1.45 mmol) and acetic acid (85 µL, 1.49 mmol) in THF (19 mL) was stirred at rt overnight. Then NaBH(OAc)$_3$ (918 mg, 4.33 mmol) was added portion wise and the mixture was stirred at rt for 24 h. The mixture was carefully poured into ice water, basified with NaOH and extracted with EtOAc. The organic layers were combined, dried over MgSO$_4$, filtered and evaporated to dryness giving 1.1 g of crude compound. The residue was purified by chromatography over silica gel (Stationary phase: irregular SiOH 15-40 µm 40 g, Mobile phase: 65% heptane, 5% MeOH, 35% EtOAc). The fractions containing product were collected and evaporated to dryness yielding 565 mg of intermediate 21 (yield 72%).

Preparation of Intermediate 21A and 21B

INTERMEDIATE 21A

INTERMEDIATE 21B

The mixture of diasteromers INTERMEDIATE 21 (240 mg, 0.44 mmol) was separated using chiral SFC (Stationary phase: CHIRACEL OJ-H 5 µm 250*30 mm, Mobile phase: 85% CO$_2$, 15% MeOH (0.3% iPrNH$_2$)). The fractions containing product were collected and evaporated to dryness yielding 84 mg (yield 11%) of first eluted isomer 21A and 97 mg (yield 13%) of second eluted isomer 21B.

Preparation of Intermediate 22

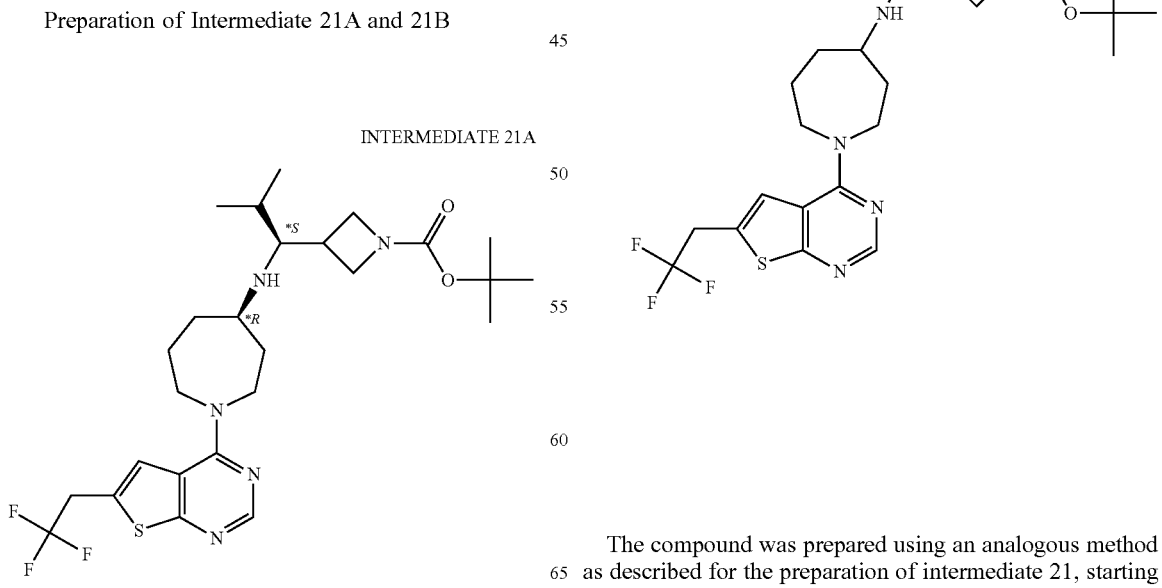

The compound was prepared using an analogous method as described for the preparation of intermediate 21, starting from the respective starting materials intermediate 3 and intermediate 20A Preparation of Intermediate 22A and 22B

INTERMEDIATE 22A

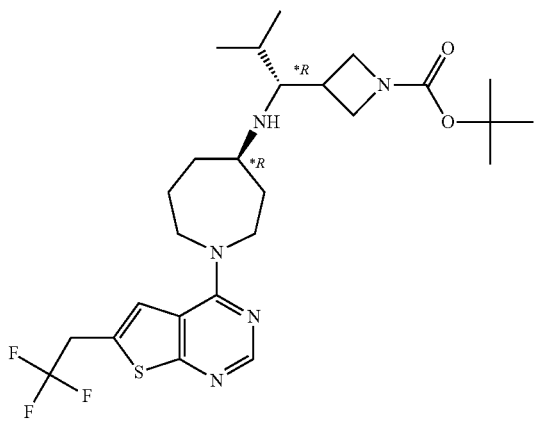 [SMILES: CC(C)[C@@H](NC1CCCN(c2ncnc3sc(CC(F)(F)F)cc23)CC1)C1CN(C(=O)OC(C)(C)C)C1]

INTERMEDIATE 22B

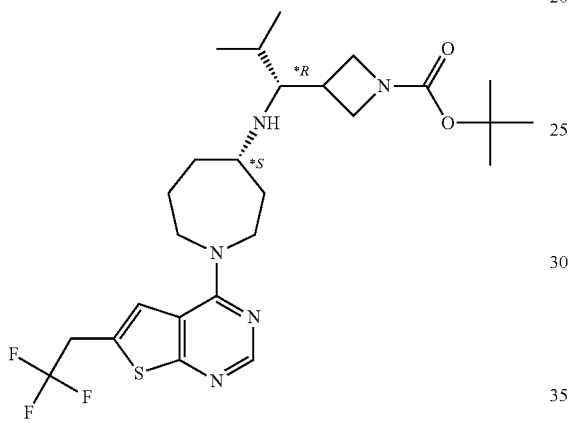

The mixture of diastereomers in INTERMEDIATE 22 (240 mg, 0.44 mmol) was separated using chiral SFC (Stationary phase: CIRALPAK-AD-H 5 min 250*30 mm, Mobile phase: 70% CO$_2$, 30% iPrOH (0.3% iPrNH$_2$)). The fractions containing product were collected and evaporated to dryness yielding 96 mg (yield 11%) of first eluted isomer 22A and 110 mg (yield 12%) of second eluted isomer 22B Preparation of Intermediate 27

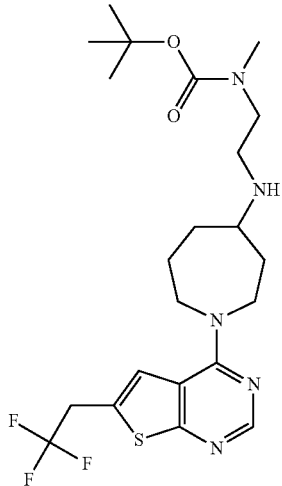 [SMILES: CN(CCNC1CCCN(c2ncnc3sc(CC(F)(F)F)cc23)CC1)C(=O)OC(C)(C)C]

Under nitrogen atmosphere, acetic acid (139 µL; 2.43 mmol) was added at rt to a solution of intermediate 3 (400 mg; 1.21 mmol) in THF (15 mL) followed by addition of N-Boc-N-methylethylenediamine (CAS [121492-06-6]) (423 mg; 2.43 mmol). The mixture was stirred at room temperature for 5 hours then NaBH(OAc)$_3$ (772 mg; 3.64 mmol) was added and the mixture was stirred at rt for 24 h. The mixture was poured into a mixture of ice water and a 10% solution of K$_2$CO$_3$, then extracted with EtOAc, washed with brine and the organic layer was dried over MgSO$_4$, filtered and evaporated to dryness to give 0.6 g or residue. The residue was purified by chromatography over silica gel (Stationary phase: irregular SiOH 15-40 µm 300 g MERCK, Mobile phase: 0.19% NH$_4$OH, 95% DCM, 5% MeOH). The fractions containing product were collected and evaporated to dryness yielding 460 mg (72%) of intermediate 27.

Preparation of Intermediate 28

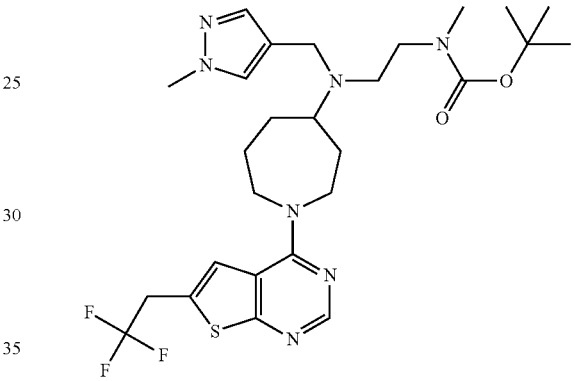

Acetic acid (101 µL; 1.76 mmol) was added under nitrogen atmosphere, at rt to a solution of intermediate 27 (430 mg; 0.88 mmol) and 1-methyl-1H-pyrazole-4-carbaldehyde (CAS [25016-11-9]) (194 mg; 1.76 mmol) in THF (15 mL). The mixture was stirred at rt for 3 hours. Subsequently, NaBH(OAc)$_3$ (561 mg; 2.65 mmol) was added portionwise and the mixture was stirred at rt for 15 hours. The mixture was poured into a mixture of water, and a 10% solution of K$_2$CO$_3$. EtOAc was added and stirred at rt for 15 min and extracted with EtOAc (×2). The organic layers were combined, dried over MgSO$_4$, filtered and evaporated to dryness. The residue was purified by chromatography over silica gel (Stationary phase: irregular SiOH 15-40 µm 24 g GRACE, Mobile phase: Gradient from 0.1% NH$_4$OH, 97% DCM, 3% MeOH to 0.1% NH$_4$OH, 95% DCM, 5% MeOH). The fractions containing product were collected and evaporated to dryness yielding 420 mg (82%) of intermediate 28.

Preparation of Intermediate 33

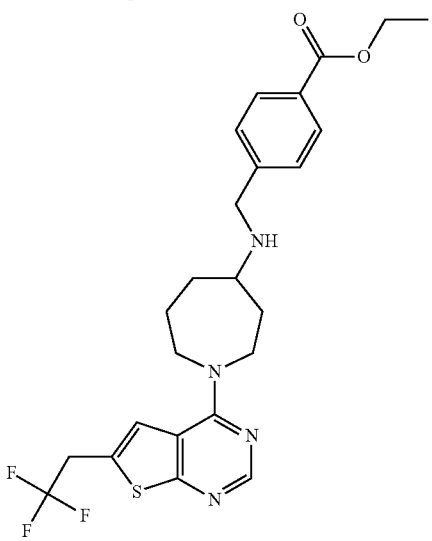 [SMILES: CCOC(=O)c1ccc(CNC2CCCN(c3ncnc4sc(CC(F)(F)F)cc34)CC2)cc1]

Under N$_2$, to a solution of intermediate 3 (255 mg; 0.78 mmol), Ethyl-4(Aminomethyl)Benzoate (277 mg; 1.55 mmol) in a mixture of THF (7 mL) and acetic acid (67 μL; 1.16 mmol) were stirred at rt for 3 h. Then, NaBH(OAc)$_3$ (361 mg; 1.7 mmol) was added and the mixture was stirred at rt overnight. The mixture was poured into ice water and was separated. The aqueous layer was extracted twice with EtOAc. The organic layers were combined, washed with brine then dried over MgSO$_4$, evaporated. The crude (350 mg) was purified by silica gel chromatography (Stationary phase: irregular SiOH 15-40 m 24 g MERCK, Mobile phase: Gradient from 97% DCM, 3% MeOH (+10% NH$_4$OH) to 95% DCM, 5% MeOH (+10% NH$_4$OH)). The fractions containing the product were mixed to give to afford 81 mg (21%) of intermediate 33. The compounds in the Table below were prepared using an analogous method as described for the preparation of intermediate 33, starting from respective starting materials.

| INTERMEDIATE NUMBER | STRUCTURE | YIELD |
|---|---|---|
| Intermediate 32 from intermediate 3 and N-benzyl-2-{[tert-butyl(dimethyl)silyl]oxy} ethanamine (CAS:[227805-74-5] | | 47% |
| Intermediate 34 from intermediate 3 and Dimethylaminobutyl amine (CAS: [3529-10-0]) | | 78% |

Preparation of Intermediate 35

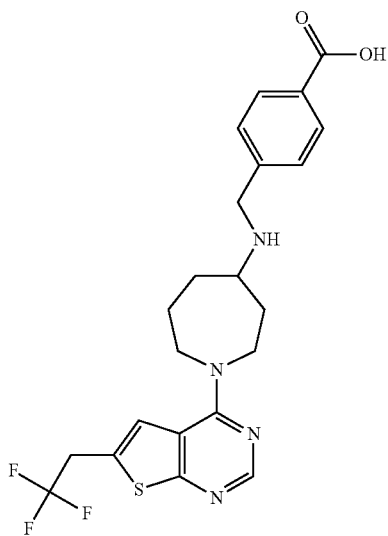 [SMILES: O=C(O)c1ccc(CNC2CCCN(c3ncnc4sc(CC(F)(F)F)cc34)CC2)cc1]

as an HCl salt

A solution of LiOH hydrate (33 mg; 0.79 mmol) was added at rt to a solution of intermediate 33 (65 mg; mmol) in a mixture of THF (4.6 mL) and water (0.5 mL).

The reaction mixture was heated at 60° C. for 24 hours. The reaction mixture was evaporated till dryness. The residue was diluted with water, acidified with HCl 1N and evaporated till dryness to give 107 mg of intermediate 35 as an HCl salt.

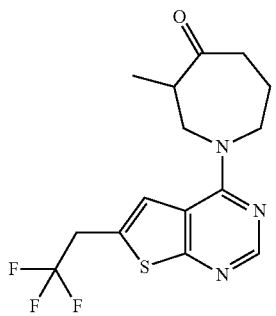 [SMILES: CC1CN(c2ncnc3sc(CC(F)(F)F)cc23)CCCC1=O]

Preparation of Intermediate 42

A mixture of 4-chloro-6-(2,2,2-trifluoroethyl)thieno[2,3-d]pyrimidine (prepared as described in Journal of Medicinal Chemistry (2016), 59(3), 892-913) (CAS[1628317-85-0]) (466 mg, 1.82 mmol), 3-Methyl Azepanone (CAS[748712-34-7]) (255 mg, 2 mmol), and DIEA (0.94 mL, 5.47 mmol) in iPrOH (10 mL) was heated at 90° C. for 5 h. The mixture was cooled to rt, then poured out into water and the product was extracted with EtOAc. The organic layer was separated, washed with brine, dried over MgSO$_4$, filtered, and evaporated to dryness. The residue was purified by chromatography over silica gel (Stationary phase: irregular SiOH-15-40 μm 24 g, Mobile phase: Gradient from 99% DCM, 1% MeOH (+10% NH$_4$OH)) The fractions containing product were collected and evaporated to dryness yielding 65 mg (yield 10%) of pur compound. This fraction was freeze-dried from ACN/water, yielding 44 mg of intermediate 42 as a white powder.

The intermediate in the Table below was prepared using an analogous method as described for the preparation of the intermediate above, starting from the respective starting materials

| INTERMEDIATE NUMBER | STRUCTURE |
|---|---|
| Intermediate 43 (from 4-chloro-6-(2,2,2-trifluoroethyl)thieno[2,3-d]pyrimidine and 5-methylazepan-4-one) | 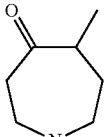 |

Preparation of Intermediate 44 tert-butyl 4-(benzyloxy)azepane-1-carboxylate

NaH (60% dispersion in mineral oil) (89 mg; 2.23 mmol) was added at room temperature to a solution of 1-H-Azepine-1-carboxylic acid, hexahydro-4-hydroxy-1,1-dimethylethyl ester (CAS [1478832-21-2]) (0.4 g; 1.86 mmol) in DMF (7.6 mL). After 30 minutes benzyl bromide (0.221 mL; 1.86 mmol) was added in one portion and the reaction mixture was kept stirring at room temperature overnight. The mixture was poured into ice and extracted with EtOAc. The organic layer was washed with brine, dried over MgSO$_4$, filtered and the solvent was evaporated. The residue was purified by chromatography over silica gel (15-40 μm, 40 g, eluent: heptane/EtOAc: 100/0 to 0/100). The fractions containing product were collected and evaporated to dryness yielding 0.394 g (69%) of intermediate 44.

Preparation of Intermediate 45

4-(benzyloxy)azepane as an HCl Salt

HCl (4N in dioxane) (1.88 mL; 7.5 mmol) was added dropwise at 0° C., to a solution of intermediate 44 (0.382 g; 1.25 mmol) in DCM (8 mL), and the mixture was stirred at rt for 15 h. The reaction was evaporated to dryness, the residue was taken-up with Et$_2$O and the white precipitate was filtered off and dried under vaccum yielding: 0.285 g (94%) of intermediate 45 as an HCl salt.

B. Preparation of the Compounds

Example B1

Preparation of Enantiomers B1A and B1B

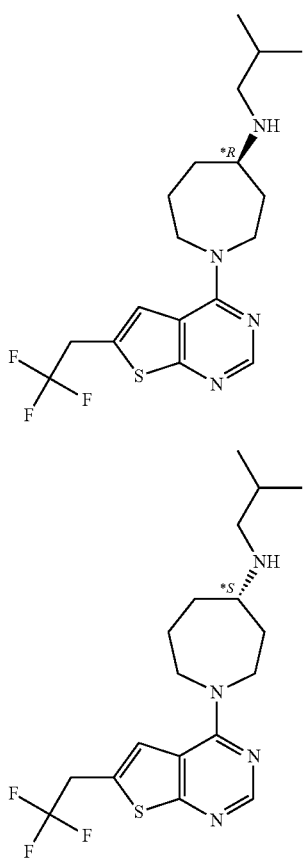

Under N$_2$ flow, a solution of intermediate 3 (158 mg, 0.48 mmol), isobutylamine ([CAS: 78-81-9]) (191 µL, 1.9 mmol) and acetic acid (60 µL, 1.1 mmol) in THF (3 mL) was stirred at rt for 3 h. NaBH(OAc)$_3$ (224 mg, 1.06 mmol) was added portionwise and the mixture was stirred at rt overnight. The mixture was poured into ice water and the mixture was separated, the aqueous layer was extracted with EtOAc (×2). The organic layers were combined, washed with brine then dried over MgSO$_4$ and evaporated. The residue was purified by chromatography over silica gel (stationary phase: irregular SiOH 15-40 µm 24 g MERCK, mobile phase: gradient from 96% DCM, 4% MeOH (+10% NH$_4$OH) to 90% DCM, 10% MeOH (+10% NH$_{40}$H)). The fractions containing product were collected and evaporated to dryness yielding 123 mg (yield 66%) of racemic N-isobutyl-1-(6-(2,2,2-trifluoroethyl)thieno[2,3-d]pyrimidin-4-yl)azepan-4-amine.

The two enantiomers were separated by chiral SFC (Stationary phase: CHIRALCEL OJ-H 5 µm 250×20 mm, mobile phase: 90% CO$_2$, 10% iPrOH (0.3% iPrNH$_2$)). The product containing fractions were collected and evaporated to dryness yielding 47 mg (yield 10%) of first eluted enantiomer A and 48 mg (yield 10%) of second eluted enantiomer B.

Both enantiomers were separately freeze-dried with ACN/water 20/80 to give compound B1A (enantiomer A) (0.041 g) and compound B1B (enantiomer B) (0.051 g).

NMR compound B1A: $^1$H NMR (500 MHz, DMSO-d$_6$) δ ppm 8.33 (s, 1H) 7.60 (s, 1H) 4.08 (q, J=11.0 Hz, 2H) 3.86-3.98 (m, 2H) 3.69-3.85 (m, 2H) 2.61 (br s, 1H) 2.46 (br s, 1H) 2.29 (br d, J=6.6 Hz, 2H) 2.00 (br d, J=6.6 Hz, 2H) 1.51-1.78 (m, 4H) 1.34-1.45 (m, 1H) 0.83 (dd, J=6.5, 3.6 Hz, 6H)

Example B2

Preparation of Compound 3

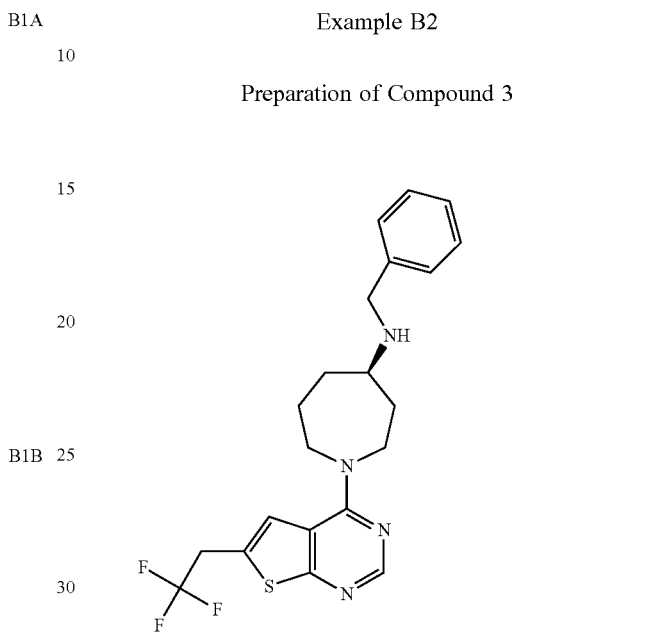

as an HCl salt

A mixture of (R)—N-benzoylazepan-4-amine, intermediate 4 (129 mg, 0.465 mmol), 4-chloro-6-(2,2,2-trifluoroethyl)thieno[2,3-d]pyrimidine (CAS [1628317-85-0]), (118 mg, 0.465 mmol), prepared as described in Journal of Medicinal Chemistry (2016), 59(3), 892-913, and DIEA (0.32 mL, 1.86 mmol) in ACN (5 mL) was stirred at rt overnight. The solution was cooled and the residue was poured into cooled water. K$_2$CO$_3$ (solid) was added, and the mixture was extracted with DCM, the organic layer was dried over MgSO$_4$, filtered and evaporated to dryness. The residue was purified by chromatography over silica gel (stationary phase: irregular bare silica 40 g, mobile phase: gradient from 100% DCM, 0% MeOH to 97% DCM, 3% MeOH, 0.1% NH$_4$OH). The fractions containing product were collected and evaporated to dryness yielding 117 mg (yield 60%) of (R)N-benzyl-1-(6-(2,2,2-trifluoroethyl)thieno[2,3-d]pyrimidin-4-yl)azepan-4-amine. This residue was dissolved in acetone, and converted into hydrochloric acid salt by treatment with HCl (4N in dioxane), the precipitate was filtered and the solid was dried providing 115 mg (yield 48.5%) of Compound 3 C$_{21}$H$_{23}$F$_3$N$_4$S. 1.7 HCl. 1.4H$_2$O, m.p.: 134° C. (Kofler), optical rotation: +59.10 (365 nm, DMF, 20° C., c=3.03 mg/mL).

$^1$H NMR (500 MHz, DMSO-d$_6$) δ ppm 9.22 (br s, 2H) 8.44 (s, 1H) 7.67 (s, 1H) 7.52-7.58 (m, 2H) 7.37-7.44 (m, 3H) 4.07-4.19 (m, 5H) 3.99-4.06 (m, 1H) 3.75-3.86 (m, 211H) 3.20 (br s, 111H) 2.47 (br s, 1H) 2.24 (br d, J=12.3 Hz, 1H) 2.03-2.13 (m, 1H) 1.97 (q, J=9.9 Hz, 1H) 1.80 (br d, J=11.0 Hz, 1H) 1.59-1.71 (m, 1H)

Example B3

Preparation of Compound 4

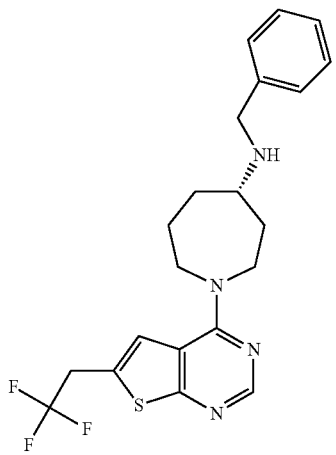 [SMILES: FC(F)(F)Cc1cc2c(N3CCC[C@H](NCc4ccccc4)CC3)ncnc2s1]

as an HCl salt

Similarly prepared as compound 3 starting from (S)—N-benzoylazepan-4-amine, and intermediate 5, was (S)—N-benzyl-1-(6-(6-,2,2-trifluoroethyl)thieno[2,3-d]pyrimidin-4-yl)azepan-4-amine (97 mg, yield 50%). This compound was dissolved in acetone, and converted into hydrochloric acid salt by treatment with HCl (4N in dioxane), the precipitate was filtered and the solid was dried providing 80 mg (yield 34%) of compound 4 $C_{21}H_{23}F_3N_4S$. 1.6 HCl. 1H$_2$O, m.p.: 230° C. (Kofler), optical rotation: −60.6° (365 nm, DMF, 20° C., c=2.84 mg/mL).

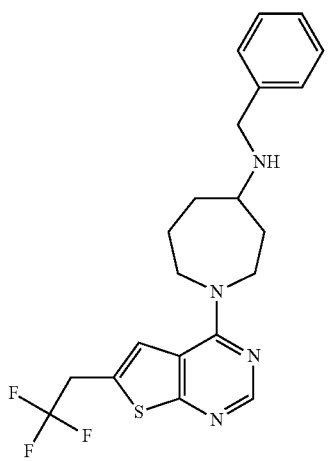 [SMILES: FC(F)(F)Cc1cc2c(N3CCCC(NCc4ccccc4)CC3)ncnc2s1]

Example B4

Preparation of Compound 3A and Alternative Preparation of Compounds 3 and 4

A mixture of N-benzoylazepan-4-amine (166 mg, 0.81 mmol), (CAS[1565450-95-4]), 4-chloro-6-(2,2,2-trifluoroethyl)thieno[2,3-d]pyrimidine (CAS[1628317-85-0]), (186 mg, 0.74 mmol), prepared as described in Journal of Medicinal Chemistry (2016), 59(3), 892-913, and DIPEA (0.26 mL, 1.48 mmol) in iPrOH (5 mL) was heated at 90° C. overnight. The solution was cooled to rt then concentrated, and the residue was taken up with DCM, the organic layer was washed with water, dried over MgSO$_4$, filtered and evaporated to dryness. The residue was purified by chromatography over silica gel (stationary phase: irregular SiOH 15-40 µm 24 g MERCK, mobile phase: gradient 95% DCM, 5% MeOH (+10% NH$_4$OH)). The fractions containing product were collected and evaporated to dryness yielding 223 mg (yield 72%) of racemic N-benzyl-1-(6-(2,2,2-trifluoroethyl)thieno[2,3-d]pyrimidin-4-yl)azepan-4-amine compound 3A. The two enantiomers were separated by chiral SFC (stationary phase: CHIRALCEL OJ-H 5 µm 250×20 mm, mobile phase: 80% CO$_2$, 20% EtOH (0.3% iPrNH$_2$)). The product containing fractions were collected and evaporated to dryness yielding respectively 103 mg (yield 33%) of the first eluted enantiomer A that corresponds to compound 3 of absolute configuration (R) and 102 mg (yield 33%) of the second eluted enantiomer B that corresponds to compound 4 of absolute configuration (S).

Each enantiomer was separately dissolved in acetone, and converted into hydrochloric acid salt by treatment with HCl (4N in dioxane), the precipitate was filtered and the solid was dried providing 100 mg of compound 3 $C_{21}H_{23}F_3N_4S$. 3.4 HCl. 2.7H$_2$O, m.p.: 130° C. (Kofler; gum) and 98 mg of compound 4 $C_{21}H_{23}F_3N_4S$. 2.4 HCl. 1H$_2$O, m.p.: 224° C. (Kofler).

Alternative Preparation of Compound 3A

Under N$_2$ flow, at rt, a solution of intermediate 3 (1.5 g, 4.55 mmol), Benzylamine, (1.49 mL, 13.66 mmol), and acetic acid (0.52 mL; 9.11 mmol) in MeOH (15 mL) and DCE (15 mL) was stirred at rt for 2 h. Then NaBH(OAc)$_3$ (2.12 g, 10.02 mmol) was added and the mixture was stirred at rt for 48 h. The solution was poured out into cooled water, basified with NaOH 3N. The product was extracted with DCM. The organic layer was washed with brine, dried over MgSO$_4$, filtered and evaporated to dryness. The residue was purified by chromatography over silica gel (Stationary phase: irregular SiOH 15-40 µm 24 g Mobile phase: 96% DCM, 4% MeOH (+10% NH$_4$OH)). The fractions containing the product were collected and evaporated to dryness yielding 1.9 g of compound 3A (yield 99%).

The compounds in the Table below were prepared using an analogous method as described for the preparation of compound above, starting from the respective starting materials

| COMPOUND NUMBER | STRUCTURE |
|---|---|
| Compound 5 and 5a (from intermediate 7) | ![structure] obtained as free base (compound 5a) and as an HCl salt (compound 5) (•2.5 HCl•1.2 H$_2$O) |

Example B5

Preparation of Compound 6

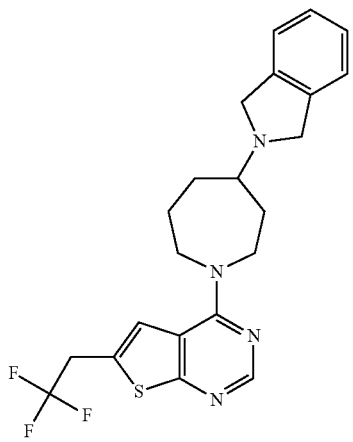 [SMILES: FC(F)(F)Cc1cc2c(N3CCCC(N4Cc5ccccc5C4)CC3)ncnc2s1]

Under $N_2$ flow, a solution of intermediate 3 (250 mg, 0.76 mmol), isoindoline (CAS[496-12-8]) (361 mg, 3.04 mmol) and acetic acid (96 µL, 1.67 mmol) in THF (10 mL) was stirred at rt for 2 h. Then $NaBH(OAc)_3$ (354 mg, 1.67 mmol) was added and the mixture was stirred at rt overnight. The mixture was carefully poured into ice water and extracted with EtOAc. The organic layers were combined, washed with brine, dried over $MgSO_4$, filtered and evaporated to dryness. The residue was purified by chromatography over silica gel (Stationary phase: irregular SiOH 15-40 µm 24 g MERCK, Mobile phase: Gradient from 0.1% $NH_4OH$, 98% DCM, 2% MeOH to 0.1% $NH_4OH$, 95% DCM, 5% MeOH). The fractions containing product were collected and evaporated to dryness yielding 130 mg of compound 6 (yield 40%). This fraction was crystallized from $Et_2O$, the precipitate was filtered off and dried under vacuum giving 40 mg of compound 6, M.P.=111° C. (DSC).

The compounds in the Table below were prepared using an analogous method as described for the preparation of compound above, starting from the respective starting materials

| COMPOUND NUMBER | STRUCTURE | YIELD |
|---|---|---|
| Compound 7 (from intermediate 3) | as an HCl salt | |
| Compound 8 (from intermediate 3) | •as an HCl salt | |

-continued
| COMPOUND NUMBER | STRUCTURE | YIELD |
|---|---|---|
| Compound 9 (from intermediate 3) | 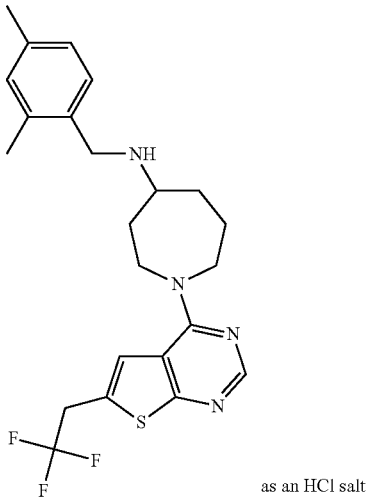 [SMILES: Cc1ccc(CNC2CCCN(c3ncnc4sc(CC(F)(F)F)cc34)CC2)c(C)c1] as an HCl salt | |
| Compound 12 (from intermediate 3) M.P = 94° C. (Kofler) | 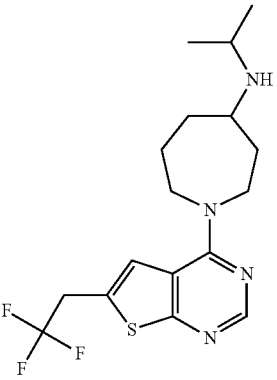 [SMILES: CC(C)NC1CCCN(c2ncnc3sc(CC(F)(F)F)cc23)CC1] | 53% |
| Compound 52 (from intermediate 3 and 2S-2-amino-N,3-dimethylbutanamide CAS [87105-26-8]) | 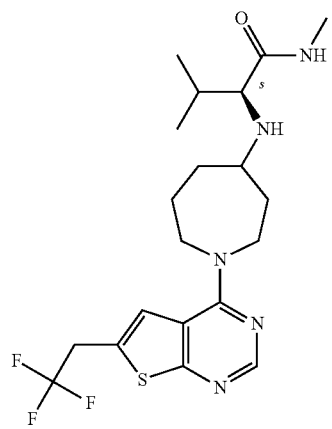 [SMILES: CNC(=O)[C@@H](NC1CCCN(c2ncnc3sc(CC(F)(F)F)cc23)CC1)C(C)C] | 47% |

-continued

| COMPOUND NUMBER | STRUCTURE | YIELD |
|---|---|---|
| Compound 53 (from intermediate 3 and Benzyl[3-(Dimethylamino)propyl]amineCAS: [32857-22-0]) | 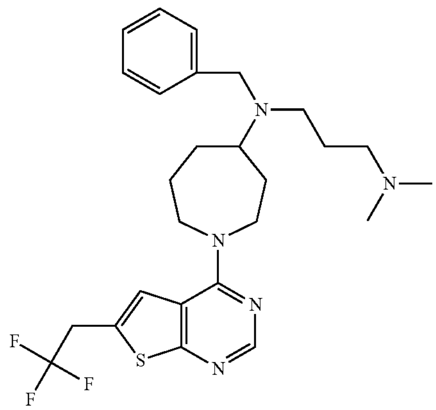 [SMILES: CN(C)CCCN(Cc1ccccc1)C1CCCN(c2ncnc3sc(CC(F)(F)F)cc23)CC1] | 7% |
| Compound 54 (from intermediate 3 and 1-(1-Methyl-H-pyrazol-4-yl)ethylamine, CAS: [911788-33-5]) | 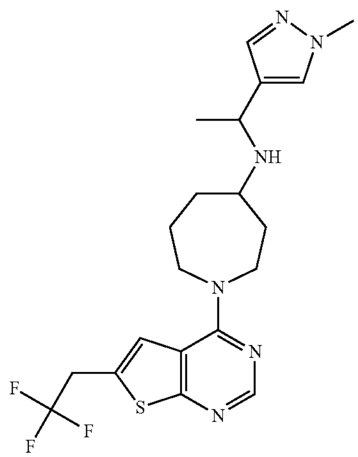 [SMILES: CC(NC1CCCN(c2ncnc3sc(CC(F)(F)F)cc23)CC1)c1cnn(C)c1] | 85% |
| Compound 55 (from intermediate 3 and 1-tetrahydro-2H-pyran-4-ylmethanamine, CAS: [130290-79-8]) | as an HCl salt | |

| COMPOUND NUMBER | STRUCTURE | YIELD |
|---|---|---|
| Compound 56 (from intermediate 3 and N'-Benzyl-N,N-Dimethylethylene-diamine, CAS: [109-55-7]) | 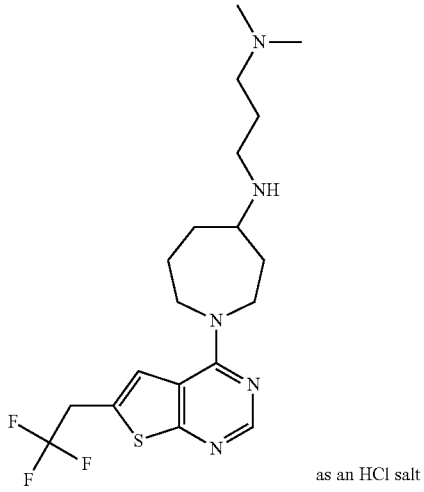 [SMILES: CN(C)CCCNC1CCCN(c2ncnc3sc(CC(F)(F)F)cc23)CC1] as an HCl salt | |
| Compound 57 (from intermediate 3 and N'-Benzyl-N,N-dimethylethylene-diamine, CAS: [103-55-9]) | 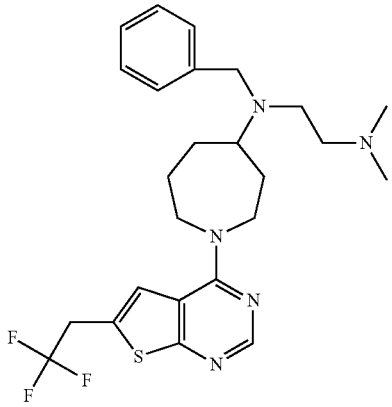 [SMILES: CN(C)CCN(Cc1ccccc1)C1CCCN(c2ncnc3sc(CC(F)(F)F)cc23)CC1] | 54% |
| Compound 58 (from Compound 11 and isobutyraldehyde, CAS: [78-84-2]) | 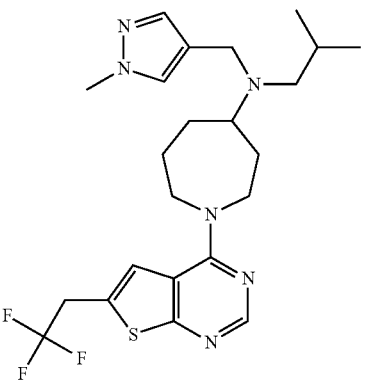 [SMILES: CC(C)CN(Cc1cnn(C)c1)C1CCCN(c2ncnc3sc(CC(F)(F)F)cc23)CC1] | 62% |

| COMPOUND NUMBER | STRUCTURE | YIELD |
|---|---|---|
| Compound 59 (from compound 3A and oxetan-3-one, CAS: [6704-31-0]) | 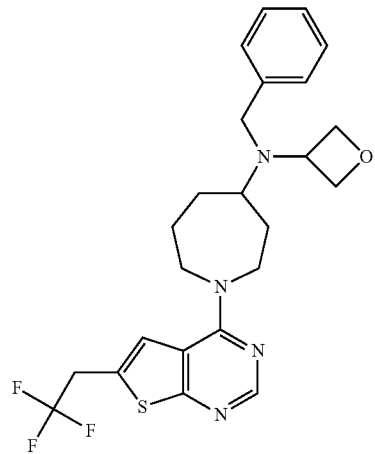 [SMILES: FC(F)(F)Cc1cc2c(N3CCCC(N(Cc4ccccc4)C4COC4)CC3)ncnc2s1] | 34% |
| Compound 60 (from compound 3A and 1-Methyl-1H-Pyrazole-4-carbaldehyde, CAS [25016-11-9]) | 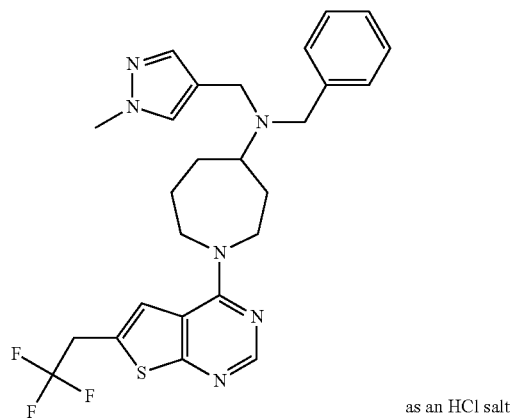 [SMILES: Cn1cc(CN(Cc2ccccc2)C2CCCN(c3ncnc4sc(CC(F)(F)F)cc34)CC2)cn1] as an HCl salt | |
| Compound 61 (from intermediate 34 and 1-Methyl-1H-Pyrazole-4-Carbaldehyde, CAS: [25016-11-9]) | 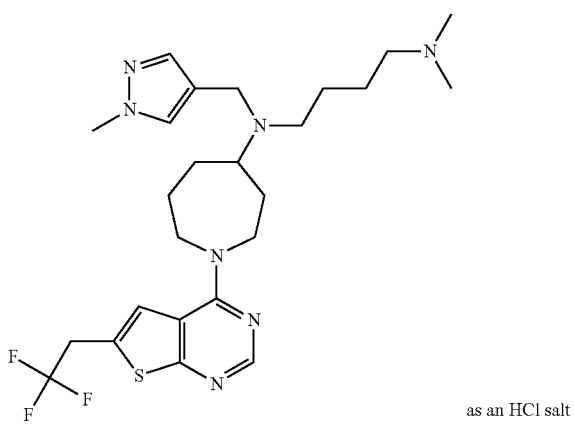 [SMILES: CN(C)CCCCN(Cc1cnn(C)c1)C1CCCN(c2ncnc3sc(CC(F)(F)F)cc23)CC1] as an HCl salt | |

-continued
| COMPOUND NUMBER | STRUCTURE | YIELD |
|---|---|---|
| Compound 62 (from intermediate 3 and 3-dimethylaminopropyl amine, CAS [109-55-7]) | 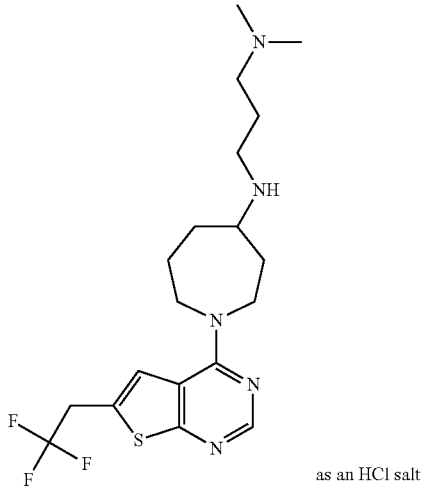 [SMILES: CN(C)CCCNC1CCCN(c2ncnc3sc(CC(F)(F)F)cc23)CC1] as an HCl salt | |
| Compound 63 (from compound 62 and 1-Methyl-1H-Pyrazole-4-Carbaldehyde, CAS [25016-11-9]) | 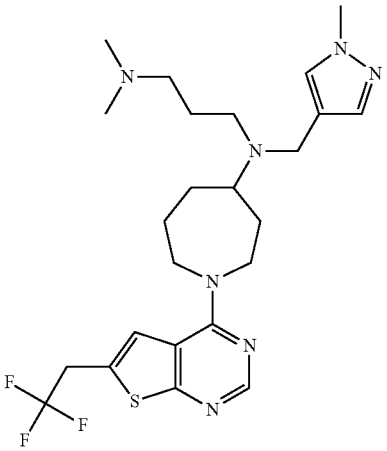 as an HCl salt | |

Example B6

Preparation of Compound 10a

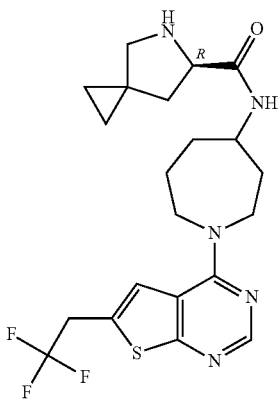

as an HCl salt

HCl (0.45 mL, 1.81 mmol, a 4M solution in dioxane) was added dropwise, at 5° C., to a solution of intermediate 12A (100 mg, 0.18 mmol) in DCM (3 mL), and the mixture was stirred at rt for 15 h. The reaction mixture was evaporated to dryness, the residue was taken-up with Et$_2$O and the solvent was again evaporated to dryness (×2) to give a solid residue (60 rag) of compound 10A as an HCl salt (M.P=220° C. Kofler).

The compound in the Table below was prepared using an analogous method as described for the preparation of compound above, starting from the respective starting materials

| COMPOUND NUMBER | STRUCTURE |
|---|---|
| Compound 10B (from intermediate 12B) M.P = 205° C. (Kofler) | as an HCl salt |

Example B7

Preparation of Compound 11

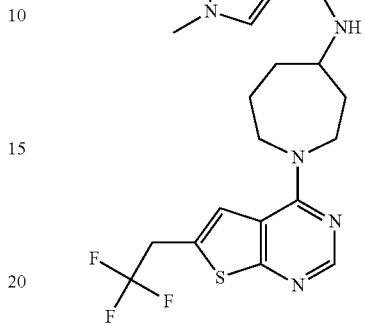

1-Methyl-1H-pyrazole-4-carbaldehyde (CAS: [25016-11-9]) (100 mg, 0.9 mmol) was added dropwise at 20° C., to a solution of intermediate 9 (300 mg, 0.9 mmol) and Et$_3$N (0.23 mL, 1.64 mmol) in MeOH (5 mL). The mixture was stirred at rt for 4 h. The mixture was cooled to 0° C. then NaBH$_4$ (47 mg, 1.23 mmol) was added portionwise and the mixture was stirred at rt for 15 h. The mixture was poured into ice water containing NH$_4$Cl 10%, and extracted with DCM three times. The organic layers were gathered, washed with brine, dried over MgSO$_4$, filtered and evaporated to dryness. The residue was purified by chromatography over silica gel (Stationary phase: irregular SiOH 15-40 μm 24 g GRACE, Mobile phase: Gradient from 0. 1% NH$_4$OH, 97% DCM, 3% MeOH to 0. 1% NH$_4$OH, 95% DCM, 5% MeOH). The fractions containing product were collected and evaporated to dryness yielding 140 mg (yield 40%) of compound 11.

The compound in the Table below was prepared using an analogous method as described for the preparation of compound 11, starting from the respective starting material

| COMPOUND NUMBER | STRUCTURE |
|---|---|
| Compound 69 (from intermediate 14 and 4-pyrimidinecarboxaldehyde CAS[2435-50-9]) | 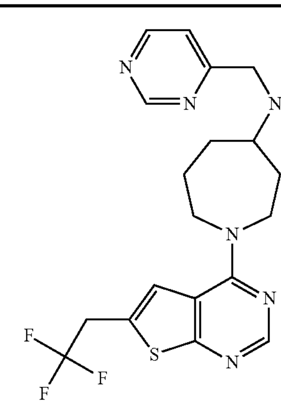 |

Example B8

PREPARATION OF COMPOUND 11A AND 11B

Co. No. 11A

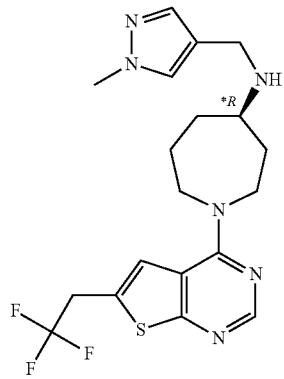

Co. No. 11B

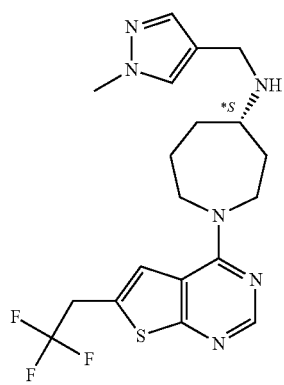 [SMILES: Cn1cc(CNC2CCCN(c3ncnc4sc(CC(F)(F)F)cc34)CC2)cn1]

(as in HCl salt)

The enantiomers of racemic mixture of compound 11 (135 mg) were separated using chiral SFC (Stationary phase: Chiralpak AD-H 5 μm 250*30 mm, Mobile phase: 60% $CO_2$, 40% iPrOH (0.3% iPrNH$_2$)). The fractions containing product were collected and evaporated to dryness yielding 62 mg (yield 46%) of first eluted enantiomer Compound 11A and 65 mg (yield 48%) of second eluted enantiomer (the free base of Compound 11B). Compound 11A was freeze-dried with acetonitrile/water (20/80) to give 46 mg of compound 11A. The free base of compound 11B was dissolved in 2 mL ACN, HCl 6N in iPrOH (2 eq) were added dropwise at 10° C., then Et$_2$O. The mixture was triturated, filtered, and dried yielding 25 mg of compound 11B (as an HCl salt).

The compounds in the Table below were prepared using an analogous method as described for the preparation of compound above, starting from the respective starting materials

| COMPOUND NUMBER | STRUCTURE |
| --- | --- |
| Compound 13A (from intermediate 3) | 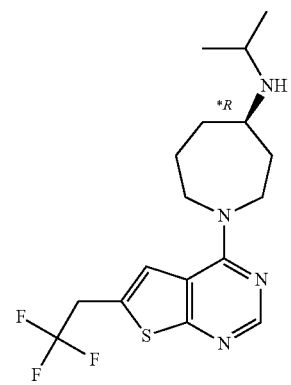 [SMILES: CC(C)N[C@@H]1CCCN(c2ncnc3sc(CC(F)(F)F)cc23)CC1] |
| Compound 13B (from intermediate 3) | 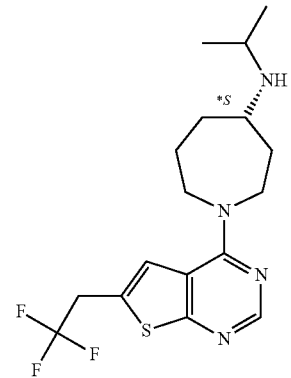 |
| Compound 7A and compound 7B From basic neutralization and SFC separation of compound 7 (Stationary phase: CHIRALPAK AD-H 5 μm 250*30 mm, Mobile phase: 55% $CO_2$, 45% iPrOH(0.3% iPrNH$_2$)) | 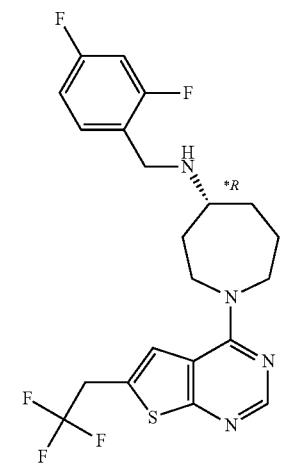 Compound 7A |

| COMPOUND NUMBER | STRUCTURE |
|---|---|
| | Compound 7B 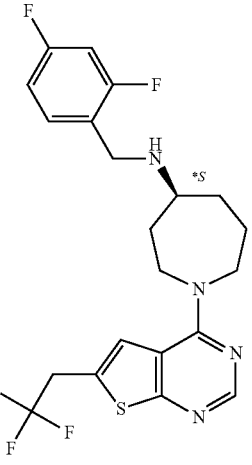 |
| Compound 9A and compound 9B<br>From basic neutralization and SFC separation of compound 9(Stationary phase: CHIRALPAK AD-H 5 μm 250*30 mm, Mobile phase: 55% CO₂, 45% iPrOH(0.3% iPrNH₂)) | Compound 9A 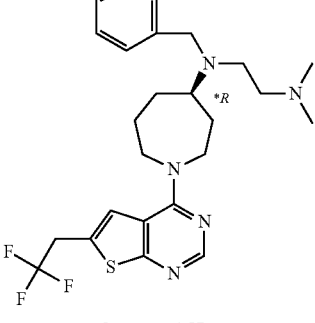 |
| | Compound 9B 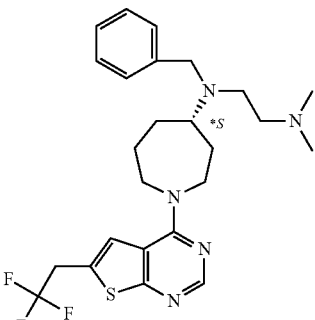 |

| COMPOUND NUMBER | STRUCTURE |
|---|---|
| Compound 57A and compound 57B from SFC separation of compound 57 (Stationary phase: CHIRALPAK AD-H 5 μm 250*30 mm, Mobile phase: 80% CO₂, 20% iPrOH(0.3% iPrNH₂)) | Compound 57A (as an HCl salt) 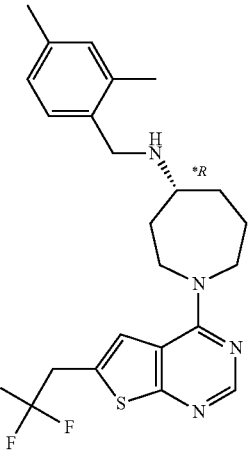 |
| | Compound 57B (as an HCl salt) |
| Compound 58A and compound 58B from SFC separation of compound 58 (Stationary phase: Lux Cellulose-2 5 μm 250*21.2 mm, Mobile phase: 60% CO₂, 40% MeOH(0.3% iPrNH₂)) | Compound 58A (as an HCl salt) 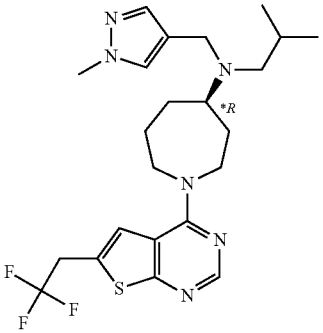 |
| | Compound 58B (as an HCl salt) 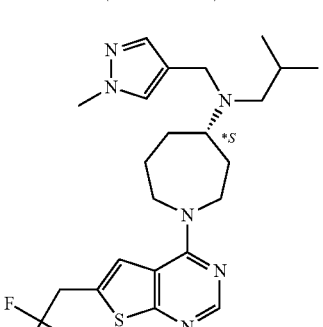 |

| COMPOUND NUMBER | STRUCTURE |
|---|---|
| Compound 59A and compound 59B From SFC separation of compound 59 (Stationary phase: CHIRALPAK AD-H 5 μm 250*30 mm, Mobile phase: 60% CO$_2$, 40% MeOH(0.3% iPrNH$_2$)) | 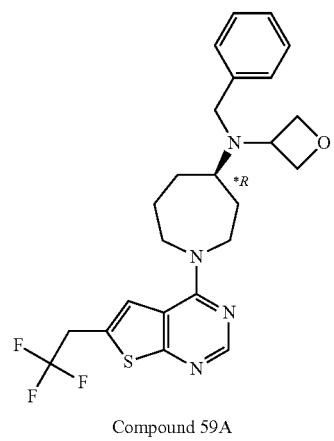 [SMILES: FC(F)(F)Cc1cc2c(N3CCC[C@@H](N(Cc4ccccc4)C4COC4)CC3)ncnc2s1]<br>Compound 59A |
| | 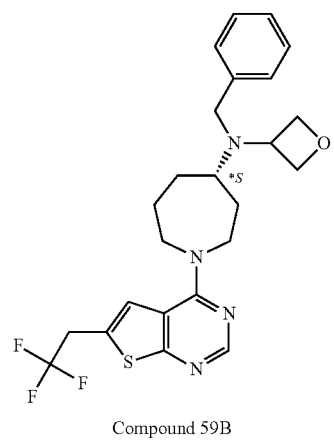 [SMILES: FC(F)(F)Cc1cc2c(N3CCC[C@H](N(Cc4ccccc4)C4COC4)CC3)ncnc2s1]<br>Compound 59B |
| Compound 60A and compound 60B From SFC separation of compound 60 (Stationary phase: Lux Cellulose-2 5 μm 250*30 mm, Mobile phase: 50% CO$_2$, 50% MeOH(0.3% iPrNH$_2$)) | 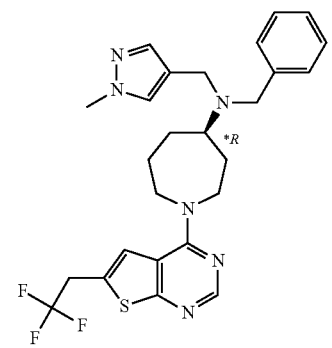<br>Compound 60A (as an HCl salt) |

| COMPOUND NUMBER | STRUCTURE |
|---|---|
| | 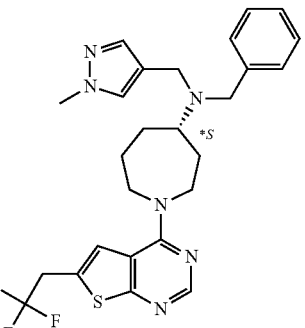<br>Compound 60B (as an HCl salt) |
| Compound 67A and compound 67B From SFC separation of compound 67 (Stationary phase: CHIRALPAK AD-H 5 μm 150*30 mm, Mobile phase: 87% CO$_2$, 13% MeOH(0.3% iPrNH$_2$)) | 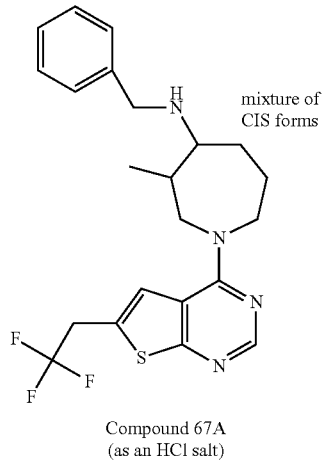 [SMILES: CC1CN(c2ncnc3sc(CC(F)(F)F)cc23)CCCC1NCc1ccccc1]<br>Compound 67A (as an HCl salt) |
| | 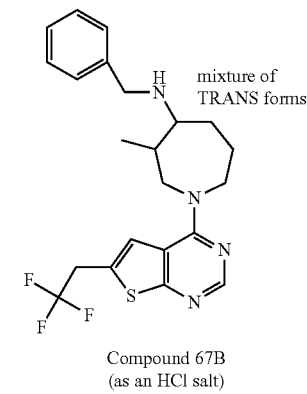 [SMILES: CC1CN(c2ncnc3sc(CC(F)(F)F)cc23)CCCC1NCc1ccccc1]<br>Compound 67B (as an HCl salt) |

NMR compound 9B: $^1$H NMR (500 MHz, DMSO-d$_6$) δ ppm 8.90 (br s, 2H) 8.41 (s, 1H) 7.67 (s, 1-H) 7.35 (d, J=7.6 Hz, 1H) 6.96-7.15 (m, 2H) 3.97-4.25 (m, 6H) 3.81-3.91 (m, 2H) 3.33 (br s, 1H) 2.46 (br s, J=1.9 Hz, 1H) 2.32 (s, 3H) 2.27 (s, 4H) 2.06-2.15 (m, 1H) 1.98 (q, J=10.1 Hz, 1H) 1.84 (br d, J/=9.5 Hz, 1H) 1.66 (q, J=11.2 Hz, 1H)

NMR compound 7B: $^1$H NMR (500 MHz, DMSO-d$_6$) δ ppm 9.60 (br s, 2H) 8.56 (br s, 1H) 7.83 (br d, 1=6.6 Hz, 1H) 7.74 (br s, 1H) 7.34 (br t, 1=8.8 Hz, 1H) 7.18 (br s, 1H) 3.99-4.29 (m, 6H) 3.85 (br s, 2H) 3.30 (br s, 1H) 2.41-2.49 (m, 1H) 2.26 (br s, 1H) 1.93-2.17 (m, 2H) 1.84 (br d, J=8.8 Hz, 1H) 1.71 (br d, =11.3 Hz, 1H)

Example B9

Preparation of Compound 14A and Compound 14B

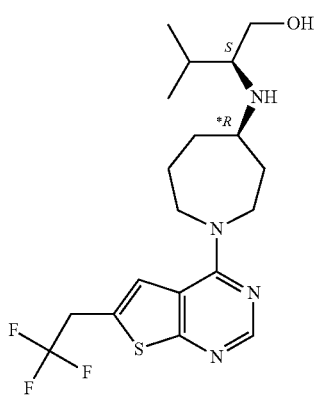

Co. No. 14A

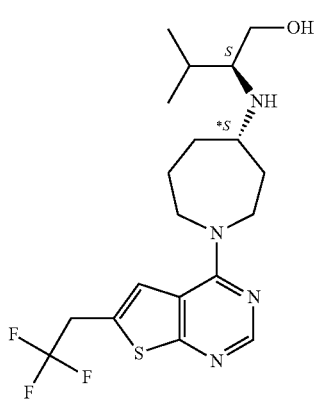

Co. No. 14B

Under N$_2$ flow, a solution of intermediate 13 (82 mg, 0.18 mmol) in THF (3 mL) was added dropwise to a solution of lithium aluminium hydride (6.8 mg, 0.18 mmol) in THF (2 mL) at 5° C. The mixture was stirred for 4 h at 5° C. EtOAc was added dropwise to the solution followed by slow addition of water. The reaction mixture was extracted with EtOAc, the organic layer was washed with water, dried over MgSO$_4$, filtered and evaporated till dryness. The residue was purified by chromatography over silica gel (Stationary phase: irregular bare silica 24 g, Mobile phase: 0.5% NH$_4$OH, 95% DCM, 5% MeOH). The product containing fractions were collected and evaporated to dryness yielding 29 mg (yield 39%) of racemic mixture. The mixture was separated using chiral SFC (Stationary phase: CHIRALPAK AD-H 5 μm 250×20 mm, Mobile phase: 75% CO$_2$, 25% iPrOH (0.3% iPrNH$_2$)). The fractions containing product were collected and evaporated to dryness yielding 10 mg (yield 46%) of first eluted isomer A and 10 mg (yield 48° %) of second eluted isomer B.

Isomer A was freeze-dried with ACN/water 20/80 to give 0.009 g (12%0) of compound 14A.

Isomer B was freeze-dried with ACN/water 20/80 to give 0.008 g (11%) of compound 14B.

Example B10

Preparation of Compound 15

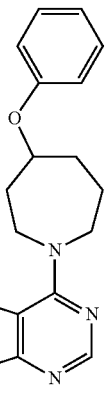

Under N$_2$ flow, at 0° C., DIAD (0.219 mL; 1.11 mmol) was added to a solution of intermediate 2 (0.3 g, 0.905 mmol), phenol (CAS: [108-95-2]), (102 mg, 1.09 mmol) and PPh$_3$ (371 mg; 1.42 mmol) in THF (8 mL). The mixture was allowed to reach rt and was stirred overnight. The reaction mixture was evaporated to dryness.

The crude product was purified by column chromatography over silica gel (eluent: heptane/EtOAc from 1/0 to 3/1). The desired fraction was collected and concentrated to give 0.211 g of crude compound which was purified by chromatography via reverse phase (stationary phase: YMC-actus Triart-C18 10 μm 30*150 mm, mobile phase: gradient from 40% NH$_4$HCO$_3$ 0.2%, 60% ACN to 0% NH$_4$HCO$_3$ 0.2%, 100% ACN). The product containing fractions were collected and evaporated to dryness to give 0.145 g (yield 39%) of product, which was crystallized from DIPE under sonication, the precipitate was filtered and dried, yielding: 0.095 g (yield 26%) of compound 15.

Example B11

Preparation of Compound 16

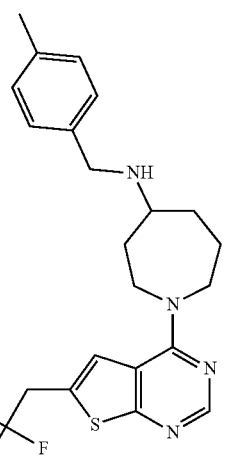

as an HCl salt

Under N₂ flow, a solution of intermediate 3 (200 mg, 0.544 mmol), 4-methylbenzylamine (CAS[104-84-7]) (66 mg, 0.544 mmol), and NaBH(OAc)₃ (224 mg, 1.06 mmol) in DCE (10 mL) was stirred at rt overnight. A saturated NaHCO₃ solution (10 mL) and DCM (10 mL) were added, the mixture was separated, the aqueous layer was extracted with DCM (10 mL×2). The organic layers were combined, washed with water then dried over Na₂SO₄ and evaporated giving 300 mg of crude compound. The residue was purified by chromatography over silica gel (stationary phase: Kromasil 150*25 mm*10 μm, mobile phase: gradient from 47% water (0.05% ammonia hydroxide v/v), 53% ACN to 37% water (0.05% ammonia hydroxide v/v), 63% ACN). The product containing fractions were collected and evaporated to dryness, the residue was dissolved in ACN (3 mL), water (20 mL) and HCl (12M, 0.15 mL) were slowly added in turn. The clear solvent was freeze-dried yielding 250 mg (yield 97%) of compound 16 as an HCl salt. (m.p.: 262-264° C.).

1H NMR (400 MHz, DMSO-d₆) δ ppm 9.55 (br s, 2H), 8.57 (s, 1H), 7.74 (s, 1H), 7.46 (br d, J=7.5 Hz, 2H), 7.17 (br d, J=7.5 Hz, 2H), 4.15 (br d, J=11.0 Hz, 6H), 3.83 (br d, J=9.7 Hz, 2H), 3.14 (br d, J=13.2 Hz, 1H), 2.48-2.38 (m, 1H), 2.28 (s, 4H), 2.14-1.96 (m, 2H), 1.84-1.71 (m, 2H).

The compounds in the Table below were prepared using an analogous method as described for the preparation of compound above, starting from the respective starting materials

| COMPOUND NUMBER | STRUCTURE |
|---|---|
| Compound 17 (from intermediate 3 and 3-(methylaminomethyl)benzylamine, CAS [1035316-05-2]) | 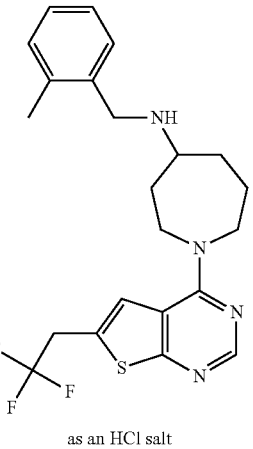<br>as an HCl salt |
| Compound 18 (from intermediate 3 and 2-methoxy-5-methylphenyl)methanamine hydrochloride, CAS: [102439-19-0]) | 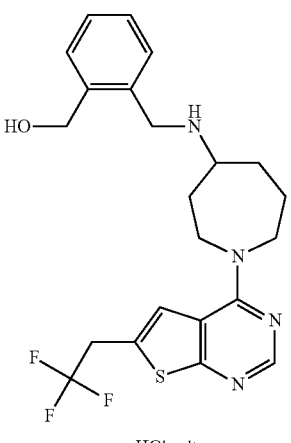<br>as an HCl salt |
| Compound 19 (from intermediate 3 and 2-methylbenzylamine, CAS: [100-81-2]) | 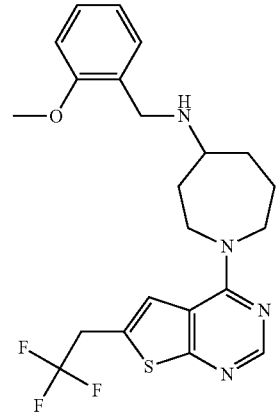<br>as an HCl salt |
| Compound 21 (from intermediate 3 and 2-hydroxybenzylamine, CAS: [932-30-9]) | 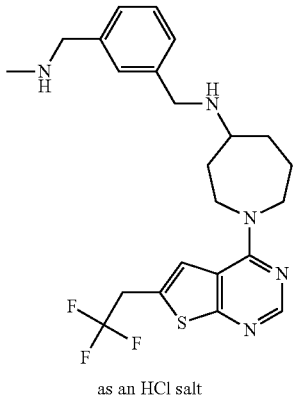 [SMILES: CNCc1cccc(CNC2CCCN(c3ncnc4sc(CC(F)(F)F)cc34)CC2)c1]<br>as an HCl salt |
| Compound 22 (from intermediate 3 and 2-methoxybenzylamine, CAS [6850-57-3]) | 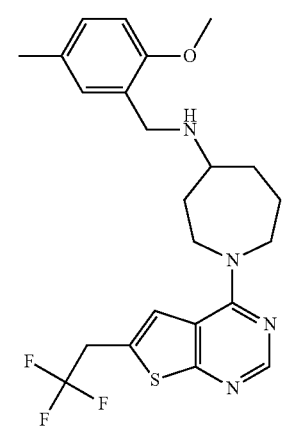<br>as an HCl salt |

| COMPOUND NUMBER | STRUCTURE |
|---|---|
| Compound 23 (from intermediate 3 and 3-methylbenzylamine, CAS: [100-81-2]) | 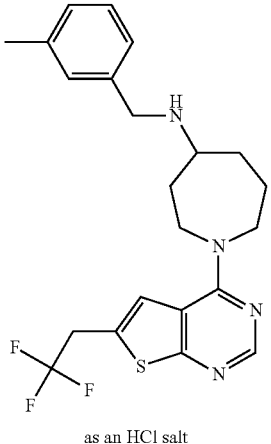 [SMILES: Cc1cccc(CNC2CCCN(c3ncnc4sc(CC(F)(F)F)cc34)CC2)c1] as an HCl salt |
| Compound 24 (from intermediate 3 and 3-fluorobenzylamine, CAS [100-82-3]) | 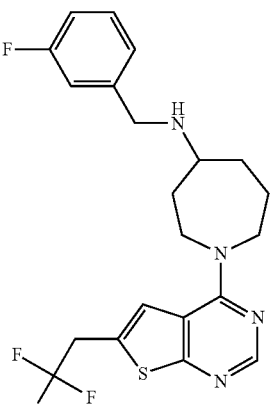 as an HCl salt |

Example B12

Preparation of Compound 26

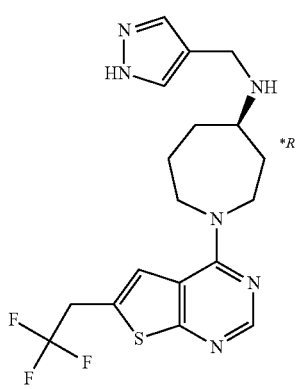 [SMILES: FC(F)(F)Cc1cc2c(N3CCC[C@@H](NCc4cn[nH]c4)CC3)ncnc2s1]

as an HCl salt

HCl (0.74 mL, 2.94 mmol, a 4M solution in dioxane) was added dropwise, at 5° C. to a solution of intermediate 17 (150 mg, 0.29 mmol) in DCM (5 mL), and the mixture was stirred at rt for 4 h. The reaction mixture was evaporated to dryness, the residue was taken-up with $Et_2O$, filtered off and dried under vaccum overnight to give a precipitate (69 mg) of compound 26 as an HCl salt (m.p.=156° C. (Kofler), optical rotation: +40.24° (365 nm, DMF, 20° C., c=2.79 mg/mL)).

$^1$H NMR (400 MHz, DMSO-$d_6$) δ ppm 9.18 (br s, 2H) 8.52 (s, 1H) 7.79 (s, 2H) 7.71 (s, 1H) 3.95-4.25 (m, 6H) 3.62-3.91 (m, 2H) 3.15 (br s, 1H) 2.43 (br s, 1H) 2.15-2.26 (m, 1H) 2.03-2.13 (m, 1H) 1.74-1.99 (m, 2H) 1.55-1.72 (m, 1H)

Example B13

Preparation of Compound 27

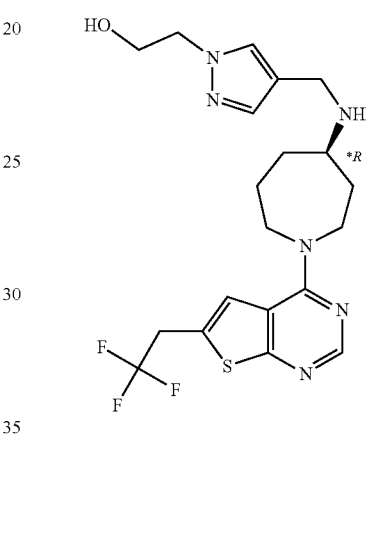

At rt, TBAF (0.35 mL; 0.35 mmol, IM in THF) was added dropwise to a solution of intermediate 19 (200 mg; 0.35 mmol) in THF (10 mL) and the reaction mixture was stirred at room temperature for 5 h.

The reaction mixture was poured into a 10% aqueous solution of $K_2CO_3$ and extracted with EtOAc. The organic layer was washed with 10% aqueous $K_2CO_3$ (2×30 mL), water (30 mL) and brine (30 mL), dried over $MgSO_4$, filtered and evaporated to dryness to give 150 mg of crude compound. The residue was purified by chromatography over silica gel (Stationary phase: irregular SiOH 24 g, Mobile phase:gradient from 0.1% $NH_4OH$, 95% DCM, 5% MeOH to 0.19% $NH_4OH$, 90% DCM, 10% MeOH). The product containing fractions were collected and evaporated to dryness yielding 34 mg (yield 21%) of product which was purified via reverse phase (stationary phase: YMC-actus Triart-C18 10 μm 30*150 mm, mobile phase: gradient from 75% $NH_4CO_3$ (0.2%), 25% ACN to 35% $NH_4HCO_3$ (0.2%), 65% ACN). The fractions containing product were collected and evaporated to dryness to give 25 mg (yield 16%) of compound which was freeze-dried with ACN/water yielding 17 mg (yield 11%) of compound 27.

The compound in the Table below was prepared using an analogous method as described for the preparation of compound above, starting from the respective starting material

| COMPOUND NUMBER | STRUCTURE |
|---|---|
| Compound 50 (from intermediate 32) | 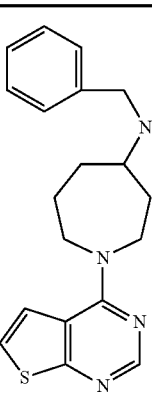 |

Example B14

Preparation of Compound 28

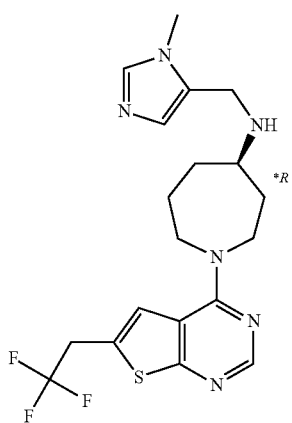 [SMILES: Cn1cncc1CN[C@@H]1CCCN(c2ncnc3sc(CC(F)(F)F)cc23)CC1]

1-Methyl-1-imidazole-5-carboxaldehyde (CAS [39021-62-0]), (100 mg, 0.91 mmol) was added at 10° C., under $N_2$ flow to a solution of intermediate 15 (150 mg, 0.45 mmol) in MeOH (6 mL). The mixture was stirred at rt for 5 h. Then $NaBH_4$ (26 mg, 0.68 mmol) was added and the mixture was stirred at rt for 15 h. The mixture was poured into ice water, extracted with DCM. The organic layer was dried over $MgSO_4$, filtered and evaporated to dryness giving 350 mg of crude compound. The residue was purified by chromatography over silica gel (Stationary phase: irregular SiOH 15-40 m 40 g, Mobile phase: Gradient 0.5% $NH_4OH$, 93% DCM, 7% MeOH). The fractions containing product were collected and evaporated to dryness yielding 113 mg (yield 59%) of compound which was freeze-dried with ACN and water yielding 66 mg of compound 28

The compounds in the Table below were prepared using an analogous method as described for the preparation of compound above, starting from the respective starting materials

| COMPOUND NUMBER | STRUCTURE | YIELD |
|---|---|---|
| Compound 29 (from intermediate 15) | 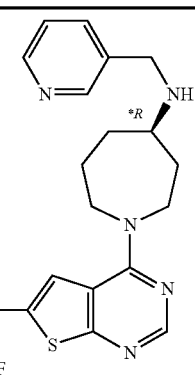 as an HCl salt | |
| Compound 30 (from intermediate 15 | 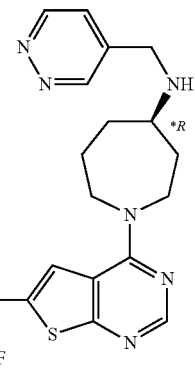 | 25% |

Example B15

Preparation of Compound 31

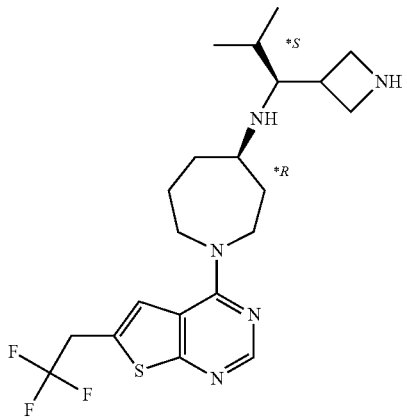 [SMILES: CC(C)[C@H](N[C@@H]1CCCN(c2ncnc3sc(CC(F)(F)F)cc23)CC1)C1CNC1]

HCl (0.4 mL, 1.6 mmol, a 4M solution in dioxane) was added dropwise, at 5° C., to a solution of intermediate 21A (84 mg, 0.16 mmol) in MeOH (4 mL), and the mixture was stirred at rt for 24 h. The reaction mixture was evaporated to dryness, cooled by an iced-water bath, the residue was taken-up with $Et_2O$, a precipitate was filtered off and dried under vacuum overnight to give a solid compound (67 mg)

of compound 31 as an HCl salt m.p.=184° C. (Kofler), (optical rotation: +13.97° (589 nm, DMF, 20° C., c===3.15 mg/mL)).

$^1$H NMR (500 MHz, DMSO-d$_6$) δ ppm 8.44 (s, 1H) 8.23-8.36 (m, 1H) 7.68 (s, 1H) 4.12-4.27 (m, 5H) 3.91 (br d, J=7.3 Hz, 4H) 3.58-3.70 (m, 2H) 3.39-3.46 (m, 1H) 3.22 (br s, 1H) 2.43 (br s, 1H) 2.20 (br d, J=12.3 Hz, 1H) 1.83-2.13 (m, 4H) 1.60 (q, J=11.2 Hz, 1H) 0.93 (d, J=6.6 Hz, 3H) 0.88 (d, J=7.3 Hz, 3H)

The compounds in the Table below were prepared using an analogous method as described for the preparation of compound above, starting from the respective starting materials

| COMPOUND NUMBER | STRUCTURE |
|---|---|
| Compound 32 (from intermediate 21B) | 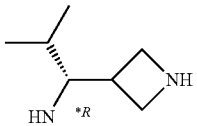<br>as an HCl salt |
| Compound 33 (from intermediate 21) | 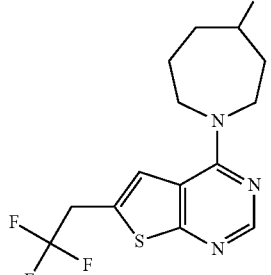<br>as an HCl salt |
| Compound 34 (from intermediate 22) | 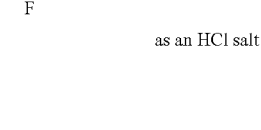<br>as an HCl salt |
| Compound 35 (from intermediate 22A) | 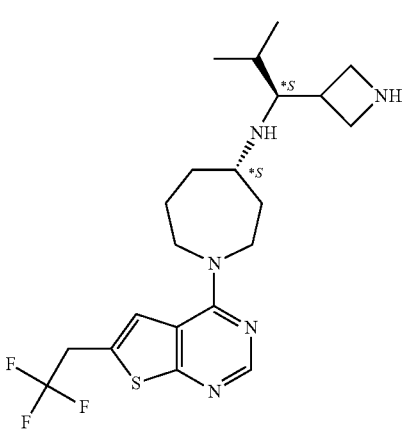<br>as an HCl salt |
| Compound 36 (from intermediate 22B) | 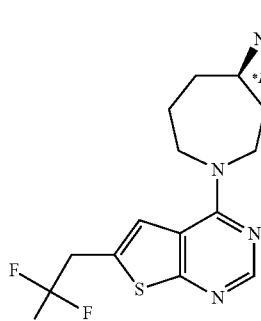<br>as an HCl salt |

Example B18

Preparation of Compound 39

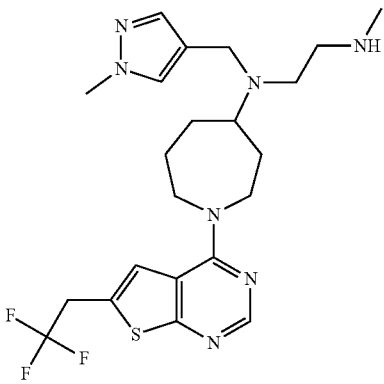 [SMILES: CNCCN(Cc1cnn(C)c1)C1CCCN(c2ncnc3sc(CC(F)(F)F)cc23)CC1]

as an HCl salt

TFA (1.05 mL; 13.75 mmol) was added dropwise, at 5° C., to a solution of intermediate 28 (200 mg; 0.34 mmol) in DCM (12 mL), and the mixture was stirred at rt for 48 hours. The mixture was then evaporated to dryness then the residue was taken up with DCM and $H_2O$ basified with NaOH 3N. The organic layer was extracted (×3 times), dried over $MgSO_4$ and evaporated to dryness. The residue was purified by chromatography over silica gel (Stationary phase: irregular bare silica 40 g, Mobile phase: 1% $NH_4OH$, 90% DCM, 10%0 MeOH). The fractions containing product were collected and evaporated to dryness yielding 110 mg (66%). This fraction was dissolved in ACN (2 mL) and converted with HCl (4M in dioxane) in an HCl salt (75 mg).

Example B20

Preparation of Compound 44

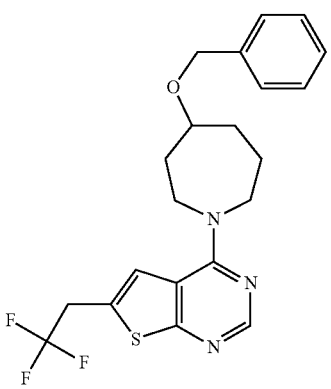 [SMILES: FC(F)(F)Cc1cc2c(N3CCCC(OCc4ccccc4)CC3)ncnc2s1]

A mixture of 4-chloro-6-(2,2,2-trifluoroethyl)thieno[2,3-d]pyrimidine prepared as described in Journal of Medicinal Chemistry (2016), 59(3), 892-913 (CAS[1628317-85-0]) (0.248 g; 0.98 mmol), intermediate 45 (4-benzyloxyazepane HCl salt) (0.285 g), TEA (0.51 ml; 2.95 mmol) in iPrOH (8 mL) were heated at 90° C. for 1 h 30. The solution was cooled to rt, concentrated and the residue was taken-up with DCM, the organic layer was washed with water, dried over $MgSO_4$, filtered and evaporated to dryness. The residue was purified by chromatography over silica gel (40 g, 15-40 pam, eluent: DCM/MeOH: 100/0 to 90/10). The fractions containing product were collected. evaporated to dryness. The residue was freeze-dried with acetonitrile/water 20/80 yielding: 0.308 g of compound 44 (74%).

Example B23

Preparation of Compound 49

Compound 49 in the Table below was prepared using an analogous method as described for the preparation of INTERMEDIATE 12A and 12B, starting from the respective starting materials

| COMPOUND NUMBER | STRUCTURE |
|---|---|
| Compound 49 (from intermediate 35 and methylamine hydrochloride, CAS [593-51-1]) | 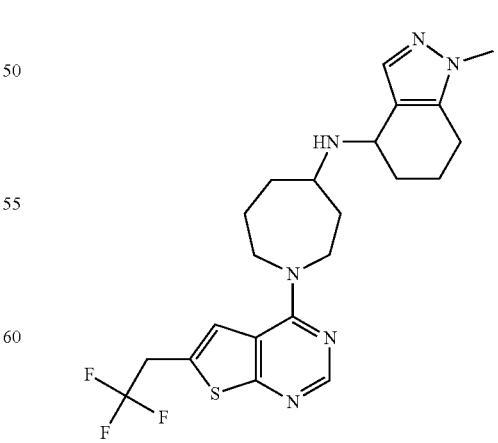 |

Example B24

Preparation of Compound 65

Under $N_2$ flow, at rt, titanium (IV) ethoxide (CAS[3087-36-3]), (0.52 mL; 2.52 mmol) was added to a solution of intermediate-3 (410 mg, 1.25 mmol), and 1-methyl 4,5,6,7 tetrahydroindazole-4amine (CAS[927803-64-3]), (205 mg, 1.36 mmol) in MeOH (8 mL). The solution was stirred at rt for 1 h. Then NaBH(OAc)$_3$, (804 mg, 3.79 mmol) was added and the mixture was stirred at rt for 2 days. The solution was poured out into cooled water, basified with K$_2$CO$_3$ powder, DCM was added and the mixture was filtered through a pad of Celite®. The product was extracted with DCM. The organic layer was combined, washed with brine, dried over MgSO$_4$, filtered and evaporated to dryness. The residue was purified by chromatography over silica gel (Stationary phase: irregular SiOH 15-40 µm 40 g Mobile phase: Gradient from 100% DCM, 0% MeOH to 0.2% NH$_4$OH, 95% DCM, 5% MeOH). The fractions containing the product were collected and evaporated to dryness giving 417 mg (yield 72%) of Compound 65.

The compounds in the Table below were prepared using an analogous method as described above, starting from the respective starting materials.

| COMPOUND NUMBER | STRUCTURE | YIELD |
| --- | --- | --- |
| Compound 66 (from intermediate 3 and 2H-Indazol-4-amine, 4,5,6,7-tetrahydro-2-methyl-, hydrochloride (CAS[1803561-52-5])) | 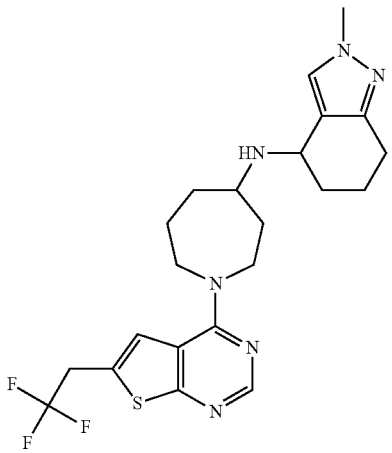 [SMILES: Cn1cc2c(n1)CCCC2NC1CCCN(c2ncnc3sc(CC(F)(F)F)cc23)CC1] | 78% |
| Compound 67 (from intermediate 42 and Benzylamine(CAS[100-46-9]) | 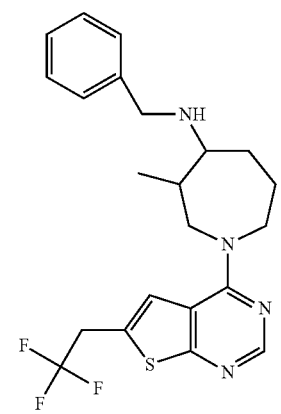 [SMILES: CC1CN(c2ncnc3sc(CC(F)(F)F)cc23)CCCC1NCc1ccccc1] | 69% as a crude product |
| Compound 68 (from intermediate 43 and Benzylamine(CAS[100-46-9]) | 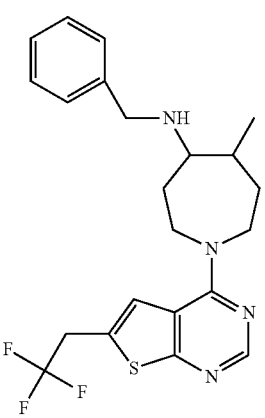 [SMILES: CC1CCN(c2ncnc3sc(CC(F)(F)F)cc23)CCC1NCc1ccccc1] | 110% as a crude product |

Example B25

Preparation of Compound 65a, 65B, 65C and 65D

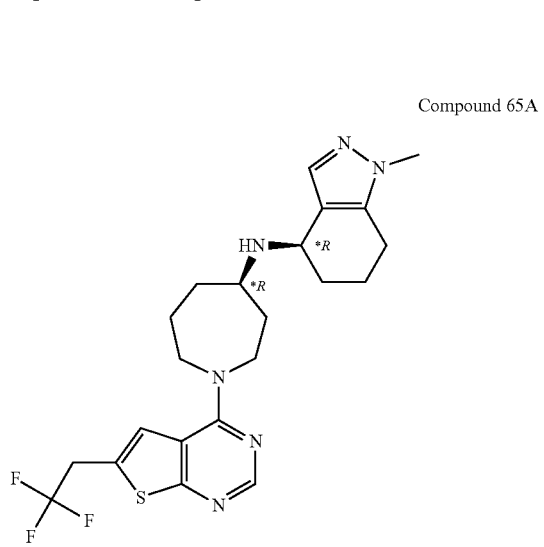

Compound 65A

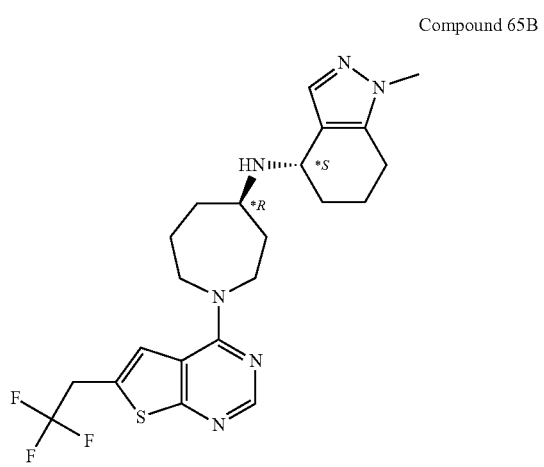

Compound 65B

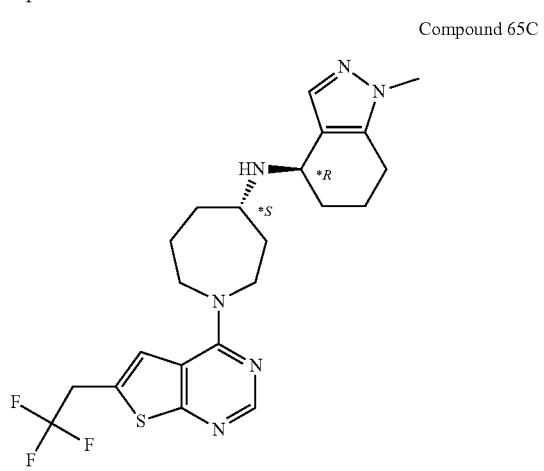

Compound 65C

Compound 65D

Compound 65 (417 mg; 0.9 mmol) was separated using chiral SFC (Stationary phase: Chiralpak AD-H 5 μm 250*30 mm, Mobile phase: 65% $CO_2$, 35% EtOH (0.3% $iPrNH_2$)). The fractions containing the products were collected and evaporated to dryness yielding 81 mg (yield 14%) of first eluted diastereomer A. This fraction was freeze-dried from ACN/water, yielding 79 mg of compound 65A as a white powder (optical rotation=−20° (589 nm, c=2.60 mg/mL, DMF, 20° C.)) and yielding 67 mg (yield 12%) of second eluted diastereomer B. This fraction was freeze-dried from ACN/water, yielding 60 mg of compound 65B as a white powder (optical rotation=−21.72° (589 nm, c=2.44 mg/mL, DMF, 20° C.)) and yielding 84 mg (yield 15%) of third eluted diastereomer C. This fraction was freeze-dried from ACN/water, yielding 83 mg of compound 65C as a white powder (optical rotation=+10.74° (589 nm, c=2.42 mg/mL, DMF, 20° C.)) and yielding 50 mg (yield 9%) of fourth eluted diastereomer D. This fraction was freeze-dried from ACN/water, yielding 44 mg of compound 65D as a white powder (optical rotation=+11.34° (589 nm, c=2.38 mg/mL, DMF, 20° C.)).

The compounds in the Table below were prepared using an analogous method as described for the preparation of compound above, starting from the respective starting materials

| COMPOUND NUMBER | STRUCTURE |
|---|---|
| Compound 66A, Compound 66B, Compound 66C and Compound 66D from SFC separation of Compound 66 (Stationary phase: CHIRALPAK AD-H 5 μm 250*30 mm, Mobile phase: 65% $CO_2$, 35% EtOH(0.3% $iPrNH_2$)) | Compound 66A |

117
-continued

| COMPOUND NUMBER | STRUCTURE |
|---|---|

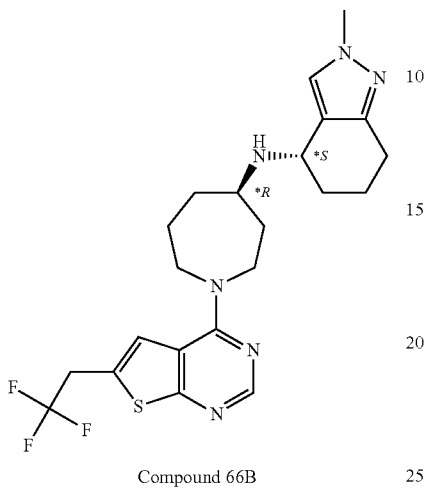
Compound 66B

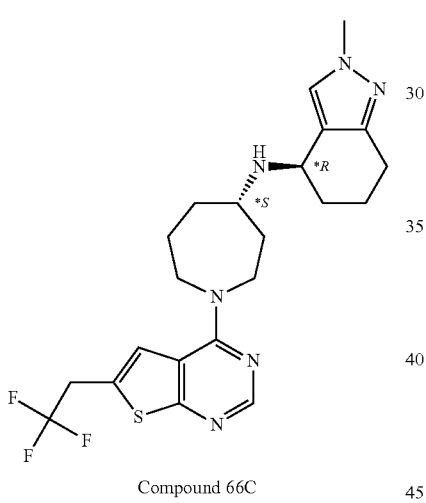
Compound 66C

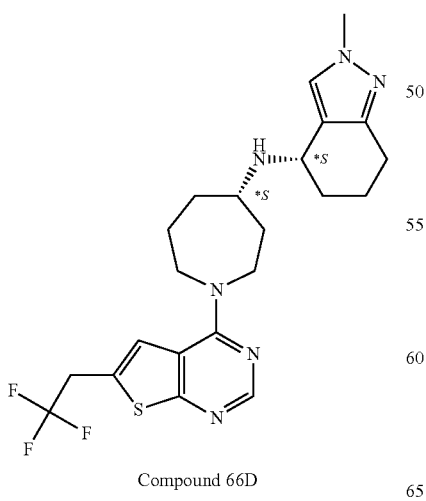
Compound 66D

118

Example B26

Preparation of Compound 68A, 68B and 68C

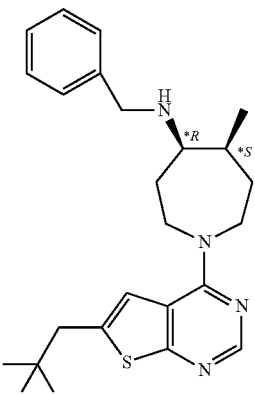
Compound 68A

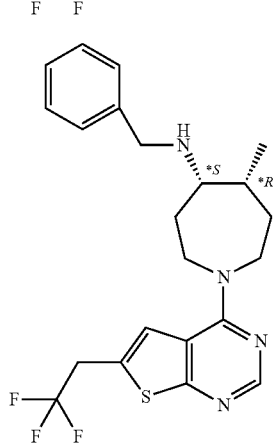
Compound 68B

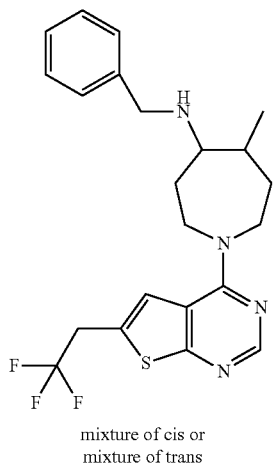
Compound 68C mixture of cis or
mixture of trans

The compound 68 (214 mg) was purified by chromatography over silica gel (Stationary phase: irregular SiOH 15-40 μm 40 g Mobile phase: 0.2% NH$_4$OH, 98% DCM, 2% MeOH). The fractions containing the first eluted compound were collected and evaporated to dryness giving 92 mg (yield 47%) of the first mixture of diastereoisomers A and B and the fractions containing the second eluted compound were collected and evaporated to dryness giving 35 mg of the second mixture of diastereoisomers C. The first mixture of diastereoisomers A and B (92 mg) were separated using chiral SFC (Stationary phase: Lux Cellulose-2 5 μm 250*21.2 mm, Mobile phase: 60% CO$_2$, 40% EtOH (0.3% iPrNH$_2$)). The fractions containing the first eluted diastereoisomer A were collected and evaporated to dryness yielding 41 mg of compound (yield 14%) which was dissolved in 2 mL of ACN, 3 eq of HCl 4N in dioxane (71 μL; 0.28 mmol) were added dropwise at 10° C., Et$_2$O was added and after 30 mn, the solution was evaporated to dryness, Et$_2$O was added and a precipitate was filtered and dried giving 20 mg of compound 68A (MP=136° C./kofler). The fractions containing the second eluted diastereoisomer B were collected and evaporated to dryness yielding 42 mg (yield 22%) which were dissolved in 2 mL of ACN, 3 eq of HCl 4N in dioxane (210 μL; 0.84 mmol) were added dropwise at 10° C., Et$_2$O was added and after 30 mn, the solution was evaporated to dryness, Et$_2$O was added and a precipitate was filtered and dried giving 18 mg of compound 68B (MP=150° C./kofler). The second mixture of diastereoisomers C which wa s obtained during the first purification over silica gel was purified using SFC (Stationary phase: NH$_2$ 5 μm 150*30 mm, Mobile phase: 90% CO$_2$, 10% MeOH (0.3% iPrNH$_2$)). The fractions containing the diastereoisomers C were collected and evaporated to dryness yielding 14 mg (yield 7%) of compound 68C (mixture of cis or mixture of trans).

Example B27

PREPARATION OF COMPOUND 54A, 54B, 54C AND 54D

Compound 54A

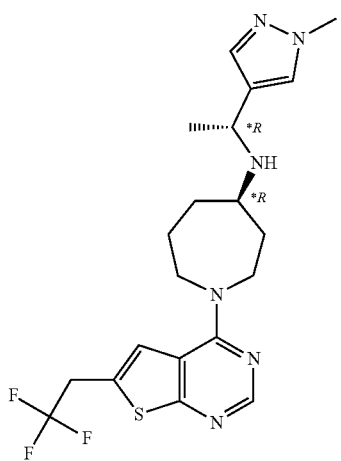

Compound 54B

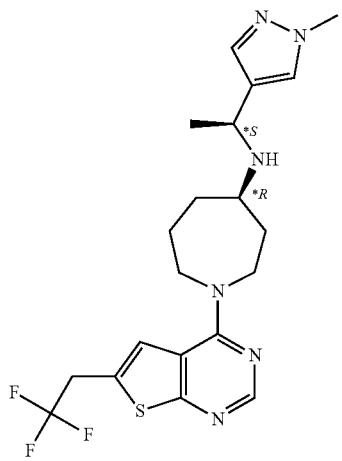

Compound 54C

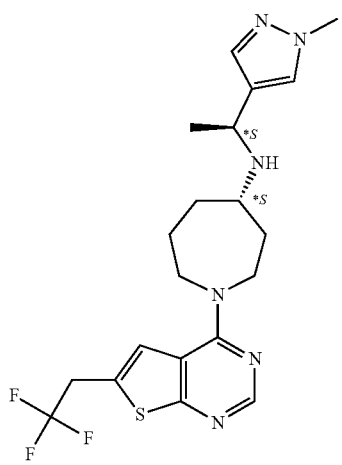

Compound 54D

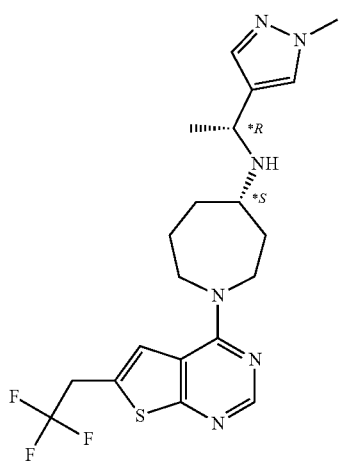

The compound 54 (570 mg) was purified using chiral SFC (Stationary phase: CHIRALPAK AD-H 5 μm 250*30 mm, Mobile phase: 80% CO$_2$, 20% EtOH (0.3% iPrNH$_2$)) yielding 237 mg of a first eluted mixture of diastereoisomers A and B112 mg of a second eluted diastereoisomer C and 93 mg of a third eluted diastereoisomer D. A second separation was made on the mixture of diastereoisomers A and B using CHIRALPAK IC 5 μm 250*21.2 mm, mobile phase: 60% CO$_2$, 40% EtOH (0.3% iPrNH$_2$)) yielding 116 mg of a first eluted diastereoisomer A and 100 mg of a second eluted diastereoisomer B. The diastereoisomer A was dissolved in 5 mL of MeOH, 2 eq of HCl 4N in dioxane (133 µL; 0.53 mmol) were added dropwise at 10° C., Et$_2$O was added and after 30 mn, the solution was evaporated to dryness, Et$_2$O was added and a precipitate was filtered and dried giving 116 mg of compound 54A as an HCl salt (MP=160° C./kofler).

The diastereoisomer B was dissolved in 5 mL of MeOH, 2 eq of HCl 4N in dioxane (114 µL; 0.46 mmol) were added dropwise at 10° C., Et$_2$O was added and after 30 mn, the solution was evaporated to dryness, Et$_2$O was added and a precipitate was filtered and dried giving 104 mg of compound 54B as an HCl salt (MP=160° C./kofler).

The diastereoisomer C was dissolved in 5 mL of MeOH, 2 eq of HCl 4N in dioxane (128 µL; 0.51 mmol) were added dropwise at 10° C., Et$_2$O was added and after 30 mn, the solution was evaporated to dryness, Et$_2$O was added and a precipitate was filtered and dried giving 123 mg (yield 17%) of compound 54C as an HCl salt (MP=160° C./kofler).

The diastereoisomer D was dissolved in 5 mL of MeOH, 2 eq of HCl 4N in dioxane (106 µL; 0.42 mmol) were added dropwise at 10° C., Et$_2$O was added and after 30 mn, the solution was evaporated to dryness, Et$_2$O was added and a precipitate was filtered and dried giving 95 mg (yield 13%) of compound 54D as an HCl salt (MP=160° C./kofler).

Analytical Part

NMR

NMR experiments were carried out using a Bruker Avance 500 spectrometer equipped with a Bruker 5 mm BBFO probe head with z gradients and operating at 500 MHz for the proton and 125 MHz for carbon, or using a Bruker Avance DRX 400 spectrometer using internal deuterium lock and equipped with reverse double-resonance ($^1$H, $^{13}$C, SEI) probe head with z gradients and operating at 400 MHz for the proton and 100 MHz for carbon. Chemical shifts (δ) are reported in parts per million (ppm). J values are expressed in Hz.

LCMS (Liquid Chromatography/Mass Spectrometr)

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times (R$_t$) and ions. If not specified differently in the table of data, the reported molecular ion corresponds to the [M+H]$^+$ (protonated molecule) and/or [M–H]$^-$ (deprotonated molecule). In case the compound was not directly ionizable the type of adduct is specified (i.e. [M+NH$_4$]+, [M+HCOO]$^-$, etc. . . . ). For molecules with multiple isotopic patterns (Br, Cl . . . ), the reported value is the one obtained for the lowest isotope mass. All results were obtained with experimental uncertainties that are commonly associated with the method used. Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE 1a

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| 1 | Waters: Acquity UPLC ® - DAD and Quattro Micro ™ | Waters: BEH C18 (1.7 µm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min, held for 1.94 min, back to 84.2% A in 0.73 min, held for 0.73 min. | 0.343 40 | 6.2 |
| 2 | Waters: Acquity ® H-Class - DAD and SQD2 ™ | Waters: BEH C18 (1.7 µm, 2.1 × 100 mm) | A: 95% CH$_3$COONH$_4$ 7 mM/5% CH$_3$CN, B: CH$_3$CN | 84.2% A to 10.5% A in 2.18 min, held for 1.96 min, back to 84.2% A in 0.73 min, held for 0.73 min. | 0.343 40 | 6.1 |
| 3 | Waters: Acquity UPLC ® H-Class - DAD and QDa | BEH ®-C18 (1.7 µm, 2.1 × 100 mm) | A: 95% CH$_3$COONH$_4$ 7 mM/5% CH$_3$CN, B: CH$_3$CN | 95% A to 5% A in 1 min, held for 1.6 min, back to 95% A in 0.2 min, held for 0.5 min. | 0.5 40 | 3.3 |
| 4 | Waters: Acquity UPLC ® H-Class - DAD and SQD 2 | Waters BEH ®C18 (1.7 µm, 2.1 × 50 mm) | A: 95% CH$_3$COONH$_4$ 7 mM/5% CH$_3$CN, B: CH$_3$CN | From 95% A to 5% A in 1 min, held for 1.6 min, back to 95% A in 0.2 min, held for 0.5 min. | 0.5 40 | 3.3 |
| 5 | Agilent: 1200 - DAD and MSD6110 | Phenomenex: Luna-C18 (5 µm, 2 × 50 mm) | A: CF$_3$COOH 0.1% in water, B: CF$_3$COOH 0.05% in CH$_3$CN | 100% A for 1 min, to 40% A in 4 min, to 15% A in 2.5 min, back to 100% A in 2 min. | 0.8 50 | 10 |

TABLE 1a-continued

| | LCMS Method codes (Flow expressed in mL/min; column temperature (T) in ° C.; Run time in minutes). | | | | | |
|---|---|---|---|---|---|---|
| Method code | Instrument | Column | Mobile phase | gradient | Flow Column T | Run time |
| 6 | Agilent: 1200 - DAD and MSD6110 | Phenomenex: Luna-C18 (5 µm, 2 × 50 mm) | A: $CF_3COOH$ 0.1% in water, B: $CF_3COOH$ 0.05% in $CH_3CN$ | 90% A for 0.8 min, to 20% A in 3.7 min, held for 3 min, back to 90% A in 2 min. | 0.8 50 | 10 |

Melting Points

For a number of compounds, melting points (MP) were determined with a DSC1 (Mettler-Toledo). Melting points were measured with a temperature gradient of 10° C./minute. Maximum temperature was 300° C. Values are peak values.

For a number of compounds, melting points were obtained with a Kofler hot bench (indicated with (K)), consisting of a heated plate with linear temperature gradient, a sliding pointer and a temperature scale in degrees Celsius.

TABLE 1b

LCMS and melting point data. Co. No. means compound number; $R_t$ means retention time in min.

| Co. No. | mp (° C.) | Rt (min) | UV Area % | [M + H]+ | Adduct | LCMS Method |
|---|---|---|---|---|---|---|
| I-13 | | 1.46 | 88% | 459.5 | | 3 |
| 3A | | 1.2 | | 421.3 | | 3 |
| 3* | 134° C. (K) | 2.75 | 100 | 421.1 | 479.3 [M + $CH_3COO$]− | 1 |
| 4* | 230° C. (K) | 2.74 | 100 | 421.1 | 479.3 [M + $CH_3COO$]− | 1 |
| I-1 | | 1.24 | 93.84 | 374.4 | | 3 |
| I-2 | | 2.4 | 97.56 | 332 | 330 | 1 |
| I-3 | | 1.12 | 100 | 330.1 | 328.1 | 3 |
| 5* | 244° C. (K) | 2.67 | 100 | 395.4 | 453.3 [M + $CH_3COO$]− | 2 |
| 5a | | 2.67 | 97.56 | 395.4 | 453.3 [M + $CH_3COO$]− | 2 |
| B1A | | 2.35 | 100 | 387.1 | 445.3 [M + $CH_3COO$]− | 1 |
| B1B | | 2.35 | 100 | 387.1 | 445.4 [M + $CH_3COO$]− | 1 |
| I 10* | | 1.8 | 100 | 331.4 | 389.3 [M + $CH_3COO$]− | 2 |
| I 11* | | 1.86 | 100 | 331.4 | 389.4 [M + $CH_3COO$]− | 2 |
| 10B* | | 2.32 | 100 | 454.4 | 512.3 [M + $CH_3COO$]− | 2 |
| 6 | 111.41° C./−27.83 J/g[a] | 3.3 | 96.53 | 433.2 | 491.4 [M + $CH_3COO$]− | 1 |
| 7A* | 176° C. (K) | 3.11 | 98.39 | 457.1 | 515.3 [M + CH3COO−]; 455.2 [M + H−] | 1 |
| 7B* | 180° C. (K) | 3.1 | 100 | 457.1 | 515.3 [M + CH3COO−]; 455.1 [M + H−] | 1 |
| 9A* | 156° C. (K) | 3.15 | 97.46 | 449.1 | 507.3 [M + CH3COO−]; 447.1 [M + H−] | 1 |
| 9B* | 160° C. (K) | 3.15 | 100 | 449.1 | 507.4 [M + CH3COO−]; 447.6 [M + H−] | 1 |

TABLE 1b-continued

LCMS and melting point data. Co. No. means compound number; R$_t$ means retention time in min.

| Co. No. | mp (° C.) | Rt (min) | UV Area % | [M + H]$^+$ | Adduct | LCMS Method |
|---|---|---|---|---|---|---|
| 14 | | 3.48 | 100 | 408.1 | 406.1 | 1 |
| I-8 | | 1.39 | 98.28 | 431.4 | 489.3 [M + CH$_3$COO]$^-$ | 4 |
| I-12A | | 1.31 | 100 | 554.6 | 612.4 [M + CH$_3$COO]$^-$ | 3 |
| 10A* | 220° C. (K) | 2.43 | 100 | 454.2 | 512.5 [M + CH$_3$COO]$^-$ | 1 |
| 10B* | 205° C. (K) | 2.32 | 100 | 454.4 | 512.3 [M + CH$_3$COO]$^-$ | 4 |
| 11 | | 2.13 | 97.17 | 425.1 | 483.4 [M + CH$_3$COO]$^-$ | 1 |
| 11B* | | 2.1 | 96.63 | 425.1 | 483.4 [M + CH$_3$COO]$^-$ | 1 |
| 11A | | 2.1 | 98.27 | 425.1 | 483.4 [M + CH$_3$COO]$^-$ | 1 |
| 14A | | 2.37 | 98.19 | 417.1 | 475.4 [M + CH$_3$COO]$^-$ | 1 |
| 14B | | 2.38 | 98.13% | 417.1 | 475.3 [M + CH$_3$COO]$^-$ | 1 |
| 12 | 94° C. (K) | 2.04 | 99.36 | 373.4 | 431.2 [M + CH$_3$COO]$^-$ | 2 |
| 15 | 110° C. (K) | 3.48 | 100 | 408.1 | | 1 |
| 16* | | 3.04 | 99.85 | 435 | | 6 |
| 17* | | 3.18 | 99.05 | 464 | | 5 |
| 18* | | 3.01 | 99.96 | 465 | | 6 |
| 19* | | 2.83 | 99.84 | 435 | | 6 |
| 21* | | 3.72 | 99.01 | 451 | | 5 |
| 22* | | 2.93 | 99.19 | 451 | | 6 |
| 23* | | 3.00 | 99.85 | 435 | | 6 |
| 24* | | 3.56 | 99.93 | 385 | | 5 |
| 26* | 156° C. (K) | 2.07 | 100 | 411 | 469.3 [M + CH3COO-] | 1 |
| 27 | | 2.02 | 97.57 | 455.2 | 513.4 [M + CH3COO-] | 1 |
| 28 | | 2.28 | 98.25 | 425.1 | 483.3 [M + Ch3COO-] | 1 |
| 29* | | 2.39 | 95.58 | 422.1 | 480.2 [M + CH3COO-] | 1 |
| 30 | | 2.32 | 96.07 | 423.1 | 481.3 [M + CH3COO-] | 1 |
| 31* | 184° C. (K) | 2.53 | 100 | 442.2 | 500.4 [M + CH3COO]- | 1 |
| 32* | 190° C. (K) | 2.51 | 100 | 442.2 | 500.4 [M + CH3COO]- | 1 |
| 33* | 200° C. (K) | 2.52 | 95.36 | 442.1 | 500.2 [M + CH3COO]- | 1 |
| 34* | 188° C. (K) | 2.53 | 100 | 442.1 | 500.2 [M + CH3COO]- | 1 |
| 35* | 193° C. (K) | 2.53 | 100 | 442.2 | 500.4 [M + CH3COO]- | 1 |
| 36* | 208° C. (K) | 2.51 | 100 | 442.1 | 500.4 [M + CH3COO]- | 1 |
| 39* | | 2.26 | 100 | 482.2 | 540.5 [M + CH3COO-] | 1 |
| Int. 42 | 92° C. (K) | 2.8 | 96.61 | 344 | 402.1 [M + CH3COO]- | 1 |
| 44 | | 3.54 | 100 | 100 | | 1 |
| 49 | | 2.33 | 72.15 | 478.2 | 536.6 [M + CH3COO]- | 1 |
| 50 | | 3.13 | 95.25 | 465.2 | 523.4 [M + CH3COO]- | 1 |
| 52 | | 2.67, 2.69 | 42.17, 56.50 | 444.2 | 502.4 [M + CH3COO]- | 1 |
| 53 | | 2.86 | 95.8 | 506.2 | 564.5 [M + CH3COO-] | 1 |
| 54A | 160 C. (K) | 2.17 | 98.28 | 439.1 | 497.3 [M + CH3COO]- | 1 |
| 54B | 160° C. (K) | 2.18 | 99.45 | 439.1 | 497.3 [M + CH3COO]- | 1 |
| 54C | 178° C. (K) | 2.17 | 100 | 439.1 | 497.3 [M + CH3COO]- | 1 |
| 54D | 160° C. (K) | 2.17 | 100 | 439.1 | 497.3 [M + CH3COO]- | 1 |

TABLE 1b-continued

LCMS and melting point data. Co. No. means compound number; $R_t$ means retention time in min.

| Co. No. | mp (° C.) | Rt (min) | UV Area % | [M + H]⁺ | Adduct | LCMS Method |
|---|---|---|---|---|---|---|
| 55* | 110° C. (K) |  | 100 | 429.1 | 487.3 | 1 |
| 57A* | 150° C. (K) | 2.73 | 1.05 | 492.3 | 550.4 [M + CH3COO]− | 1 |
| 57B* |  | 2.8 | 95.73 | 495.3 | 550.4 [M + CH3COO−] | 1 |
| 58A* |  | 3.24 | 100 | 481.2 | 539.4 [M + CH3COO−] | 1 |
| 58B* |  | 3.24 | 98.24 | 481.2 | 539.4 [M + CH3COO−] | 1 |
| 58A* |  | 3.24 | 100 | 481.2 | 539.4 [M + CH3COO−] | 1 |
| 58B* |  | 3.24 | 98.24 | 481.2 | 539.4 [M + CH3COO−] | 1 |
| 59A |  | 3.32 | 97.49 | 477.2 | 535.3 [M + CH3COO]− | 1 |
| 59B |  | 3.32 | 98.01 | 477.2 | 535.2 [M + CH3COO]− | 1 |
| 60A* |  | 3.33 | 99.34 | 515.3 | 573.5 [M + CH3COO−] | 1 |
| 60B* |  | 3.33 | 98.73 | 515.3 | 573.5 [M + CH3COO−] | 1 |
| 61* | 110° C. (K) | 2.21 | 99.37 | 524.3 | 582.5 [M + CH3COO−] | 1 |
| 62* | 130° C. (K) | 2.11 | 99.27 | 416.1 | 474.3 [M + CH3COO−] | 1 |
| 63* |  | 2.29 | 100 | 510.3 | 568.5 [M + CH3COO−] | 1 |
| 65A |  | 2.33 | 98.72 | 465.1 | 523.2 [M + CH3COO]− | 1 |
| 65B |  | 2.33 | 99.22 | 465.1 | 523.3 [M + CH3COO]− | 1 |
| 65C |  | 2.32 | 99.27 | 465.2 | 523.4 [M + CH3COO]− | 1 |
| 65D |  | 2.33 | 98.61 | 465.1 | 523.3 [M + CH3COO]− | 1 |
| 66A |  | 2.31 | 97.71 | 465.2 | 523.3 [M + CH3COO]− | 1 |
| 66B |  | 2.31 | 97.51 | 465.2 | 523.4 [M + CH3COO]− | 1 |
| 66C |  | 2.31 | 97.4 | 254.9 | 523.4 [M + CH3COO]− | 1 |
| 66D |  | 2.31 | 97.49 | 465.2 | 523.3 [M + CH3COO]− | 1 |
| 67A | 164° C. (K) | 3.11 | 100 | 435.1 | 493.3 [M + CH3COO]− | 1 |
| 67B | 180° C. (K) | 3.37 | 100 | 435.1 | 493.3 [M + CH3COO]− | 1 |
| 68A* | 134° C. (K) | 3.26 | 99.21 | 435.2 | 493.3 [M + CH3COO]− | 1 |
| 68B* | 150° C. (K) | 3.26 | 99.36 | 435.2 | 493.4 [M + CH3COO]− | 1 |
| 68C |  | 3.34 | 95.32 | 435.2 | 493.4 [M + CH3COO]− | 1 |
| 69 |  | 2.24 | 97.62 | 423.1 | 481.3 [M + CH3COO]− | 2 |
| I 17 |  | 1.22 | 99.06 | 511.1 | 569.3 [M + CH3COO−] |  |
| I 28 |  | 1.32 | 98.42 | 582.3 | 640.3 [M + CH3COO−] | 1 |
| I 34 |  | 0.87 | 87.31 | 430.4 | 488.2 [M + CH3COO−] | 1 |
| I 35* |  | 0.92 | 85.27 | 465.5 |  | 3 |

(a)(25° C. to 300° C./10° C. min/40 μL Al)
*means hydrochloride salt

SFCMS—Methods
General Procedure for SFC-MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE 2a

Analytical SFC-MS Methods (Flow expressed in mL/min; column temperature (T) in ° C.; Run time in minutes, Backpressure (BPR) in bars.

| Method code | column | mobile phase | Gradient | Flow Col T | Run time BPR |
|---|---|---|---|---|---|
| 1 | Phenomenex Luxcellulose-2 column (3 μm, 100 × 4.6 mm) | A: $CO_2$ B: MeOH (+0.3% iPrNH$_2$) | 40% B hold 3 min | 3.5 35 | 3 103 |
| 2 | Daicel Chiralpak ® AD-3 column (3 μm, 100 × 4.6 mm) | A: $CO_2$ B: EtOH | 15% B hold 3 min | 3.5 35 | 3 103 |
| 3 | Daicel Chiralcel ® OJ-3 column (3 μm, 100 × 4.6 mm) | A: $CO_2$ B: EtOH (+0.3% iPrNH$_2$) | 20% B hold 3 min | 3.5 35 | 3 103 |
| 4 | Daicel Chiralcel ® OJ-3 column (3 μm, 100 × 4.6 mm) | A: $CO_2$ B: iPrOH (+0.3% iPrNH$_2$) | 10% B hold 3 min | 3.5 35 | 3 103 |
| 5 | Daicel Chiralpak ® AD-3 column (3 μm, 100 × 4.6 mm) | A: $CO_2$ B: IPrOH | 30% B hold 3 min | 3.5 35 | 3 103 |
| 6 | Phenomenex Lux cellulose 2 (3 μm, 100 × 4.6 mm) | A: $CO_2$ B: EtOH (0.3% iPrNH2) | 40% B hold 3 min, | 3.5 35 | 3 105 |
| 7 | Phenomenex Lux cellulose 2 (3 μm, 100 × 4.6 mm) | A: $CO_2$ B: MeOH (0.3% iPrNH2) | 30% B hold 3 min, | 3.5 35 | 3 105 |
| 8 | Phenomenex Lux cellulose 2 (3 μm, 100 × 4.6 mm) | A: $CO_2$ B: MeOH (0.3% iPrNH2) | 15% B hold 3 min, | 3.5 35 | 3 105 |
| 9 | Daicel Chiralpak ® AD-3 (3 μm, 100 × 4.6 mm) | A: $CO_2$ B: MeOH/iPrOH 50/50(0.3% iPrNH$_2$) | 30% B hold 3 min, | 3.5 35 | 3 105 |
| 10 | Daicel Chiralpak ® AD-3 (3 μm, 100 × 4.6 mm) | B: MeOH(+0.3% iPrNH$_2$) | 20% B hold 3 min, | 3.5 35 | 3 105 |
| 11 | Daicel Chiralpak ® AD-3 (3 μm, 100 × 4.6 mm) | B: MeOH(+0.3% iPrNH$_2$) | 30% B hold 3 min, | 3.5 35 | 4 105 |
| 12 | Daicel Chiralpak ® AD-3 column (3 μm, 100 × 4.6 mm) | A: $CO_2$ B: EtOH | 30% B hold 3 min | 3.5 35 | 6 103 |
| 13 | Daicel Chiralcel ® OJ-3 (3 μm, 100 × 4.6 mm | A: $CO_2$ B: EtOH (0.3% iPrNH2) | 10% B hold 3 min, | 3.5 35 | 6 105 |
| 14 | Daicel Chiralpak ® AD-3 column (3 μm, 100 × 4.6 mm) | A: $CO_2$ B: IPOH | 30% B hold 3 min | 3.5 35 | 3 103 |
| 15 | Daicel Chiralcel ® OD-3 (3 μm, 100 × 4.6 mm) | A: $CO_2$ B: EtOH(+0.3% iPrNH2) | 25% B hold 3 min, | 3.5 35 | 3 105 |
| 16 | Daicel Chiralpak ® AD-3 (3 μm, 100 × 4.6 mm) | A: $CO_2$ B: MeOH/iPrOH 50/50(0.3% iPrNH$_2$) | 20% B hold 3 min, | 3.5 35 | 10 105 |

TABLE 2a-continued

Analytical SFC-MS Methods (Flow expressed in mL/min; column temperature (T) in ° C.; Run time in minutes, Backpressure (BPR) in bars.

| Method code | column | mobile phase | Gradient | Flow Col T | Run time BPR |
|---|---|---|---|---|---|
| 17 | Daicel Chiralpak ® AD-3 column (3 µm, 100 × 4.6 mm) | A: $CO_2$ B: EtOH | 30% B hold 3 min | 3.5 35 | 3 103 |
| 19 | Daicel Chiralpak ® IC-3 (3 µm, 100 × 4.6 mm) | A: $CO_2$ B: EtOH(+0.3% $iPrNH_2$) | 40% B hold 3 min, | 3.5 35 | 3 105 |
| 20 | Daicel Chiralpak ® AD-3 column (3 µm, 100 × 4.6 mm) | A: $CO_2$ B: EtOH | 20% B hold 3 min | 3.5 35 | 6 103 |

TABLE 2b

SFC-MS data (Isomer elution order 'A' before 'B', 'B' before 'C', 'C' before 'D')

| Co. No. | UV % Area | Isomer Elution order | SFCMS Method |
|---|---|---|---|
| I10* | 100 | A | 1 |
| I11* | 100 | B | 1 |
| I-8A | 100 | A | 2 |
| I-8B | 99.56 | B | 2 |
| 3* | 99.72 | A | 3 |
| 4* | 99.68 | B | 3 |
| B1A | 99.63 | A | 4 |
| B1B | 96.23 | B | 4 |
| 13A | 100 | A | 5 |
| 13B | 100 | B | 5 |
| 68A* | 100 | A | 6 |
| 68B* | 100 | B | 6 |
| I20A | 100 | A | 8 |
| I20B | 98.8 | B | 8 |
| 34* | 100 | A and D | 9 |
| 33* | 100 | B and C | 9 |
| 57* | 100 | A | 10 |
| 57B* | 100 | B | 10 |
| 59A | 100 | A | 11 |
| 59B | 100 | B | 11 |
| 65A | 100 | A | 12 |
| 65B | 100 | B | 12 |
| 65C | 100 | C | 12 |
| 65D | 100 | D | 12 |
| I21A | 100 | A | 13 |
| I21B | 100 | B | 13 |
| 58A* | 100 | A | 1 |
| 58B* | 99.73 | B | 1 |
| I 22A | 100 | A | 14 |
| I 22B | 99.04 | B | 14 |
| 60A* | 99.84 | A | 15 |
| 60B* | 98.01 | B | 15 |
| 66A | 100 | A | 16 |
| 66B | 100 | B | 16 |
| 66C | 99.05 | C | 16 |
| 66D | 100 | D | 16 |
| 31* | 100 | A | 17 |
| 32* | 99.60 | B | 17 |
| 35* | 98.64 | A | 17 |
| 36* | 100 | B | 17 |
| 54A | 100 | A | 19 |
| 54B | 99.18 | B | 19 |
| 54C | 100 | C | 20 |
| 54D | 100 | D | 20 |

*means hydrochloride salt

Optical Rotation (OR)

Optical Rotation is measured with a polarimeter 341 Perkin Elmer. The polarized light is passed through a sample with a path length of 1 decimeter and a sample concentration of 0.2 to 0.4 gram per 100 milliliters. 2 to 4 mg of the product in vial are weight, then dissolved with 1 to 1.2 ml of spectroscopy solvent (DMF for example). The cell is filled with the solution and put into the polarimeter at a temperature of 20° C. The OR is read with 0.004° of precision.

Calculation of the concentration: weight in gram×100/volume in ml $[\alpha]_d^{20}$: (read rotation×100)/(1.000 dm×concentration).

$^d$ is sodium D line (589 nanometer) unless another wavelength is specified.

TABLE 3

OR data: solvent: DMF; temperature: 20° C.; 'conc' means concentration (g/100 mL); 'OR' means optical rotation.

| Co. No. | OR (°) | Wavelength (nm) | Conc. |
|---|---|---|---|
| 5* | +3.85 | 546 | 0.286 |
| I10* | +42.01 | 365 | 0.288 |
| I11* | −45.2 | 365 | 0.25 |
| I-8A | +4.78 | 589 | 0.293 |
| I-8B | −4.95 | 589 | 0.364 |
| B1A | −3.73 | 589 | 0.295 |
| B1B | −4.81 | 589 | 0.27 |
| 3* | +59.08 | 365 | 0.303 |
| 4* | −60.56 | 365 | 0.284 |
| 11B | −5.76 | 589 | 0.243 |
| 11A | +4.94 | 589 | 0.324 |
| 13A | +3.19 | 589 | 0.313 |
| 13B | −4.66 | 589 | 0.279 |
| 68A* | +72.79 | 365 | 0.294 |
| 68B* | −68.05 | 365 | 0.266 |
| 57A* | +13.67 | 589 | 0.300 |
| 57B* | −18.21 | 589 | 0.280 |
| 59A | +8.33 | 589 | 0.264 |
| 59B | −14.17 | 589 | 0.247 |
| 34* | −25 | 589 | 0.260 |
| 33* | +18.04 | 589 | 0.388 |
| 65A | −20 | 589 | 0.260 |
| 65B | −21.72 | 589 | 0.244 |
| 65C | +10.74 | 589 | 0.242 |
| 65D | +11.34 | 589 | 0.238 |
| 58A* | +5.81 | 589 | 0.241 |
| 58B* | −6.67 | 589 | 0.285 |
| 60A* | +22.87 | 589 | 0.328 |
| 60B* | −23.36 | 589 | 0.274 |
| 52 | −8.98 | 589 | 0.245 |
| 66A | −10.81 | 589 | 0.259 |
| 66B | −14.16 | 589 | 0.219 |
| 66C | +8.27 | 589 | 0.266 |
| 66D | +4.03 | 589 | 0.248 |
| 31* | +13.97 | 589 | 0.315 |

TABLE 3-continued

OR data: solvent: DMF; temperature: 20° C.; 'conc' means concentration (g/100 mL); 'OR' means optical rotation.

| Co. No. | OR (°) | Wavelength (nm) | Conc. |
|---------|--------|-----------------|-------|
| 32* | +26.85 | 589 | 0.365 |
| 35* | −15.16 | 589 | 0.31 |
| 36* | −26.87 | 589 | 0.335 |
| 54A | −46.38 | 589 | 0.345 |
| 54B | +16.99 | 589 | 0.312 |
| 54C | +49.15 | 589 | 0.352 |
| 54D | −24.35 | 589 | 0.382 |
| 26* | +46.24 | 365 | 0.279 |

*means hydrochloride salt

Pharmacological Part

1) Menin/MLL Fluorescence Polarization Assay

To a non-surface binding, black 384-well microtiter plate was added 50 nL 160× test compound in DMSO and 4 μL 2× menin in assay buffer (40 mM Tris-HCl, pH 7.5, 50 mM NaCl, 1 mM DTT and 0.001% Tween 20). After incubation of test compound and menin for 10 min at ambient temperature, 4 μL 2×FITC-MBM1 peptide (FITC-β-alanine-SARWRFPARPGT-NH$_2$) in assay buffer was added, the microtiter plate centrifuged at 1000 rpm for 1 min and the assay mixtures incubated for 15 min at ambient temperature. The relative amount of menin•FITC-MBM1 complex present in an assay mixture is determined by measuring the fluorescence polarization (FP) of the FITC label with a BMG Pherastar plate reader (ex. 485 nm/em. 520 nm) at ambient temperature. The final concentrations of reagents in the binding assay are 100 nM menin, 5 nM FITC-MBM1 peptide and 0.625% DMSO in assay buffer. Dose-response titrations of test compounds are conducted using an 11 point, three-fold serial dilution scheme, starting at 31 μM.

Compound potencies were determined by first calculating % inhibition at each compound concentration according to equation 1:

$$\% \text{ inhibition} = ((HC-LC)-(FP^{compound}-LC))/(HC-LC))*100 \quad \text{(Eqn 1)}$$

Where LC and HC are the FP values of the assay in the presence or absence of a saturating concentration of a compound that competes with FITC-MBM1 for binding to menin, and $FP^{compound}$ is the measured FP value in the presence of the test compound. HC and LC FP values represent an average of at least 16 replicates per plate. For each test compound, % inhibition values were plotted vs. the logarithm of the test compound concentration, and the IC$_{50}$ value derived from fitting these data to equation 2:

$$\% \text{ inhibition} = \text{Bottom} + (\text{Top} - \text{Bottom})/(1+10\char`\^((\log IC_{50}-\log[cmpd])*h)) \quad \text{(Eqn 2)}$$

Where Bottom and Top are the lower and upper asymptotes of the dose-response curve, respectively, IC$_{50}$ is the concentration of compound that yields 50% inhibition of signal and h is the Hill coefficient.

2) Menin/MLL Homogenous Time-Resolved Fluorescence (HTRF) Assay

To an untreated, white 384-well microtiter plate was added 40 nL 200× test compound in DMSO and 4 μL 2× terbium chelate-labeled menin (vide infra for preparation) in assay buffer (40 mM Tris-HCl, pH 7.5, 50 mM NaCl, 1 mM DTT and 0.05% Pluronic F-127). After incubation of test compound and terbium chelate-labeled menin for 5 min at ambient temperature, 4 μL 2×FITC-MBM1 peptide (FITC-β-alanine-SARWRFPARPGT-NH$_2$) in assay buffer was added, the microtiter plate centrifuged at 1000 rpm for 1 min and the assay mixtures incubated for 15 min at ambient temperature. The relative amount of menin-FITC-MBM1 complex present in an assay mixture is determined by measuring the homogenous time-resolved fluorescence (HTRF) of the terbium/FITC donor/acceptor fluorphore pair using a BMG Pherastar plate reader (ex. 337 nm/terbium em. 490 nm/FITC em. 520 nm) at ambient temperature. The degree of fluorescence resonance energy transfer (the HTRF value) is expressed as the ratio of the fluorescence emission intensities of the FITC and terbium fluorophores ($F^{em}$ 520 nm/$F^{em}$ 490 nm). The final concentrations of reagents in the binding assay are 100 pM terbium chelate-labeled menin, 75 nM FITC-MBM1 peptide and 0.5% DMSO in assay buffer. Dose-response titrations of test compounds are conducted using an 11 point, three-fold serial dilution scheme, starting typically at 25 μM.

Compound potencies were determined by first calculating % inhibition at each compound concentration according to equation 1:

$$\% \text{ inhibition} = ((HC-LC)-(HTRF^{compound}-LC))/(HC-LC))*100 \quad \text{(Eqn 1)}$$

Where LC and HC are the HTRF values of the assay in the presence or absence of a saturating concentration of a compound that competes with FITC-MBM1 for binding to menin, and $HTRF^{compound}$ is the measured HTRF value in the presence of the test compound. HC and LC HTRF values represent an average of at least 16 replicates per plate. For each test compound, % inhibition values were plotted vs. the logarithm of the test compound concentration, and the IC$_{50}$ value derived from fitting these data to equation 2:

$$\% \text{ inhibition} = \text{Bottom} + (\text{Top} - \text{Bottom})/(1+10\char`\^((\log IC_{50}-\log[cmpd])*h)) \quad \text{(Eqn 2)}$$

Where Bottom and Top are the lower and upper asymptotes of the dose-response curve, respectively, IC$_{50}$ is the concentration of compound that yields 50% inhibition of signal and h is the Hill coefficient.

Preparation of Terbium cryptate labeling of Menin: Menin (a.a. 1-610-6×his tag) was labeled with terbium cryptate as follows. 2 mg of Menin was buffer exchanged into 1× phosphate buffered saline. 16 uM Menin was incubated with 4-fold molar excess NHS-terbium cryptate (Cisbio Bioassays, Bedford, Mass.) for 2 hours at room temperature. The labeled protein was purified away from free label by running the reaction over a Superdex 200 Increase 10/300 GL column at 0.75 ml/min. Peak fractions were collected, aliquoted and frozen at −80° C.

MENIN Protein Sequence (SEQ ID NO: 1):

MGLKAAQKTLFPLRSIDDVVRLFAAELGREEPDLVLLSLVLGFVEHF

LAVNRVIPTNVPELTFQPSPAPDPPGGLTYFPVADLSIIAALYARFT

AQIRGAVDLSLYPREGGVSSRELVKKVSDVIWNSLSRSYFKDRAHIQ

SLFSFITGTKLDSSGVAFAVVGACQALGLRDVHLALSEDHAWVVFGP

NGEQTAEVTWHGKGNEDRRGQTVNAGVAERSWLYLKGSYMRCDRKME

VAFMVCAINPSIDLHTDSLELLQLQQKLLWLLYDLGHLERYPMALGN

LADLEELEPTPGRPDPLTLYHKGIASAKTYYRDEHIYPYMYLAGYHC

RNRNVREALQAWADTATVIQDYNYCREDEEIYKEFFEVANDVIPNLL

KEAASLLEAGEERPGEQSQGTQSQGSALQDPECFAHLLRFYDGICKW

-continued

EEGSPTPVLHVGWATFLVQSLGRFEGQVRQKVRIVSREAEAAEAEEP

WGEEAREGRRRGPRRESKPEEPPPPKKPALDKGLGTGQGAVSGPPRK

PPGTVAGTARGPEGGSTAQVPAPAASPPPEGPVLTFQSEKMKGMKEL

LVATKINSSAIKLQLTAQSQVQMKKQKVSTPSDYTLSFLKRQRKGLH

HHHHH

3) Proliferation Assay

The anti-proliferative effect of menin/MLL protein/protein interaction inhibitor test compounds was assessed in human leukemia cell lines. The cell lines MV-4-11 and MOLM14 harbor MLL translocations and express the MLL fusion proteins MLL-AF4 and MLL-AF9, respectively, as well as the wildtype protein from the second allele. Therefore, the MLL rearranged cell lines MV-4-11 and MOLM14 exhibit stem cell-like HOXA/MEIS1 gene expression signatures. K562 was used as a control cell line containing two MLL wildtype alleles in order to exclude compounds that display general cytotoxic effects.

MV-4-11 and MOLM14 were cultured in RPMI-1640 (Sigma Aldrich) supplemented with 10% fetal bovine serum (HyClone), 2 mM L-glutamine (Sigma Aldrich) and 50 µg/ml gentamycin (Gibco). K562 were propagated in RPMI-1640 (Sigma Aldrich) supplemented with 20% fetal bovine serum (HyClone), 2 mM L-glutamine (Sigma Aldrich) and 50 µg/ml gentamycin (Gibco). Cells were kept at 0.3-2.5 million cells per ml during culturing and passage numbers did not exceed 25.

In order to assess the anti-proliferative effects, 1,500 MV-4-11, 300 MOLM14 or 750 K562 cells were seeded in 200 µl media per well in 96-well round bottom, ultra-low attachment plates (Costar, catalogue number 7007). Cell seeding numbers were chosen based on growth curves to ensure linear growth throughout the experiment. Test compounds were added at different concentrations and the DMSO content was normalized to 0.3%. Cells were incubated for 8 d at 37° C. and 5% $CO_2$. Spheroid like growth was monitored in real-time by live-cell imaging (IncuCyt-eZOOM, Essenbio, 4× objective) acquiring one image every four hours for 8 d. Confluence (%) as a measure of spheroid size was determined using an integrated analysis tool.

In order to determine the cumulative effect of the test compounds over time, the area under the curve (AUC) in a plot of confluence against time was calculated. Confluence at the beginning of the experiment (t=0) was used as baseline for the AUC calculation.

Absolute $IC_{50}$ values were calculated according to the following procedure:

% Control=(AUC sample/AUC control)*100

AUC control=mean AUC of control values (cells without compound/DMSO as vehicle control)

A non-linear curve fit was applied using the least squares (ordinary) fit method to the plot of % control versus compound concentration. Based on this, the absolute $IC_{50}$ value (half maximal inhibitory concentration of the test compound causing an anti-proliferative effect of 50% relative to the vehicle control) was calculated.

TABLE 4

Biological data in the Menin fluorescence polarization (FP) assay (1), Menin/MLL homogenous time-resolved fluorescence (HTRF) assay (2) and proliferation assay (3).
NT: not tested

| Co. No. | (1) Menin FP assay ($IC_{50}$ (µM)) | (2) Menin HTRF assay ($IC_{50}$ (nM)) | (3) Spheroid assay MV-4-11 ($IC_{50}$(µM)) | (3) Spheroid assay MOLM14 ($IC_{50}$(µM)) | (3)Spheroid assay K562 |
|---|---|---|---|---|---|
| B1A | 0.054 | 50 | 2.5 | 11.3 | NT |
| B1B | 0.44 | 788 | 8.9 | >15 | NT |
| 3 | 0.038 | 14 | 0.44 | 3.1 | 9.7 |
| 4 | 0.23 | 330 | 2.9 | 7.6 | 8.8 |
| 5 | 6.36 | 9532 | NT | NT | NT |
| 5a | 6.15 | 8285 | NT | NT | NT |
| 6 | NT | 60 | 2.2 | NT | NT |
| 7 | NT | 55 | 1.6 | NT | NT |
| 8 | NT | 64 | 1.6 | NT | NT |
| 9 | NT | 36 | 1.4 | NT | NT |
| 10B | NT | 1315 | 5.0 | 14.2 | NT |
| 11 | NT | 69 | 2.0 | NT | NT |
| 10A | NT | 1532 | NT | NT | NT |
| 9A | NT | 548 | NT | NT | NT |
| 9B | NT | 99 | 0.9 | NT | NT |
| 11B | NT | 1469 | NT | NT | NT |
| 11A | NT | 55 | 1.6 | NT | NT |
| 12 | NT | 5790 | NT | NT | NT |
| 13A | NT | 5269 | NT | NT | NT |
| 13B | NT | 2456 | NT | NT | NT |
| 14A | NT | 4468 | NT | NT | NT |
| 14B | NT | 767 | NT | NT | NT |
| 15 | NT | 606 | NT | NT | NT |
| 16 | NT | 21 | 0.8 | 4.9 | NT |
| 17 | NT | 33 | 1.3 | NT | NT |
| 18 | NT | 563 | 4.7 | NT | NT |
| 19 | NT | 41 | 2.0 | NT | NT |
| 21 | NT | 97 | 1.0 | 6.1 | NT |
| 22 | NT | 78 | 2.5 | 9.9 | NT |
| 23 | NT | 150 | 3.1 | 9.4 | NT |
| 24 | NT | 53 | 1.2 | NT | NT |
| 26 | NT | 27 | NT | NT | NT |

TABLE 4-continued

Biological data in the Menin fluorescence polarization (FP) assay (1), Menin/MLL homogenous time-resolved fluorescence (HTRF) assay (2) and proliferation assay (3).
NT: not tested

| Co. No. | (1) Menin FP assay (IC$_{50}$ (µM)) | (2) Menin HTRF assay (IC$_{50}$ (nM)) | (3) Spheroid assay MV-4-11 (IC$_{50}$(µM)) | (3) Spheroid assay MOLM14 (IC$_{50}$(µM)) | (3)Spheroid assay K562 |
|---|---|---|---|---|---|
| 27 | NT | NT | NT | NT | NT |
| 28 | NT | 149 | 3.4 | NT | NT |
| 29 | NT | 40 | 2.1 | NT | NT |
| 30 | NT | 186 | 4.45 | NT | NT |
| 31 | NT | 34 | 1.4 | NT | NT |
| 32 | NT | 758 | NT | NT | NT |
| 33 | NT | 27 | 2 | NT | NT |
| 34 | NT | 216 | 3.2 | NT | NT |
| 35 | NT | 1012 | NT | NT | NT |
| 36 | NT | 170 | 2.5 | NT | NT |
| 39 | NT | 852 | NT | NT | NT |
| 44 | NT | 137 | 4.3 | NT | NT |
| 49 | NT | 45 | 1.1 | NT | NT |
| 50 | NT | 185 | 2.3 | NT | NT |
| 52 | NT | 20820 | NT | NT | NT |
| 53 | NT | 204 | 2.1 | NT | NT |
| 54A | NT | 11888 | NT | NT | NT |
| 54B | NT | 13225 | NT | NT | NT |
| 54C | NT | 1488 | NT | NT | NT |
| 54D | NT | 6764 | NT | NT | NT |
| 55 | NT | 227 | NT | NT | NT |
| 56 | NT | 724 | NT | NT | NT |
| 57A | NT | 194 | 2.8 | NT | NT |
| 57B | NT | 222 | 4.4 | NT | NT |
| 58A | NT | 1552 | NT | NT | NT |
| 58B | NT | 888 | NT | NT | NT |
| 59A | NT | 709 | NT | NT | NT |
| 59B | NT | 1150 | NT | NT | NT |
| 60A | NT | 493 | 5.5 | NT | NT |
| 60B | NT | 295 | 2.4 | NT | NT |
| 61 | NT | 181 | NT | NT | NT |
| 62 | NT | 724 | NT | NT | NT |
| 63 | NT | 369 | NT | NT | NT |
| 65A | NT | 3496 | NT | NT | NT |
| 65B | NT | 284 | 4.3 | NT | NT |
| 65C | NT | 686 | NT | NT | NT |
| 65D | NT | 8694 | NT | NT | NT |
| 66A | NT | 7437 | NT | NT | NT |
| 66B | NT | 164 | 3.8 | NT | NT |
| 66C | NT | 5378 | NT | NT | NT |
| 66D | NT | 880 | NT | NT | NT |
| 67A | NT | 396 | 3.6 | NT | NT |
| 67B | NT | 348 | 3.7 | NT | NT |
| 68A | NT | 103 | 1.9 | NT | NT |
| 68B | NT | 522 | NT | NT | NT |
| 68C | NT | 282 | 4.4 | 7.7 | NT |
| 69 | NT | 598 | NT | NT | NT |

NT: not tested

The invention claimed is:

1. A compound of Formula (I)

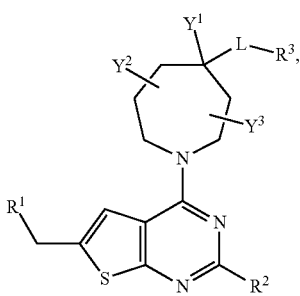

(I)

or a tautomer or a stereoisomeric form thereof, wherein $R^1$ is selected from the group consisting of $CH_3$, $CH_2F$, $CHF_2$ and $CF_3$;

$R^2$ is selected from the group consisting of hydrogen and $CH_3$;

$Y^1$ is selected from the group consisting of hydrogen; $C_{1-6}$alkyl; C-linked 4- to 7-membered non-aromatic heterocyclyl containing at least one nitrogen, oxygen or sulfur atom optionally substituted with a $C_{1-4}$alkyl or cyclopropyl substituent; and $C_{1-4}$alkyl substituted with a substituent selected from the group consisting of fluoro, —CN, phenyl, —OR$^{1Y}$, and —NR$^{2Y}$R$^{2YY}$; wherein $R^{1Y}$ is selected from the group consisting of hydrogen; $C_{1-4}$alkyl optionally substituted with a substituent selected from the group consisting of fluoro, —CN and —C(=O)NR$^{1y}$R$^{2y}$; $C_{2-4}$alkyl substituted with a substituent selected from the group consisting of —OR$^{3y}$ and —NR$^{1y}$R$^{2y}$; and C-linked 4- to 7-membered non-aromatic heterocyclyl containing at least one nitrogen, oxygen or sulfur atom;

$R^{2Y}$ and $R^{2YY}$ are each independently selected from the group consisting of hydrogen; $C_{1-4}$alkyl optionally substituted with a —C(=O)NR$^{1y}$R$^{2y}$ substituent; $C_{2-4}$alkyl substituted with a substituent selected from the group consisting of —OR$^{3y}$ and —NR$^{1y}$R$^{2y}$; and C-linked 4- to 7-membered non-aromatic heterocyclyl containing at least one nitrogen, oxygen or sulfur atom;

$Y^2$ and $Y^3$ are each independently selected from the group consisting of hydrogen; OH; $NH_2$; —C(=O)NR$^{1y}$R$^{2y}$; $C_{1-6}$alkyl; and $C_{1-4}$alkyl substituted with a substituent selected from the group consisting of fluoro, —CN, —OR$^{3Y}$, and —NR$^{4Y}$R$^{4YY}$; with the proviso that when $Y^2$ and $Y^3$ are both substituents at the same carbon atom, and one of $Y^2$ or $Y^3$ is OH or $NH_2$, then the other $Y^3$ or $Y^2$ is H, $C_{1-6}$alkyl, $C_{1-4}$alkyl substituted with a substituent selected from the group consisting of fluoro and —CN, or $C_{2-4}$alkyl substituted with a substituent selected from the group consisting of —OR$^{3Y}$ and —NR$^{4Y}$R$^{4YY}$; wherein $R^{3Y}$ is selected from the group consisting of hydrogen; $C_{1-4}$alkyl optionally substituted with a substituent selected from the group consisting of fluoro, —CN and —C(=O)NR$^{4y}$R$^{5y}$; $C_{2-4}$alkyl substituted with a substituent selected from the group consisting of —OR$^{6y}$ and —NR$^{4y}$R$^{5y}$; and C-linked 4- to 7-membered non-aromatic heterocyclyl containing at least one nitrogen, oxygen or sulfur atom;

$R^{4Y}$ and $R^{4YY}$ are each independently selected from the group consisting of hydrogen; $C_{1-4}$alkyl optionally substituted with a substituent selected from the group consisting of fluoro, —CN and —C(=O)NR$^{1y}$R$^{2y}$; $C_{2-4}$alkyl substituted with a substituent selected from the group consisting of —OR$^{6y}$ and —NR$^{4y}$R$^{5y}$; and C-linked 4- to 7-membered non-aromatic heterocyclyl containing at least one nitrogen, oxygen or sulfur atom; wherein $R^{1y}$, $R^{2y}$, $R^{3y}$, $R^{5y}$ and $R^{6y}$ are each independently selected from the group consisting of hydrogen; $C_{1-4}$alkyl; and C-linked 4- to 7-membered non-aromatic heterocyclyl containing at least one nitrogen, oxygen or sulfur atom; and -L-$R^3$ is selected from (a), (b), (c), (d), (e), or (f):

(a) -L-$R^3$ is $NHR^{1A}$, wherein $R^{1A}$ is selected from the group consisting of hydrogen; $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$ and $R^{2aa}$ are each independently selected from the group consisting of hydrogen, $C_{1-4}$alkyl and cyclopropyl; with the proviso that when $R^{1A}$ is hydrogen, then $Y^1$ is not hydrogen; or (b) L is selected from the group consisting of —O—, —O—$CR^{1B}R^{1BB}$—, —N($R^B$)—, —N($R^B$)—$CR^{1B}R^{1BB}$—, and —(N$R^B$)—$CHR^{1B}$—$CHR^{2B}$—; and $R^3$ is selected from the group consisting of Ar; $Het^1$; $Het^2$; and a 7- to 10-membered saturated spirocarbobicyclic system; wherein $R^B$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —$OR^{1b}$ and —$NR^{2b}R^{2bb}$, wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; —C(=O)$NR^{3B}R^{3BB}$; $C_{1-4}$alkyl optionally substituted with a substituent selected from the group consisting of fluoro, phenyl, $Het^1$, and —CN; $C_{2-4}$alkyl substituted with a substituent selected from the group consisting of —$OR^{4B}$ and —$NR^{5B}R^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a C-linked 4- to 7-membered non-aromatic heterocyclyl containing at least one nitrogen, oxygen or sulfur atom;

$R^{2B}$ is selected from the group consisting of hydrogen; —$OR^{6B}$; —$NR^{7B}R^{7BB}$; —C(=O)$NR^{8B}R^{8BB}$, $C_{1-4}$alkyl optionally substituted with a substituent selected from the group consisting of fluoro, —CN, —$OR^{4B}$, and —$NR^{5B}R^{5BB}$; and C-linked 4- to 7-membered non-aromatic heterocyclyl containing at least one nitrogen, oxygen or sulfur atom; wherein $R^{3B}$, $R^{3BB}$, $R^{4B}$, $R^{5B}$, $R^{5BB}$, $R^{6B}$, $R^{7B}$, $R^{7BB}$, $R^{8B}$ and $R^{8BB}$ are each independently selected from the group consisting of hydrogen; $C_{1-4}$alkyl optionally substituted with a substituent selected from the group consisting of fluoro, —CN and —C(=O)$NR^{9B}R^{9BB}$; and $C_{2-4}$alkyl substituted with a substituent selected from the group consisting of —$OR^{10B}$ and —$NR^{11B}R^{11BB}$; wherein $R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom; or (c) —L-$R^3$ is selected from the group consisting of —N($R^C$)—$CHR^{1C}$—$CO_2R^{2C}$; —N($R^C$)—$CHR^{3C}$—$CONR^{4C}R^{4CC}$; —N($R^C$)—$COR^{5C}$; —N($R^C$)—$SO_2$—$NR^{6C}R^{6CC}$; wherein $R^C$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —$OR^{1c}$ and —$NR^{2c}R^{2cc}$;

$R^{1C}$ and $R^{3C}$ are each selected from the group consisting of hydrogen; —C(=O)$NR^{3c}R^{3cc}$; $C_{1-4}$alkyl optionally substituted with a substituent selected from the group consisting of fluoro, phenyl, $Het^1$, and —CN; $C_{2-4}$alkyl substituted with a substituent selected from the group consisting of —$OR^{4c}$ and —$NR^{5c}R^{5cc}$; and C-linked 4- to 7-membered non-aromatic heterocyclyl containing at least one nitrogen, oxygen or sulfur atom;

$R^{4C}$ and $R^{6C}$ are each selected from the group consisting of hydrogen, and $C_{1-4}$alkyl optionally substituted with a substituent selected from the group consisting of $NR^{6c}R^{6cc}$, Ar, and $Het^1$;

$R^{2C}$ is selected from the group consisting of hydrogen; $C_{1-4}$alkyl optionally substituted with Ar or $Het^1$; Ar; $Het^1$; $Het^2$; and a 7- to 10-membered saturated spirocarbobicyclic system;

$R^{5C}$ is selected from the group consisting of hydrogen; $C_{1-4}$alkyl optionally substituted with —$NR^{2c}R^{2cc}$ Ar or $Het^1$; Ar; $Het^1$; $Het^2$; and a 7- to 10-membered saturated spirocarbobicyclic system; wherein $R^{1c}$, $R^{2c}$, $R^{2cc}$, $R^{3c}$, $R^{3cc}$, $R^{4c}$, $R^{5c}$ and $R^{5cc}$ are each independently selected from the group consisting of hydrogen and $C_{1-4}$alkyl; and $R^{6c}$ and $R^{6cc}$ are each independently selected from the group consisting of hydrogen, and $C_{1-4}$alkyl optionally substituted with a substituent selected from the group consisting of —$NHC_{1-4}$alkyl and cyclopropyl; and $R^{4CC}$ and $R^{6CC}$ are each independently selected from the group consisting of hydrogen; $C_{1-4}$alkyl optionally substituted with Ar or $Het^1$; Ar; $Het^1$; $Het^2$; and a 7- to 10-membered saturated spirocarbobicyclic system; or $R^{4C}$ and $R^{4CC}$, or $R^{6C}$ and $R^{6CC}$ together with the nitrogen atom to which they are attached, form a N-linked $Het^2$; or (d) L is selected from —N($R^D$)—$CR^{1D}R^{1DD}$— and —N($R^D$)—$CR^{1D}R^{1DD}$—$CR^{2D}R^{2DD}$—; wherein $R^D$ is selected from the group consisting of hydrogen; $C_{1-4}$alkyl optionally substituted with a substituent selected from the group consisting of fluoro and —CN; and $C_{2-4}$alkyl substituted with a substituent selected from —$OR^{1d}$ and —$NR^{2d}R^{2dd}$; wherein $R^{1D}$, $R^{1DD}$, and $R^{2DD}$ are each independently selected from the group consisting of hydrogen and $C_{1-4}$alkyl;

$R^{1D}$; $R^{1DD}$; $R^{2D}$ and $R^{2DD}$ are each independently selected from the group consisting of hydrogen and $C_{1-4}$alkyl; and $R^3$ is selected from the group consisting of

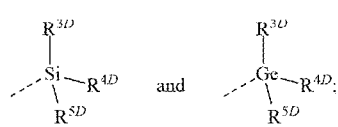

wherein
R$^{3D}$, R$^{4D}$, and R$^{5D}$ are each independently selected from the group consisting of C$_{1-6}$alkyl optionally substituted with a —OH, —OC$_{1-6}$alkyl, or a —NH$_2$ substituent; or
(e) -L-R$^3$ is

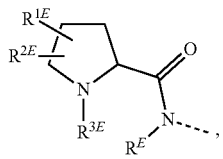

wherein
R$^E$ is selected from the group consisting of hydrogen and C$_{1-4}$alkyl;
R$^{1E}$ is selected from the group consisting of hydrogen, fluoro and C$_{1-4}$alkyl; and
R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a C$_{3-5}$cycloalkyl or a C-linked 4- to 6-membered heterocyclyl containing an oxygen atom; and
R$^{3E}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{4E}$ and —NR$^{5E}$R$^{5EE}$; wherein
R$^{4E}$, R$^{5E}$ and R$^{5EE}$ are each independently selected from the group consisting of hydrogen; C$_{1-4}$alkyl optionally substituted with a substituent selected from the group consisting of fluoro, —CN, and —C(=O)NR$^{6E}$R$^{6EE}$; C$_{2-4}$alkyl substituted with a substituent selected from the group consisting of —OR$^{7E}$ and —NR$^{8E}$R$^{8EE}$; and C-linked 4- to 7-membered non-aromatic heterocyclyl containing at least one nitrogen, oxygen or sulfur atom; wherein
R$^{6E}$, R$^{6EE}$, R$^{7E}$, R$^{8E}$ and R$^{8EE}$ are each independently selected from the group consisting of hydrogen and C$_{1-4}$alkyl; or
(f) -L-R$^3$ is a radical selected from the group consisting of

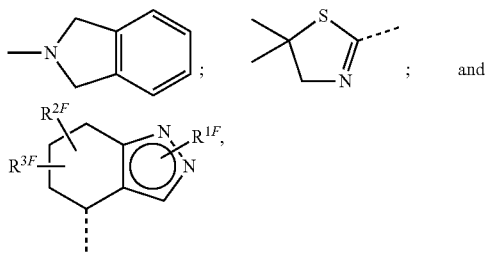

wherein R$^{1F}$ is selected from the group consisting of hydrogen, C$_{1-4}$alkyl and —C$_{2-4}$alkyl-NR$^f$R$^{ff}$; and R$^{2F}$ and R$^{3F}$ are each independently selected from hydrogen and C$_{1-4}$alkyl; wherein R$^f$ and R$^{ff}$ are each independently selected from the group consisting of hydrogen and C$_{1-4}$alkyl;
and wherein
Ar is phenyl optionally substituted with one, two, or three substituents each independently selected from the group consisting of halo, —CN, —OR$^4$, —NR$^5$R$^{5'}$,
—C(=O)NR$^5$R$^{5'}$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$;
Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —NR$^5$R$^{5'}$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$; and
Het$^2$ is a non-aromatic heterocyclyl optionally substituted with one, two, or three substituents each independently selected from the group consisting of halo, —CN, —OR$^4$, —NR$^5$R$^{5'}$, and C$_{1-4}$alkyl optionally substituted with a substituent selected from the group consisting of fluoro, —CN, —OR$^6$, —WIC, and —C(=O)NR$^8$R$^{8'}$;
wherein
R$^4$, R$^5$, R$^{5'}$, R$^6$, R$^7$, R$^{7'}$, R$^8$ and R$^{8'}$ are each independently selected from the group consisting of hydrogen; C$_{1-4}$alkyl optionally substituted with a substituent selected from the group consisting of fluoro and —C(=O)NR$^9$R$^{9'}$; and C$_{2-4}$alkyl substituted with a substituent selected from the group consisting of —OR$^{10}$ and —NR$^{11}$R$^{11'}$; wherein
R$^9$, R$^{9'}$, R$^{10}$, R$^{11}$ and R$^{11'}$ are each independently selected from the group consisting of hydrogen; C$_{1-4}$alkyl; and C-linked 4- to 7-membered non-aromatic heterocyclyl containing at least one nitrogen, oxygen or sulfur atom;
or a pharmaceutically acceptable salt or a solvate thereof.
2. The compound according to claim 1, wherein
R$^1$ is selected from the group consisting of CH$_3$, CH$_2$F, CHF$_2$ and CF$_3$;
R$^2$ is selected from the group consisting of hydrogen and CH$_3$;
Y$^1$ is selected from the group consisting of hydrogen; C$_{1-6}$alkyl; C-linked 4- to 7-membered non-aromatic heterocyclyl containing at least one nitrogen, oxygen or sulfur atom optionally substituted with a C$_{1-4}$alkyl or cyclopropyl substituent; and C$_{1-4}$alkyl substituted with a substituent selected from the group consisting of fluoro, —CN, phenyl, —OR$^{1Y}$, and —NR$^{2Y}$R$^{2YY}$; wherein
R$^{1Y}$, R$^{2Y}$ and R$^{2YY}$ are each independently selected from the group consisting of hydrogen and C$_{1-4}$alkyl;
Y$^2$ and Y$^3$ are each independently selected from the group consisting of hydrogen and C$_{1-6}$alkyl; and
-L-R$^3$ is selected from (a), (b), (c), (e), or (f):
(a) -L-R$^3$ is —NHR$^{1A}$, wherein R$^{1A}$ is selected from the group consisting of hydrogen; C$_{1-6}$alkyl optionally substituted with one, two or three fluoro substituents; and C$_{2-6}$alkyl substituted with a substituent selected from the group consisting of —OR$^{1a}$ and —NR$^{2a}$R$^{2aa}$, wherein R$^{1a}$, R$^{2a}$ and R$^{2aa}$ are each independently selected from the group consisting of hydrogen, C$_{1-4}$alkyl and cyclopropyl; or
(b) L is selected from the group consisting of —N(R$^B$)—, —N(R$^B$)—CR$^{1B}$R$^{1BB}$—, and —(NR$^B$)—CHR$^{1B}$—CHR$^{2B}$—; and R$^3$ is selected from the group consisting of Ar; Het$^1$; and Het$^2$;
wherein
R$^B$ is selected from the group consisting of hydrogen; C$_{1-4}$alkyl optionally substituted with a substituent selected from the group consisting of fluoro, phenyl and —CN; and $C_{2-4}$alkyl substituted with a substituent selected from the group consisting of —OR$^{1b}$ and —NR$^{2b}$R$^{2bb}$; wherein R$^{1b}$, R$^{2b}$, and R$^{2bb}$ are each independently selected from the group consisting of hydrogen, $C_{1-4}$alkyl and cyclopropyl;

R$^{1B}$ is selected from the group consisting of hydrogen; $C_{1-4}$alkyl optionally substituted with a substituent selected from the group consisting of fluoro, phenyl, Het$^1$, and —CN; and $C_{2-4}$alkyl substituted with a substituent selected from the group consisting of —OR$^{4B}$ and —NR$^{5B}$R$^{5BB}$; and R$^{1BB}$ is selected from the group consisting of hydrogen and methyl; or R$^{1B}$ and R$^{1BB}$ together with the carbon to which they are attached form a C-linked 4- to 7-membered non-aromatic heterocyclyl containing at least one nitrogen or oxygen atom;

R$^{2B}$ is selected from the group consisting of hydrogen; and $C_{1-4}$alkyl optionally substituted with a substituent selected from the group consisting of fluoro, —CN, —OR$^{4B}$, and —NR$^{5B}$R$^{5BB}$; wherein R$^{4B}$, R$^{5B}$ and R$^{5BB}$ are each independently selected from the group consisting of hydrogen and $C_{1-4}$alkyl; or (c) -L-R$^3$ is selected from the group consisting of —N(R$^C$)—CHR$^{1C}$—CO$_2$R$^{2C}$;

R$^C$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —OR$^{1c}$ and —NR$^{2c}$R$^{2cc}$;

R$^{1C}$ and R$^{3C}$ are each selected from the group consisting of hydrogen; $C_{1-4}$alkyl optionally substituted with a substituent selected from the group consisting of fluoro, phenyl, Het$^1$, and —CN; and $C_{2-4}$alkyl substituted with a substituent selected from the group consisting of —OR$^{4c}$ and —NR$^{5c}$R$^{5cc}$;

R$^{4C}$ and R$^{6C}$ are each selected from the group consisting of hydrogen, and $C_{1-4}$alkyl optionally substituted with a substituent selected from the group consisting of NR$^{6c}$R$^{6cc}$, Ar, and Het$^1$;

R$^{2C}$ is selected from the group consisting of hydrogen; $C_{1-4}$alkyl optionally substituted with Ar or Het$^1$; Ar; Het$^1$; and Het$^2$;

R$^{5C}$ is selected from the group consisting of hydrogen; $C_{1-4}$alkyl optionally substituted with —NR$^{2c}$R$^{2cc}$, Ar or Het$^1$; Ar; Het$^1$; and Het$^2$; wherein R$^{1c}$, R$^{2c}$, R$^{2cc}$, R$^{4c}$, R$^{5c}$ and R$^{5cc}$ are each independently selected from the group consisting of hydrogen and $C_{1-4}$alkyl; and R$^{6c}$ and R$^{6cc}$ are each independently selected from the group consisting of hydrogen, and $C_{1-4}$alkyl optionally substituted with a substituent selected from the group consisting of —NHC$_{1-4}$alkyl and cyclopropyl; and R$^{4CC}$ and R$^{6CC}$ are each independently selected from the group consisting of hydrogen; $C_{1-4}$alkyl optionally substituted with Ar or Het$^1$; Ar; Het$^1$; and Het$^2$; or R$^{4C}$ and R$^{4cc}$, or R$^{6C}$ and R$^{6CC}$ together with the nitrogen atom to which they are attached, form a N-linked Het$^2$; or (e) -L-R$^3$ is

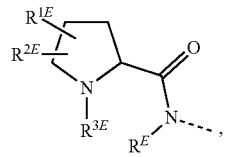

wherein

R$^E$ is selected from the group consisting of hydrogen and $C_{1-4}$alkyl;

R$^{1E}$ is selected from the group consisting of hydrogen, fluoro and $C_{1-4}$alkyl; and R$^{2E}$ is selected from the group consisting of fluoro, —OC$_{1-4}$alkyl, and $C_{1-4}$alkyl optionally substituted with 1, 2 or 3 fluoro substituents; or R$^{1E}$ and R$^{2E}$ are bound to the same carbon atom and together form a $C_{3-5}$cycloalkyl or a C-linked 4- to 6-membered heterocyclyl containing an oxygen atom; and R$^{3E}$ is selected from the group consisting of hydrogen; $C_{1-4}$alkyl optionally substituted with a fluoro or a —CN substituent; and $C_{2-4}$alkyl substituted with a substituent selected from the group consisting of —OR$^{4E}$ and —NR$^{5E}$R$^{5EE}$; wherein R$^{4E}$, R$^{5E}$ and R$^{5EE}$ are each independently selected from the group consisting of hydrogen; $C_{1-4}$alkyl optionally substituted with a substituent selected from the group consisting of fluoro, —CN, and —C(=O)NR$^{6E}$R$^{6EE}$; $C_{2-4}$alkyl substituted with a substituent selected from the group consisting of —OR$^{7E}$ and —NR$^{8E}$R$^{8EE}$; and C-linked 4- to 7-membered non-aromatic heterocyclyl containing at least one nitrogen, oxygen or sulfur atom; wherein R$^{6E}$, R$^{6EE}$, R$^{7E}$, R$^{8E}$ and R$^{8EE}$ are each independently selected from the group consisting of hydrogen and $C_{1-4}$alkyl; or (f) -L-R$^3$ is a radical selected from the group consisting of

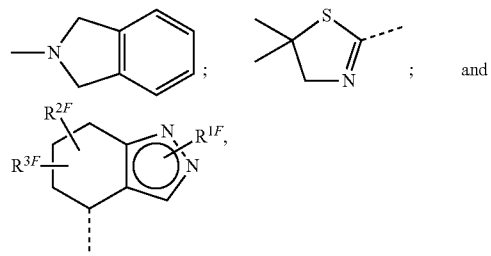

wherein R$^{1f}$ is selected from the group consisting of hydrogen, $C_{1-4}$alkyl and —$C_{2-4}$alkyl-NR$^f$R$^{ff}$; and R$^{2F}$ and R' are each independently selected from hydrogen and $C_{1-4}$alkyl; wherein R$^f$ and R$^{ff}$ are each independently selected from the group consisting of hydrogen and $C_{1-4}$alkyl;

and wherein

Ar is phenyl optionally substituted with one, two, or three substituents each independently selected from the group consisting of halo, —CN, —OR$^4$, —NR$^5$R$^{5'}$, —C(=O)NR$^5$R$^{5'}$, and $C_{1-4}$alkyl;

Het$^1$ is a monocyclic heteroaryl selected from the group consisting of pyridyl, 4-, 5- or 6-pyrimidinyl, pyrazinyl, pyridazinyl, pyrrolyl, pyrazolyl, imidazolyl, and 4- or 5-thiazolyl; each of which may be optionally substituted with one, two, or three substituents each independently selected from the group consisting of halo and $C_{1-4}$alkyl optionally substituted with a substituent selected from the group consisting of fluoro, —CN, —OR$^6$, —NR$^7$R$^7$, and —C(=O)NR$^8$R$^{8'}$; and Het$^2$ is a non-aromatic heterocyclyl selected from azetidinyl, pyrrolidinyl and piperidinyl, each of which may be optionally substituted with one, two, or three substituents each independently selected from the group consisting of halo, —CN, —OR$^4$, —NR$^5$R$^{5'}$, and $C_{1-4}$alkyl; wherein R$^4$, R$^5$, R$^{5'}$, R$^6$, R$^7$, R$^8$ and R$^{8'}$ are each independently selected from the group consisting of hydrogen and $C_{1-4}$alkyl.

3. The compound according to claim 1, wherein

R$^1$ is selected from the group consisting of CH$_3$, CH$_2$F, CHF$_2$ and CF$_3$;

R$^2$ is selected from the group consisting of hydrogen and CH$_3$;

Y$^1$ is selected from the group consisting of hydrogen; $C_{1-6}$alkyl; C-linked 4- to 7-membered non-aromatic heterocyclyl containing at least one nitrogen atom optionally substituted with a $C_{1-4}$alkyl or cyclopropyl substituent; and $C_{1-4}$alkyl substituted with a substituent selected from the group consisting of phenyl, —OR$^{1Y}$, and —NR$^{2Y}$R$^{2YY}$; wherein R$^{1Y}$, R$^{2Y}$ and R$^{2YY}$ are each independently selected from the group consisting of hydrogen and $C_{1-4}$alkyl;

Y$^2$ and Y$^3$ are hydrogen; and

-L-R$^3$ is selected from (a), (b), (c), (e), or (f):

(a) -L-R$^3$ is —NHR$^{1A}$, wherein R$^{1A}$ is selected from the group consisting of hydrogen; $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$ wherein R$^{1a}$, R$^{2a}$ and R$^{2aa}$ are each independently selected from the group consisting of hydrogen, $C_{1-4}$alkyl and cyclopropyl; or (b) L is selected from the group consisting of —N(R$^B$)—, —N(R$^B$)—CR$^{1B}$R$^{1BB}$—, and (NR$^B$)—CHR$^{1B}$—CHR$^{2B}$—; and R$^3$ is selected from the group consisting of Ar; Het$^1$; and Het$^2$;

wherein

R$^B$ is selected from the group consisting of hydrogen; $C_{1-4}$alkyl optionally substituted with a substituent selected from the group consisting of fluoro, phenyl and —CN; and $C_{2-4}$alkyl substituted with a substituent selected from the group consisting of —OR$^{1b}$ and —NR$^{2b}$R$^{2bb}$; wherein R$^{1b}$, R$^{2b}$, and R$^{2bb}$ are each independently selected from the group consisting of hydrogen, $C_{1-4}$alkyl and cyclopropyl;

R$^{1B}$ is selected from the group consisting of hydrogen; $C_{1-4}$alkyl optionally substituted with a phenyl or a Het$^1$ substituent; and $C_{2-4}$alkyl substituted with a substituent selected from the group consisting of —OH and —NH$_2$; and R$^{1BB}$ is hydrogen; or R$^{1B}$ and R$^{1BB}$ together with the carbon to which they are attached form an oxetanyl ring; and R$^{2B}$ is hydrogen; or (c) -L-R$^3$ is selected from the group consisting of —N(R$^C$)—CHR$^{3C}$—CONR$^{4C}$R$^{4CC}$; —N(R$^C$)—COR$^{5C}$; —N(R$^C$)—SO$_2$—NR$^{6C}$R$^{6CC}$, wherein R$^C$ is selected from the group consisting of hydrogen; and $C_{1-4}$alkyl optionally substituted with a phenyl substituent;

R$^{3C}$ is hydrogen or $C_{1-4}$alkyl;

R$^{4C}$ and R$^{6C}$ are each selected from the group consisting of hydrogen and $C_{1-4}$alkyl;

R$^{5C}$ is $C_{1-4}$alkyl optionally substituted with —NR$^{2c}$R$^{2cc}$; wherein R$^{2c}$ and R$^{2cc}$ are each independently selected from the group consisting of hydrogen and $C_{1-4}$alkyl; and R$^{4cc}$ and R$^{6cc}$ are each independently selected from the group consisting of hydrogen and $C_{1-4}$alkyl; or R$^{4C}$ and R$^{4CC}$, or R$^{6C}$ and R$^{6CC}$ together with the nitrogen atom to which they are attached, form a N-linked Het$^2$; or (e) -L-R$^3$ is

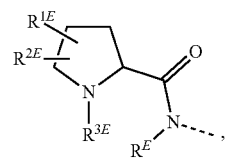

wherein

R$^E$ is selected from the group consisting of hydrogen and $C_{1-4}$alkyl;

R$^{1E}$ is selected from the group consisting of hydrogen, fluoro and $C_{1-4}$alkyl; and R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a $C_{3-5}$cycloalkyl; and R$^{3E}$ is selected from the group consisting of hydrogen and $C_{1-4}$alkyl; or (f) -L-R$^3$ is a radical selected from the group consisting of

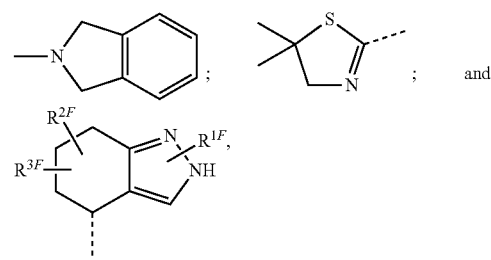

wherein R$^{1F}$ is hydrogen or $C_{1-4}$alkyl;

and wherein

Ar is phenyl optionally substituted with one, two, or three substituents each independently selected from the group consisting of halo, —C(=O)NR$^5$R$^{5'}$, and $C_{1-4}$alkyl; wherein R$^5$ and R$^{5'}$ are each independently selected from the group consisting of hydrogen and $C_{1-4}$alkyl;

Het$^1$ is a monocyclic heteroaryl selected from the group consisting of pyridyl, 4-, 5- or 6-pyrimidinyl, pyrazinyl, pyridazinyl, pyrrolyl, pyrazolyl, and imidazolyl; each of which may be optionally substituted with one, two, or three substituents each independently selected from the group consisting of halo and $C_{1-4}$alkyl; and Het$^2$ is a non-aromatic heterocyclyl selected from azetidinyl, pyrrolidinyl and piperidinyl, each of which may be optionally substituted with one, two, or three substituents each independently selected from the group consisting of halo and $C_{1-4}$alkyl.

4. The compound according to claim 1, wherein
R$^1$ is CF$_3$;
R$^2$ is hydrogen;
Y$^1$ is selected from the group consisting of hydrogen; C$_{1-6}$alkyl; C-linked 4- to 7-membered non-aromatic heterocyclyl containing at least one nitrogen atom optionally substituted with a C$_{1-4}$alkyl substituent; and C$_{1-4}$alkyl substituted with a substituent selected from the group consisting of phenyl, —OH and —OC$_{1-4}$alkyl;
Y$^2$ and Y$^3$ are hydrogen; and
-L-R$^3$ is selected from (a), (b), (c), (e), or (f):
(a) -L-R$^3$ is —NHR$^{1A}$, wherein R$^{1A}$ is selected from the group consisting of hydrogen; C$_{1-6}$alkyl optionally substituted with one, two or three fluoro substituents; and C$_{2-6}$alkyl substituted with a substituent selected from the group consisting of —OR$^{1a}$ and —NR$^{2a}$R$^{2aa}$ wherein R$^{1a}$, R$^{2a}$ and R$^{2aa}$ are each independently selected from the group consisting of hydrogen, C$_{1-4}$alkyl and cyclopropyl; or
(b) L is selected from the group consisting of —N(R$^B$)— and —N(R$^B$)—CR$^{1B}$R$^{1BB}$—; and R$^3$ is selected from the group consisting of Ar; Het$^1$; and Het$^2$; wherein
R$^B$ is selected from the group consisting of hydrogen; C$_{1-4}$alkyl optionally substituted with a phenyl or a —CN substituent; and C$_{2-4}$alkyl substituted with a substituent selected from the group consisting of —OR$^{1b}$ and —NR$^{2b}$R$^{2bb}$; wherein R$^{1b}$, R$^{2b}$, and R$^{2bb}$ are each independently selected from the group consisting of hydrogen and C$_{1-4}$alkyl;
R$^{1B}$ is selected from the group consisting of hydrogen; C$_{1-4}$alkyl optionally substituted with a phenyl or a Het$^1$ substituent; and C$_{2-4}$alkyl substituted with a —OH substituent; and R$^{1BB}$ is hydrogen; or R$^{1B}$ and R$^{1BB}$ together with the carbon to which they are attached form an oxetanyl ring; or
(c) -L-R$^3$ is selected from the group consisting of —N(R$^C$)—CHR$^{3C}$—CONR$^{4C}$R$^{4CC}$; —N(R$^C$)—COR$^{5C}$; and —N(R$^C$)—SO$_2$—NR$^{6C}$R$^{6CC}$, wherein
R$^C$ is selected from the group consisting of hydrogen; and C$_{1-4}$alkyl optionally substituted with a phenyl substituent;
R$^{3C}$, R$^{4C}$ and R$^{6C}$ are each selected from the group consisting of hydrogen and C$_{1-4}$alkyl;
R$^{5C}$ is C$_{1-4}$alkyl optionally substituted with —NR$^{2c}$R$^{2cc}$; wherein R$^{2c}$ and R$^{2cc}$ are each independently selected from the group consisting of hydrogen and C$_{1-4}$alkyl; and
R$^{4cc}$ and R$^{6cc}$ are each independently selected from the group consisting of hydrogen and C$_{1-4}$alkyl; or
(e) -L-R$^3$ is

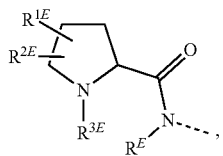

wherein
R$^E$ is selected from the group consisting of hydrogen and methyl;
R$^{1E}$ and R$^{2E}$ are each an independently selected C$_{1-4}$alkyl substituent; or R$^{1E}$ and R$^{2E}$ are bound to the same carbon atom and together form a C$_{3-5}$cycloalkyl; and R$^{3E}$ is hydrogen; or
(f) -L-R$^3$ is

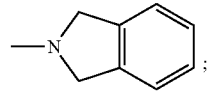

and wherein
Ar is phenyl optionally substituted with one or two substituents each independently selected from the group consisting of halo, —C(=O)NR$^5$R$^{5'}$, and C$_{1-4}$alkyl; wherein R$^5$ and R$^{5'}$ are each independently selected from the group consisting of hydrogen and C$_{1-4}$alkyl;
Het$^1$ is a monocyclic heteroaryl selected from the group consisting of pyridyl, 4-, 5- or 6-pyrimidinyl, pyrazinyl, pyridazinyl, pyrrolyl, pyrazolyl, and imidazolyl; each of which may be optionally substituted with one or two substituents each independently selected from the group consisting of halo and C$_{1-4}$alkyl; and
Het$^2$ is a non-aromatic heterocyclyl selected from azetidinyl, pyrrolidinyl and piperidinyl, each of which may be optionally substituted with a C$_{1-4}$alkyl substituent.
5. The compound according to claim 1, wherein
R$^1$ is CF$_3$;
R$^2$ is hydrogen;
Y$^1$, Y$^2$ and Y$^3$ are hydrogen; and
-L-R$^3$ is selected from (a), (b), (c), (e), or (f):
(a) -L-R$^3$ is —NHR$^{1A}$, wherein R$^{1A}$ is selected from the group consisting of C$_{1-6}$alkyl optionally substituted with one, two or three fluoro substituents; and C$_{2-6}$alkyl substituted with a substituent selected from the group consisting of —OR$^{1a}$ and —NR$^{2a}$R$^{2aa}$, wherein R$^{1a}$, R$^{2a}$ and R$^{2aa}$ are each independently selected from the group consisting of hydrogen, C$_{1-4}$alkyl and cyclopropyl; or
(b) L is —N(R$^B$)—CR$^{1B}$R$^{1BB}$— and R$^3$ is selected from the group consisting of Ar and Het$^1$; wherein
R$^B$ is selected from the group consisting of hydrogen; C$_{1-4}$alkyl optionally substituted with a phenyl or a —CN substituent; and C$_{2-4}$alkyl substituted with a substituent selected from the group consisting of —OR$^{1b}$ and —NR$^{2b}$R$^{2bb}$, wherein
R$^{1b}$, R$^{2b}$, and R$^{2bb}$ are each independently selected from the group consisting of hydrogen and C$_{1-4}$alkyl;
R$^{1B}$ is selected from the group consisting of hydrogen; C$_{1-4}$alkyl optionally substituted with a Het$^1$ substituent; and C$_{2-4}$alkyl substituted with a —OH substituent; and R$^{1B}$ is hydrogen; or R$^{1B}$ and R$^{1BB}$ together with the carbon to which they are attached form an oxetanyl ring; or
(c) -L-R$^3$ is selected from the group consisting of —N(R$^C$)—CHR$^{3C}$—CONR$^{4C}$R$^{4CC}$; —N(R$^C$)—COR$^{5C}$; and —N(R$^C$)—SO$_2$—NR$^{6C}$R$^{6CC}$; wherein
R$^C$ is selected from the group consisting of hydrogen; and C$_{1-4}$alkyl optionally substituted with a phenyl substituent;
R$^{3C}$, R$^{4C}$ and R$^{6C}$ are each selected from the group consisting of hydrogen and C$_{1-4}$alkyl;
R$^{5C}$ is C$_{1-4}$alkyl optionally substituted with —NR$^{2c}$R$^{2cc}$; wherein R$^{2c}$ and R$^{2cc}$ are each independently selected from the group consisting of hydrogen and C$_{1-4}$alkyl; and R$^{4CC}$ and R$^{6CC}$ are each independently selected from the group consisting of hydrogen and C$_{1-4}$alkyl; or
(e) -L-R$^3$ is

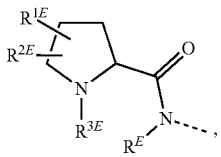

wherein
R$^E$ is selected from the group consisting of hydrogen and methyl;
R$^{1E}$ and R$^{2E}$ are each an independently selected C$_{1-4}$alkyl substituent; or R$^{1E}$ and R$^{2E}$ are bound to the same carbon atom and together form a C$_{3-5}$cycloalkyl; and R$^{3E}$ is hydrogen; or
(f) -L-R$^3$ is

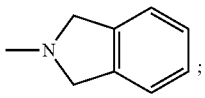

and wherein
Ar is phenyl optionally substituted with one or two substituents each independently selected from the group consisting of halo, —C(=O)NR$^5$R$^{5'}$, and C$_{1-4}$alkyl; wherein R$^5$ and R$^{5'}$ are each independently selected from the group consisting of hydrogen and C$_{1-4}$alkyl; and
Het$^1$ is a monocyclic heteroaryl selected from the group consisting of pyridyl, 4-, 5- or 6-pyrimidinyl, pyrazinyl, pyridazinyl, pyrrolyl, pyrazolyl, and imidazolyl; each of which may be optionally substituted with one or two substituents each independently selected from the group consisting of halo and C$_{1-4}$alkyl.

6. The compound according to claim 1, wherein
R$^1$ is selected from the group consisting of CH$_3$, CH$_2$F, CHF$_2$ and CF$_3$;
R$^2$ is selected from the group consisting of hydrogen and CH$_3$;
Y$^1$ is selected from the group consisting of hydrogen; C$_{1-6}$alkyl; C-linked 4- to 7-membered non-aromatic heterocyclyl containing at least one nitrogen, oxygen or sulfur atom optionally substituted with a C$_{1-4}$alkyl or cyclopropyl substituent; and C$_{1-4}$alkyl substituted with a substituent selected from the group consisting of fluoro, —CN, phenyl, —OR$^{1Y}$, and —NR$^{2Y}$R$^{2YY}$; wherein
R$^{1Y}$ is selected from the group consisting of hydrogen; C$_{1-4}$alkyl optionally substituted with a substituent selected from the group consisting of fluoro, —CN and —C(=O)NR$^{1y}$R$^{2y}$; C$_{2-4}$alkyl substituted with a substituent selected from the group consisting of —OR$^{3y}$ and —NR$^{1y}$R$^{2y}$; and C-linked 4- to 7-membered non-aromatic heterocyclyl containing at least one nitrogen, oxygen or sulfur atom;
R$^{2Y}$ and R$^{2YY}$ are each independently selected from the group consisting of hydrogen; C$_{1-4}$alkyl optionally substituted with a —C(=O)NR$^{1y}$R$^{2y}$ substituent; C$_{2-4}$alkyl substituted with a substituent selected from the group consisting of —OR$^{3y}$ and —NR$^{1y}$R$^{2y}$; and C-linked 4- to 7-membered non-aromatic heterocyclyl containing at least one nitrogen, oxygen or sulfur atom;
Y$^2$ and Y$^3$ are each independently selected from the group consisting of hydrogen; OH; NH$_2$;
—C(=O)NR$^{1y}$R$^{2y}$; C$_{1-6}$alkyl; and C$_{1-4}$alkyl substituted with a substituent selected from the group consisting of fluoro, —CN, —OR$^{3Y}$, and —NR$^{4Y}$R$^{4YY}$; with the proviso that when Y$^2$ and Y$^3$ are both substituents at the same carbon atom, and one of Y$^2$ or Y$^3$ is OH or NH$_2$, then the other Y$^3$ or Y$^2$ is H, C$_{1-6}$alkyl, C$_{1-4}$alkyl substituted with a substituent selected from the group consisting of fluoro and —CN, or C$_{2-4}$alkyl substituted with a substituent selected from the group consisting of —OR$^{3Y}$ and —NR$^{4Y}$R$^{4YY}$; wherein
R$^{3Y}$ is selected from the group consisting of hydrogen; C$_{1-4}$alkyl optionally substituted with a substituent selected from the group consisting of fluoro, —CN and —C(=O)NR$^4$R$^{5Y}$; C$_{2-4}$alkyl substituted with a substituent selected from the group consisting of —OR$^{6y}$ and —NR$^{4y}$R$^{5y}$; and C-linked 4- to 7-membered non-aromatic heterocyclyl containing at least one nitrogen, oxygen or sulfur atom;
R$^{4Y}$ and R$^{4YY}$ are each independently selected from the group consisting of hydrogen; C$_{1-4}$alkyl optionally substituted with a substituent selected from the group consisting of fluoro, —CN and —C(=O)NR$^{1y}$R$^{2y}$; C$_{2-4}$alkyl substituted with a substituent selected from the group consisting of —OR$^{6y}$ and —NR$^{4y}$R$^{5y}$; and C-linked 4- to 7-membered non-aromatic heterocyclyl containing at least one nitrogen, oxygen or sulfur atom; wherein
R$^{1y}$, R$^{2y}$, R$^{3y}$, R$^{4y}$, R$^{5y}$ and R$^{6y}$ are each independently selected from the group consisting of hydrogen; C$_{1-4}$alkyl; and C-linked 4- to 7-membered non-aromatic heterocyclyl containing at least one nitrogen, oxygen or sulfur atom; and
-L-R$^3$ is selected from (a), (b), (c), (d), or (e):
(a) -L-R$^3$ is —NHR$^{1A}$, wherein R$^{1A}$ is selected from the group consisting of hydrogen; C$_{1-6}$alkyl optionally substituted with one, two or three fluoro substituents; and C$_{2-6}$alkyl substituted with a substituent selected from the group consisting of —OR$^{1a}$ and —NR$^{2a}$R$^{2aa}$, wherein R$^{1a}$, R$^{2a}$ and R$^{2aa}$ are each independently selected from the group consisting of hydrogen, C$_{1-4}$alkyl and cyclopropyl; with the proviso that when R$^{1A}$ is hydrogen, then Y$^1$ is not hydrogen; or
(b) L is selected from the group consisting of —N(R$^B$)—, —N(R$^B$)—CR$^{1B}$R$^{1BB}$—, and —(NR$^B$)—CHR$^{1B}$—CHR$^{2B}$—; and R$^3$ is selected from the group consisting of Ar; Het$^1$; Het$^2$; and a 7- to 10-membered saturated spirocarbobicyclic system; wherein
R$^B$ is selected from the group consisting of hydrogen; C$_{1-4}$alkyl optionally substituted with a substituent selected from the group consisting of fluoro, phenyl and —CN; and C$_{2-4}$alkyl substituted with a substituent selected from the group consisting of —OR$^{1b}$ and —NR$^{2b}$R$^{2bb}$; wherein
R$^{1b}$, R$^{2b}$, and R$^{2bb}$ are each independently selected from the group consisting of hydrogen, C$_{1-4}$alkyl and cyclopropyl;
R$^{1B}$ is selected from the group consisting of hydrogen; —C(=O)NR$^{3B}$R$^{3BB}$;
C$_{1-4}$alkyl optionally substituted with a substituent selected from the group consisting of fluoro, phenyl, Het$^1$, and —CN; C$_{2-4}$alkyl substituted with a substituent selected from the group consisting of —OR$^{4B}$ and —NR$^{5B}$R$^{5BB}$; and C-linked 4- to 7-membered non-aromatic heterocyclyl containing at least one nitrogen, oxygen or sulfur atom; and R$^{1BB}$ is selected from the group consisting of hydrogen and methyl; or R$^{1B}$ and R$^{1BB}$ together with the carbon to which they are attached form a C-linked 4- to 7-membered non-aromatic heterocyclyl containing at least one nitrogen, oxygen or sulfur atom;

R$^{2B}$ is selected from the group consisting of hydrogen; —OR$^{6B}$; —NR$^{7B}$R$^{7BB}$;
—C(=O)NR$^{8B}$R$^{8BB}$; C$_{1-4}$alkyl optionally substituted with a substituent selected from the group consisting of fluoro, —CN, —OR$^{4B}$, and —NR$^{5B}$R$^{5BB}$; and C-linked 4- to 7-membered non-aromatic heterocyclyl containing at least one nitrogen, oxygen or sulfur atom; wherein R$^{3B}$, R$^{3BB}$, R$^{4B}$, R$^{5B}$, R$^{5BB}$, R$^{6B}$, R$^{7B}$, R$^{7BB}$, R$^{8B}$ and R$^{BBB}$ are each independently selected from the group consisting of hydrogen; C$_{1-4}$alkyl optionally substituted with a substituent selected from the group consisting of fluoro, —CN and —C(=O)NR$^{9B}$R$^{9BB}$; and C$_{2-4}$alkyl substituted with a substituent selected from the group consisting of —OR$^{10B}$ and —NR$^{11B}$R$^{11BB}$; wherein R$^{9B}$, R$^{9BB}$, R$^{10B}$, R$^{11B}$ and R$^{11BB}$ are each independently selected from the group consisting of hydrogen; C$_{1-4}$alkyl; and C-linked 4- to 7-membered non-aromatic heterocyclyl containing at least one nitrogen, oxygen or sulfur atom; or (c) -L-R$^3$ is selected from the group consisting of —N(R$^C$)—CHR$^{1C}$—CO$_2$R$^{2C}$;
—N(R$^C$)—CHR$^{3C}$—CONR$^{4C}$R$^{4CC}$; —N(R$^C$)—COR$^{5C}$;
—N(R$^C$)—SO$_2$—NR$^{6C}$R$^{6CC}$; wherein R$^C$ is selected from the group consisting of hydrogen; C$_{1-4}$alkyl optionally substituted with a substituent selected from the group consisting of fluoro, phenyl and —CN; and C$_{2-4}$alkyl substituted with a substituent selected from the group consisting of —OR$^{1c}$ and —NR$^{2c}$R$^{2cc}$;

R$^{1C}$ and R$^{3C}$ are each selected from the group consisting of hydrogen;
—C(=O)NR$^{3c}$R$^{3cc}$; C$_{1-4}$alkyl optionally substituted with a substituent selected from the group consisting of fluoro, phenyl, Het$^1$, and —CN; C$_{2-4}$alkyl substituted with a substituent selected from the group consisting of —OR$^{4c}$ and —NR$^{5c}$R$^{5cc}$; and
C-linked 4- to 7-membered non-aromatic heterocyclyl containing at least one nitrogen, oxygen or sulfur atom;

R$^{4C}$ and R$^{6C}$ are each selected from the group consisting of hydrogen, and C$_{1-4}$alkyl optionally substituted with a substituent selected from the group consisting of NR$^{6c}$R$^{6cc}$, Ar, and Het$^1$;

R$^{2C}$ is selected from the group consisting of hydrogen; C$_{1-4}$alkyl optionally substituted with Ar or Het$^1$; Ar; Het$^1$; Het$^2$; and a 7- to 10-membered saturated spirocarbobicyclic system;

R$^{5C}$ is selected from the group consisting of hydrogen; C$_{1-4}$alkyl optionally substituted with —NR$^{2c}$R$^{2cc}$ Ar or Het$^1$; Ar; Het$^1$; Het$^2$; and a 7- to 10-membered saturated spirocarbobicyclic system; wherein R$^{1c}$, R$^{2c}$, R$^{2cc}$, R$^{3c}$, R$^{3cc}$, R$^{4c}$, R$^{5c}$ and R$^{5cc}$ are each independently selected from the group consisting of hydrogen and C$_{1-4}$alkyl; and R$^{6c}$ and R$^{6cc}$ are each independently selected from the group consisting of hydrogen, and C$_{1-4}$alkyl optionally substituted with a substituent selected from the group consisting of —NHC$_{1-4}$alkyl and cyclopropyl; and R$^{4CC}$ and R$^{6CC}$ are each independently selected from the group consisting of hydrogen; C$_{1-4}$alkyl optionally substituted with Ar or Het$^1$; Ar; Het$^1$; Het$^2$; and a 7- to 10-membered saturated spirocarbobicyclic system; or R$^{4C}$ and R$^{4CC}$, or R$^{6C}$ and R$^{6CC}$ together with the nitrogen atom to which they are attached, form a N-linked Het$^2$; or (d) L is selected from —N(R$^D$)—CR$^{1D}$R$^{1DD}$— and —N(R$^D$)—CR$^{1D}$R$^{1DD}$—CR$^{2D}$R$^{2DD}$—; wherein R$^D$ is selected from the group consisting of hydrogen; C$_{1-4}$alkyl optionally substituted with a substituent selected from the group consisting of fluoro and —CN; and C$_{2-4}$alkyl substituted with a substituent selected from —OR$^{1d}$ and —NR$^{2d}$R$^{2dd}$; wherein R$^{1d}$, R$^{2d}$ and R$^{2dd}$ are each independently selected from the group consisting of hydrogen and C$_{1-4}$alkyl;

R$^{1D}$, R$^{1DD}$, R$^{2D}$ and R$^{2DD}$ are each independently selected from the group consisting of hydrogen and C$_{1-4}$alkyl; and R$^3$ is selected from the group consisting of

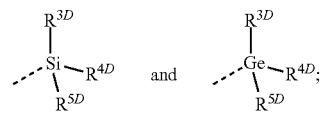

wherein R$^{3D}$, R$^{4D}$, and R$^{5D}$ are each independently selected from the group consisting of C$_{1-6}$alkyl optionally substituted with a —OH, —OC$_{1-6}$alkyl, or a —NH$_2$ substituent; or (e) -L-R$^3$ is

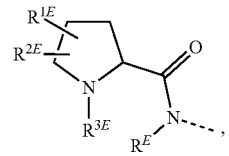

wherein

R$^E$ is selected from the group consisting of hydrogen and C$_{1-4}$alkyl;

R$^{1E}$ is selected from the group consisting of hydrogen, fluoro and C$_{1-4}$alkyl; and R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a C$_{3-5}$cycloalkyl or a C-linked 4- to 6-membered heterocyclyl containing an oxygen atom; and R$^{3E}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{4E}$ and —NR$^{5E}$R$^{5EE}$; wherein R$^{4E}$, R$^{5E}$ and R$^{5EE}$ are each independently selected from the group consisting of hydrogen; C$_{1-4}$alkyl optionally substituted with a substituent selected from the group consisting of fluoro, —CN, and —C(=O)NR$^{6E}$R$^{6EE}$; C$_{2-4}$alkyl substituted with a substituent selected from the group consisting of —OR$^{7E}$ and —NR$^{8E}$R$^{8EE}$, and C-linked 4- to 7-membered non-aromatic heterocyclyl containing at least one nitrogen, oxygen or sulfur atom; wherein R⁶ᴱ, R⁶ᴱᴱ, R⁷ᴱ, R⁸ᴱ and R⁸ᴱᴱ are each independently selected from the group consisting of hydrogen and $C_{1-4}$alkyl;
and wherein
Ar is phenyl optionally substituted with one, two, or three substituents each independently selected from the group consisting of halo, —CN, —OR⁴, —NR⁵R⁵', —C(=O)NR⁵R⁵', and $C_{1-4}$alkyl optionally substituted with a substituent selected from the group consisting of fluoro, —CN, —OR⁶, —NR⁷R⁷', and —C(=O)NR⁸R⁸';
Het¹ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —NR⁵R⁵', and $C_{1-4}$alkyl optionally substituted with a substituent selected from the group consisting of fluoro, —CN, —OR⁶, —NR⁷R⁷', and —C(=O)NR⁸R⁸'; and
Het² is a non-aromatic heterocyclyl optionally substituted with one, two, or three substituents each independently selected from the group consisting of halo, —CN, —OR⁴, —NR⁵R⁵', and $C_{1-4}$alkyl optionally substituted with a substituent selected from the group consisting of fluoro, —CN, —OR⁶, —NR⁷R⁷', and —C(=O)NR⁸R⁸';
wherein
R⁴, R⁵, R⁵', R⁶, R⁷, R⁷', R⁸ and R⁸' are each independently selected from the group consisting of hydrogen; $C_{1-4}$alkyl optionally substituted with a substituent selected from the group consisting of fluoro and —C(=O)NR⁹R⁹'; and $C_{2-4}$alkyl substituted with a substituent selected from the group consisting of —OR¹⁰ and —NR¹¹R¹¹'; wherein
R⁹, R⁹', R¹⁰, R¹¹ and R¹¹' are each independently selected from the group consisting of hydrogen; $C_{1-4}$alkyl; and C-linked 4- to 7-membered non-aromatic heterocyclyl containing at least one nitrogen, oxygen or sulfur atom.

7. The compound according to claim 1, wherein
R¹ is CF₃;
R² is hydrogen;
Y¹ is hydrogen;
Y² and Y³ are each independently selected from the group consisting of hydrogen and $C_{1-6}$alkyl;
-L-R³ is selected from (a), (b), (c), (e), or (f):
(a) -L-R³ is —NHR¹ᴬ, wherein R¹ᴬ is selected from the group consisting of $C_{1-6}$alkyl optionally substituted with one, two or three fluoro substituents; and $C_{2-6}$alkyl substituted with a substituent selected from the group consisting of —OR¹ᵃ and —NR²ᵃR²ᵃᵃ, wherein R¹ᵃ, R²ᵃ and R²ᵃᵃ are each independently selected from the group consisting of hydrogen and $C_{1-4}$alkyl; or
(b) L is selected from the group consisting of —O—, —O—CR¹ᴮR¹ᴮᴮ—, —N(Rᴮ)—, and —N(Rᴮ)—CR¹ᴮR¹ᴮᴮ—; and R³ is selected from the group consisting of Ar; Het¹; and Het²;
wherein
Rᴮ is selected from the group consisting of hydrogen; $C_{1-4}$alkyl optionally substituted with a phenyl; and $C_{2-4}$alkyl substituted with a substituent selected from the group consisting of —OR¹ᵇ and —NR²ᵇR²ᵇᵇ, wherein R¹ᵇ, R²ᵇ, and R²ᵇᵇ are each independently selected from the group consisting of hydrogen, and $C_{1-4}$alkyl;
R¹ᴮ is selected from the group consisting of hydrogen and $C_{1-4}$alkyl; and
R¹ᴮᴮ is hydrogen; or
(c) -L-R³ is selected from the group consisting of —N(Rᶜ)—CHR³ᶜ—CONR⁴ᶜR⁴ᶜᶜ, and —N(Rᶜ)—COR⁵ᶜ; wherein
Rᶜ is hydrogen;
R³ᶜ is $C_{1-4}$alkyl;
R⁴ᶜ is hydrogen;
R⁵ᶜ is Het²; and
R⁴ᶜᶜ is $C_{1-4}$alkyl; or
(e) -L-R³ is

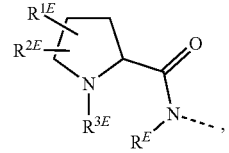

wherein
Rᴱ is hydrogen;
R¹ᴱ and R²ᴱ are bound to the same carbon atom and together form a $C_{3-5}$cycloalkyl; and
R³ᴱ is hydrogen; or
(f) -L-R³ is a radical consisting of the group consisting of

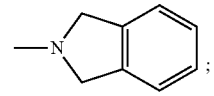

and wherein
Ar is phenyl optionally substituted with one, two or three substituents each independently selected from the group consisting of halo, —OR⁴, —C(=O)NR⁵R⁵', and
$C_{1-4}$alkyl optionally substituted with a substituent selected from the group consisting of —OR⁶, and —NR⁷R⁷';
Het¹ is a monocyclic heteroaryl selected from the group consisting of pyridyl, 4-, 5- or 6-pyrimidinyl, pyridazinyl, and pyrazolyl; each of which may be optionally substituted with one, two, or three substituents each independently selected from $C_{1-4}$alkyl optionally substituted with a —OR⁶ substituent; and
Het² is a non-aromatic heterocyclyl optionally substituted with one, two, or three $C_{1-4}$alkyl substituents;
wherein
R⁴, R⁵, R⁵', R⁶, R⁷, and R⁷' are each independently selected from the group consisting of hydrogen and $C_{1-4}$alkyl.

8. The compound according to claim 6, wherein
R¹ is CF₃;
R² is hydrogen;
Y¹ is hydrogen;
Y² and Y³ are each independently selected from the group consisting of hydrogen and $C_{1-6}$alkyl;
-L-R³ is selected from (a), (b), (c), or (e):
(a) -L-R³ is —NHR¹ᴬ, wherein R¹ᴬ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$ and $R^{2aa}$ are each independently selected from the group consisting of hydrogen and $C_{1-4}$alkyl; or (b) L is selected from the group consisting of —$N(R^B)$—, and —$N(R^B)$—$CR^{1B}R^{1BB}$—;

and $R^3$ is selected from the group consisting of Ar; $Het^1$; and $Het^2$; wherein $R^B$ is selected from the group consisting of hydrogen; $C_{1-4}$alkyl optionally substituted with a phenyl; and $C_{2-4}$alkyl substituted with a substituent selected from the group consisting of —$OR^{1b}$ and —$NR^{2b}R^{2bb}$; wherein $R^{1b}$, $R^{2b}$, and $R^{2bb}$ are each independently selected from the group consisting of hydrogen, and $C_{1-4}$alkyl;

$R^{1B}$ is selected from the group consisting of hydrogen and $C_{1-4}$alkyl; and $R^{1BB}$ is hydrogen; or (c) -L-$R^3$ is selected from the group consisting of —$N(R^C)$—$CHR^{3C}$—$CONR^{4c}R^{4CC}$, and —$N(R^C)$—$COR^{5C}$; wherein $R^C$ is hydrogen;
$R^{3C}$ is $C_{1-4}$alkyl;
$R^{4C}$ is hydrogen;
$R^{5C}$ is $Het^2$; and
$R^{4CC}$ is $C_{1-4}$alkyl; or (e) -L-$R^3$ is

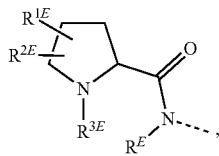

wherein $R^E$ is hydrogen;

$R^{1E}$ and $R^{2E}$ are bound to the same carbon atom and together form a $C_{3-5}$cycloalkyl; and $R^{3E}$ is hydrogen;

and wherein

Ar is phenyl optionally substituted with one, two, or three substituents each independently selected from the group consisting of halo, —$OR^4$, —$C(=O)NR^5R^{5'}$, and $C_{1-4}$alkyl optionally substituted with a substituent selected from the group consisting of —$OR^6$, and —$NR^7R^{7'}$;

$Het^1$ is a monocyclic heteroaryl selected from the group consisting of pyridyl, 4-, 5- or 6-pyrimidinyl, pyridazinyl, and pyrazolyl; each of which may be optionally substituted with one, two, or three substituents each independently selected from $C_{1-4}$alkyl optionally substituted with a —$OR^6$ substituent; and $Het^2$ is a non-aromatic heterocyclyl optionally substituted with one, two, or three $C_{1-4}$alkyl substituents;

wherein $R^4$, $R^5$, $R^{5'}$, $R^6$, $R^7$, and $R^{7'}$ are each independently selected from the group consisting of hydrogen and $C_{1-4}$alkyl.

9. A pharmaceutical composition comprising a compound as claimed in claim 1 and a pharmaceutically acceptable carrier or diluent.

10. A process for preparing a pharmaceutical composition comprising mixing a pharmaceutically acceptable carrier or diluent with a therapeutically effective amount of a compound according to claim 1.

* * * * *